US011033403B2

(12) United States Patent
Predick et al.

(10) Patent No.: US 11,033,403 B2
(45) Date of Patent: Jun. 15, 2021

(54) EXPANDABLE IMPLANT ASSEMBLY

(71) Applicant: Life Spine, Inc., Huntley, IL (US)

(72) Inventors: Daniel Predick, West Lafayette, IN (US); Madeline Wolters, Carol Stream, IL (US); Michael S. Butler, St. Charles, IL (US)

(73) Assignee: LIFE SPINE, INC., Huntley, IL (US)

( * ) Notice: Subject to any disclaimer, the term of this patent is extended or adjusted under 35 U.S.C. 154(b) by 72 days.

(21) Appl. No.: 16/438,076

(22) Filed: Jun. 11, 2019

(65) Prior Publication Data

US 2019/0307577 A1 Oct. 10, 2019

Related U.S. Application Data

(63) Continuation-in-part of application No. PCT/US2018/041306, filed on Jul. 9, 2018, which is
(Continued)

(51) Int. Cl.
*A61F 2/44* (2006.01)
*A61F 2/30* (2006.01)

(52) U.S. Cl.
CPC .. *A61F 2/4455* (2013.01); *A61F 2002/30329* (2013.01); *A61F 2002/30538* (2013.01);
(Continued)

(58) Field of Classification Search
CPC .......... A61F 2/44; A61F 2/4455; A61F 2/447; A61F 2/4465
See application file for complete search history.

(56) References Cited

U.S. PATENT DOCUMENTS

| 4,466,426 A | 8/1984 | Blackman |
| 4,636,217 A | 1/1987 | Ogilvie et al. |

(Continued)

FOREIGN PATENT DOCUMENTS

| CN | 102427769 A | 4/2012 |
| EP | 2 777 633 A2 | 9/2014 |

(Continued)

OTHER PUBLICATIONS

International Search Report and Written Opinion on PCT/US2020/036809 dated Sep. 14, 2020, 12 pages.
(Continued)

*Primary Examiner* — Christopher J Beccia
(74) *Attorney, Agent, or Firm* — Foley & Lardner LLP

(57) ABSTRACT

An expandable implant including a base member including a top surface, a first end, and a second end, and defining a central cavity positioned between the first end and the second end. The expandable implant further including an adjustable member including a top surface and at least one control channel, wherein the adjustable member is adjustably coupled to the base member and movable between a first, collapsed position, and a second, expanded position, a control shaft received by the base member, wherein manipulation of the control shaft causes relative movement of the adjustable member relative to the base member, and at least one control member coupled to the control shaft and received by the control channel, wherein manipulation of the control shaft causes the control member to translate along the control channel.

21 Claims, 47 Drawing Sheets

Related U.S. Application Data a continuation-in-part of application No. 15/645,179, filed on Jul. 10, 2017, now Pat. No. 10,154,911.

(52) U.S. Cl.
CPC ............... *A61F 2002/30556* (2013.01); *A61F 2002/30579* (2013.01); *A61F 2002/30904* (2013.01); *A61F 2002/443* (2013.01)

(56) References Cited

U.S. PATENT DOCUMENTS

| | | | |
|---|---|---|---|
| 4,863,476 A | 9/1989 | Shepperd | |
| 5,098,435 A | 3/1992 | Stednitz et al. | |
| 5,390,683 A | 2/1995 | Pisharodi | |
| 5,645,599 A | 7/1997 | Samani | |
| 5,658,335 A | 8/1997 | Allen | |
| 5,658,337 A | 8/1997 | Kohrs et al. | |
| 5,836,948 A | 11/1998 | Zucherman et al. | |
| 5,860,977 A | 1/1999 | Zucherman et al. | |
| 5,876,404 A | 3/1999 | Zucherman et al. | |
| 6,048,342 A | 4/2000 | Zucherman et al. | |
| 6,068,630 A | 5/2000 | Zucherman et al. | |
| 6,074,390 A | 6/2000 | Zucherman et al. | |
| 6,126,689 A | 10/2000 | Brett | |
| 6,176,882 B1 | 1/2001 | Biedermann et al. | |
| 6,183,471 B1 | 2/2001 | Zucherman et al. | |
| 6,190,387 B1 | 2/2001 | Zucherman et al. | |
| 6,235,030 B1 | 5/2001 | Zucherman et al. | |
| 6,290,724 B1 | 9/2001 | Marino | |
| 6,375,682 B1 | 4/2002 | Fleischmann et al. | |
| 6,409,766 B1 | 6/2002 | Brett | |
| 6,451,019 B1 | 9/2002 | Zucherman et al. | |
| 6,491,724 B1 | 12/2002 | Ferree | |
| 6,494,883 B1 | 12/2002 | Ferree | |
| 6,537,320 B1 | 3/2003 | Michelson | |
| 6,648,917 B2 | 11/2003 | Gerbec et al. | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,773,460 B2 | 8/2004 | Jackson | |
| 6,796,983 B1 | 9/2004 | Zucherman et al. | |
| 7,048,736 B2 | 5/2006 | Robinson et al. | |
| 7,101,375 B2 | 9/2006 | Zucherman et al. | |
| 7,217,291 B2 | 5/2007 | Zucherman et al. | |
| 7,250,055 B1 | 7/2007 | Vanderwalle | |
| 7,621,950 B1 | 11/2009 | Globerman et al. | |
| 7,695,513 B2 | 4/2010 | Zucherman et al. | |
| 7,731,751 B2 | 6/2010 | Butler et al. | |
| 7,824,427 B2 | 11/2010 | Perez-Cruet et al. | |
| 7,879,098 B1 | 2/2011 | Simmons, Jr. | |
| 7,959,675 B2 | 6/2011 | Gately | |
| 8,016,861 B2 | 9/2011 | Mitchell et al. | |
| 8,048,117 B2 | 11/2011 | Zucherman et al. | |
| 8,071,007 B1 | 12/2011 | Teoh et al. | |
| 8,105,382 B2 | 1/2012 | Olmos et al. | |
| 8,231,656 B2 | 7/2012 | Lee et al. | |
| 8,241,330 B2 | 8/2012 | Lamborne et al. | |
| 8,241,364 B2 | 8/2012 | Hansell et al. | |
| 8,303,663 B2 | 11/2012 | Jimenez et al. | |
| 8,343,190 B1 | 1/2013 | Mueller et al. | |
| 8,353,963 B2 | 1/2013 | Glerum | |
| 8,382,801 B2 | 2/2013 | Lamborne et al. | |
| 8,454,706 B2 | 6/2013 | De Beaubien | |
| 8,506,629 B2 | 8/2013 | Weiland | |
| 8,597,360 B2 | 12/2013 | McLuen et al. | |
| 8,641,764 B2 | 2/2014 | Gately | |
| 8,690,883 B2 | 4/2014 | Collins et al. | |
| 8,821,506 B2 | 9/2014 | Mitchell | |
| 8,845,728 B1 | 9/2014 | Abdou | |
| 8,894,711 B2 | 11/2014 | Varela | |
| 8,894,712 B2 | 11/2014 | Varela | |
| 8,974,505 B2 | 3/2015 | Sawa et al. | |
| 9,034,041 B2 | 5/2015 | Wolters et al. | |
| 9,044,284 B2 | 6/2015 | Sweeney | |
| 9,101,487 B2 | 8/2015 | Petersheim | |
| 9,198,772 B2 | 12/2015 | Weiman | |
| 9,204,922 B2 | 12/2015 | Hooven | |
| 9,204,972 B2 | 12/2015 | Weiman et al. | |
| 9,216,098 B2 | 12/2015 | Trudeau et al. | |
| 9,295,562 B2 | 3/2016 | Lechmann et al. | |
| 9,492,286 B2 | 11/2016 | Biedermann et al. | |
| 9,532,883 B2 | 1/2017 | McLuen et al. | |
| 9,554,918 B2 | 1/2017 | Weiman | |
| 9,610,174 B2 | 4/2017 | Wang et al. | |
| 9,622,879 B2 | 4/2017 | Taylor et al. | |
| 9,770,343 B2 | 9/2017 | Weiman | |
| 9,801,733 B2 | 10/2017 | Wolters et al. | |
| 9,968,462 B2 | 5/2018 | Weiman | |
| 10,004,607 B2 | 6/2018 | Weiman et al. | |
| 10,154,911 B2 * | 12/2018 | Predick | A61F 2/4455 |
| 10,383,741 B2 | 8/2019 | Butler et al. | |
| 10,426,632 B2 | 10/2019 | Butler et al. | |
| 2002/0010472 A1 | 1/2002 | Kuslich et al. | |
| 2002/0128716 A1 | 9/2002 | Cohen et al. | |
| 2003/0040746 A1 | 2/2003 | Mitchell et al. | |
| 2003/0236520 A1 | 12/2003 | Lim et al. | |
| 2004/0073213 A1 | 4/2004 | Serhan et al. | |
| 2004/0153156 A1 | 8/2004 | Cohen et al. | |
| 2004/0167625 A1 | 8/2004 | Beyar et al. | |
| 2004/0225292 A1 | 11/2004 | Sasso et al. | |
| 2005/0033437 A1 | 2/2005 | Bao et al. | |
| 2005/0070911 A1 | 3/2005 | Carrison et al. | |
| 2005/0107800 A1 | 5/2005 | Frankel et al. | |
| 2005/0119747 A1 | 6/2005 | Fabris Monterumici | |
| 2005/0131536 A1 | 6/2005 | Eisermann et al. | |
| 2005/0143827 A1 | 6/2005 | Globerman et al. | |
| 2005/0222681 A1 | 10/2005 | Richley et al. | |
| 2005/0228391 A1 | 10/2005 | Levy et al. | |
| 2005/0261769 A1 | 11/2005 | Moskowitz et al. | |
| 2005/0278036 A1 | 12/2005 | Leonard et al. | |
| 2006/0036258 A1 | 2/2006 | Zucherman et al. | |
| 2006/0084988 A1 | 4/2006 | Kim | |
| 2006/0089718 A1 | 4/2006 | Zucherman et al. | |
| 2006/0095136 A1 | 5/2006 | McLuen | |
| 2006/0189999 A1 | 8/2006 | Zwirkoski | |
| 2006/0241601 A1 | 10/2006 | Trautwein et al. | |
| 2006/0264938 A1 | 11/2006 | Zucherman et al. | |
| 2007/0142915 A1 | 6/2007 | Altarac et al. | |
| 2008/0114456 A1 | 5/2008 | Dewey et al. | |
| 2008/0140085 A1 | 6/2008 | Gately et al. | |
| 2008/0140207 A1 | 6/2008 | Olmos et al. | |
| 2008/0161818 A1 | 7/2008 | Kloss et al. | |
| 2008/0177391 A1 | 7/2008 | Mitchell et al. | |
| 2008/0183211 A1 | 7/2008 | Lamborne et al. | |
| 2008/0312741 A1 | 12/2008 | Lee et al. | |
| 2009/0062915 A1 | 3/2009 | Kohm et al. | |
| 2010/0211176 A1 | 8/2010 | Greenhalgh | |
| 2010/0241167 A1 | 9/2010 | Taber et al. | |
| 2011/0022090 A1 | 1/2011 | Gordon et al. | |
| 2011/0066186 A1 | 3/2011 | Boyer et al. | |
| 2011/0071635 A1 | 3/2011 | Zhang et al. | |
| 2011/0077738 A1 | 3/2011 | Ciupik et al. | |
| 2011/0144692 A1 | 6/2011 | Saladin et al. | |
| 2011/0172709 A1 | 7/2011 | Lyons et al. | |
| 2011/0184468 A1 | 7/2011 | Metcalf et al. | |
| 2011/0224731 A1 | 9/2011 | Smisson et al. | |
| 2011/0282453 A1 | 11/2011 | Greenhalgh et al. | |
| 2011/0319997 A1 | 12/2011 | Glerum et al. | |
| 2012/0010717 A1 | 1/2012 | Spann | |
| 2012/0016418 A1 | 1/2012 | Chin et al. | |
| 2012/0059474 A1 | 3/2012 | Weiman | |
| 2012/0109203 A1 | 5/2012 | Dryer et al. | |
| 2012/0185049 A1 | 7/2012 | Varela | |
| 2012/0221051 A1 | 8/2012 | Robinson | |
| 2012/0330422 A1 | 12/2012 | Weiman | |
| 2013/0085572 A1 | 4/2013 | Glerum et al. | |
| 2013/0103156 A1 | 4/2013 | Packer et al. | |
| 2013/0116793 A1 | 5/2013 | Kloss | |
| 2013/0158664 A1 | 6/2013 | Palmatier et al. | |
| 2013/0158668 A1 | 6/2013 | Nichols et al. | |
| 2013/0158669 A1 * | 6/2013 | Sungarian | A61F 2/447 623/17.16 |
| 2013/0211526 A1 | 8/2013 | Alheidt et al. | |
| 2014/0148904 A1 | 5/2014 | Robinson | |

(56) References Cited

U.S. PATENT DOCUMENTS

| | | |
|---|---|---|
| 2014/0236296 A1 | 8/2014 | Wagner et al. |
| 2014/0277461 A1 | 9/2014 | Nebosky et al. |
| 2014/0277473 A1 | 9/2014 | Perrow |
| 2014/0277500 A1 | 9/2014 | Logan et al. |
| 2014/0343678 A1 | 11/2014 | Suddaby et al. |
| 2015/0100128 A1 | 4/2015 | Glerum et al. |
| 2015/0112438 A1 | 4/2015 | McLean |
| 2015/0173917 A1 | 6/2015 | Radcliffe et al. |
| 2015/0374507 A1 | 12/2015 | Wolters et al. |
| 2016/0051377 A1 | 2/2016 | Weiman et al. |
| 2016/0242927 A1 | 8/2016 | Seifert et al. |
| 2016/0361177 A1* | 12/2016 | Biedermann ......... A61F 2/4465 |
| 2017/0056197 A1 | 3/2017 | Weiman et al. |
| 2017/0216036 A1 | 8/2017 | Cordaro |
| 2017/0224504 A1 | 8/2017 | Butler et al. |
| 2017/0224505 A1 | 8/2017 | Butler et al. |
| 2017/0258605 A1 | 9/2017 | Blain et al. |
| 2017/0281432 A1 | 10/2017 | Glerum et al. |
| 2017/0333198 A1 | 11/2017 | Robinson |
| 2017/0348116 A1 | 12/2017 | Weiman |
| 2018/0325693 A1 | 11/2018 | Weiman et al. |
| 2019/0374348 A1 | 12/2019 | Butler et al. |

FOREIGN PATENT DOCUMENTS

| | | |
|---|---|---|
| EP | 3 031 424 A1 | 6/2016 |
| GB | 0 284 462 A | 2/1928 |
| WO | WO-2006/102485 | 9/2006 |
| WO | WO-2006/105437 A2 | 10/2006 |
| WO | WO-2009/124269 | 10/2009 |
| WO | WO-2014/165319 A1 | 10/2014 |
| WO | WO-2016/077610 A1 | 5/2016 |
| WO | WO2016/127139 A1 | 8/2016 |
| WO | WO-2017/027873 A1 | 2/2017 |
| WO | WO-2017/066463 A1 | 4/2017 |
| WO | WO-2018/200507 A1 | 11/2018 |
| WO | WO2019/014139 A1 | 1/2019 |
| WO | WO-2019/014139 A1 | 1/2019 |

OTHER PUBLICATIONS

Search Report for International Application No. PCT/US2018/041306, dated Sep. 28, 2018, 12 pages.
Bacfuse® Spinous Process Fusion Plate Surgical Technique, 2011, Pioneer Surgical, 12 pages.
Extended European Search Report for European Application No. 14159101.6, dated Jun. 18, 2014, 6 pages.
Extended European Search Report for European Application No. 16169890.7, dated Oct. 21, 2016, 7 pages.
International Preliminary Report on Patentability tor Application No. PCT/US06/12060 dated Sep. 30, 2007, 3 pages.
International Search Report and Written Opinion for International Application No. PCT/US2012/057324, dated Dec. 20, 2012, 10 pages.
International Search Report for International Application No. PCT/US2018/029120, dated Jun. 28, 2018, 17 pages.
International Search Report for International Application No. PCT/US2018/029149, dated Jun. 25, 2018, 13 pages.
Written Opinion of the International Searching Authority for Application No. PCT/US06/12060, dated Apr. 5, 2007, 3 pages.
International Search Report on PCT/US2020/037020, dated Sep. 29, 2020, 20 pages.
International Search Report for International Application No. PCT/US2019/037275, dated Sep. 24, 2019, 12 pages.

* cited by examiner

EXPANDABLE IMPLANT ASSEMBLY

CROSS-REFERENCE TO RELATED PATENT APPLICATIONS

The present application is a continuation-in-part of International Patent Application No. PCT/US2018/041306, filed Jul. 9, 2018, which is a continuation-in-part of U.S. application Ser. No. 15/645,179, filed Jul. 10, 2017, both of which are incorporated by reference herein.

BACKGROUND

The present disclosure relates to expandable implants and devices, including spinal interbody and intravertebral body devices, and vertebral interbody and intravertebral devices that are expandable after spinal placement thereof.

Fusion cages, as well as other types of implants, bodies and/or devices, are frequently utilized in spinal surgery inside a vertebra (intravertebral) and/or between vertebrae of a patient (interbody), or adjacent other bone bodies. With interbody devices, one or more such spinal bodies are placed between vertebrae to provide support and promote fusion between adjacent vertebrae where such is necessary due to disease, injury, general deterioration or congenital problem. With intravertebral devices, one or more spinal bodies are placed within a vertebra. Spinal devices, such as fusion cages and/or the like, are inserted into a spinal space either anteriorly, posteriorly, laterally or posteriolaterally.

A problem with most spinal interbody and intravertebral devices is that they are static in size and difficult to position. This poses various problems with their use and/or implantation. Particularly, static sized spinal devices are fairly large in order to properly bridge the gap between adjacent vertebrae. This large size does not lend itself to microsurgery, arthroscopic surgery or the like. Furthermore, spinal devices that are difficult to position require more invasive surgery techniques, and longer surgery time to implant. This complicated positioning does not lend itself to minimally invasive surgery or even outpatient procedures.

Devices are now being made that are expandable and more easily positioned. Expandable interbody devices allow the device to be initially smaller than traditional non-expandable (static) interbody devices such that expandable interbody devices may be more easily inserted or implanted into the vertebral space. Moreover, expandable devices allow the surgeon to set the amount of expansion necessary for the particular patient rather than the static device dictating the spacing. Furthermore, expandable devices can include attachment points for manipulation tools. Expandable devices integrated with a manipulation tool allows the surgeon to more easily position and expand the implant rather than using several bulkier tools.

SUMMARY

One embodiment relates to an expandable implant including a base member including a top surface, a first end, and a second end, and defining a central cavity positioned between the first end and the second end. The expandable implant further including an adjustable member including a top surface and at least one control channel, wherein the adjustable member is adjustably coupled to the base member and movable between a first, collapsed position, and a second, expanded position, a control shaft received by the base member, wherein manipulation of the control shaft causes relative movement of the adjustable member relative to the base member, and at least one control member coupled to the control shaft and received by the control channel, wherein manipulation of the control shaft causes the control member to translate along the control channel.

In some embodiments, the at least one control channel including a first control channel and a second control channel, and wherein the at least one control member includes a first control member received in the first control channel and a second control member received in the second control channel. In some embodiments, the first control channel and the second control channel extend in non-parallel directions. In some embodiments, the first control member and the second control member are at least partially rectangular and include a flat portion configured to engage a corresponding flat portion on the adjustable member to prevent rotation of the first control member within the first control channel and the second control member within the second control channel. In some embodiments, manipulation of the control shaft includes rotation, and wherein rotation of the control shaft causes the first and second control members to translate in opposite directions along the control shaft. In some embodiments, a top surface of the adjustable member and a bottom surface of the base member define an implant height of the expandable implant and are configured to engage adjacent portions of bone. In some embodiments, manipulation of the control member changes a height of the implant.

Another embodiment of the present disclosure is an expandable implant including a base member including a central cavity positioned between a first end and a second end of the base member, an adjustable member coupled to the base member and movable between a collapsed position and an expanded position, the adjustable member including at least one guide channel, a control shaft received in the central cavity of the base member, wherein manipulation of the control shaft causes the adjustable member to move between the collapsed position and the expanded position, and at least one guide pin coupled to the base member and received by the guide channel of the adjustable member, wherein the at least one guide pin limits a degree of expansion of the adjustable member relative to the base member.

In some embodiments, the base member has first side, a second side, a first end, and a second end, and wherein the first side and the second side are curved between the first end and the second end. In some embodiments, the first side has a first height and the second side has a second height, and wherein the first height is different than the second height. In some embodiments, the adjustable member has a first side, a second side, a first end, and a second end, and wherein the first side and the second side are curved between the first end and the second end. In some embodiments, the first side has a first height and the second side has a second height, and wherein the first height is different than the second height. In some embodiments, the adjustable member further including at least one control channel. In some embodiments, the expandable implant includes at least one control member received by the control shaft and the control channel, wherein manipulation of the control shaft causes the control member to translate along the control shaft.

Another embodiment of the present disclosure is an expandable implant including a base member including a first side having a first height, a second side having a second height, a first end, and a second end, wherein the first side and the second side are curved between the first end and the second end, an adjustable member coupled to the base member and including a third side having a third height, a fourth side having a fourth height, a third end, and a fourth end, wherein the third side and the fourth side are curved between the third end and the fourth end, and wherein the adjustable member is movable between a collapsed position and an expanded position, and a control shaft rotatably received by the base member, wherein rotation of the control shaft causes the adjustable member to move between the collapsed position and the expanded position, wherein the first height and the second height are different, and wherein the third height and the fourth height are different.

In some embodiments, the adjustable member further comprising at least one control channel. In some embodiments, the expandable implant further includes at least one control member received on the control shaft and by the control channel, wherein rotation of the control shaft causes the control member to translate along the control shaft. In some embodiments, the at least one control channel including a first control channel and a second control channel, and wherein the at least one control member includes a first control member received in the first control channel and a second control member received in the second control channel. In some embodiments, the first control member and the second control member are at least partially rectangular and include a flat portion configured to engage a corresponding flat portion on the adjustable member to prevent rotation of the first control member within the first control channel and the second control member within the second control channel. In some embodiments, rotation of the control shaft causes the first and second control members to translate in opposite directions along the control shaft. In some embodiments, a curvature of the first side is the same as a curvature of the third side and a curvature of the second side is the same as a curvature of the fourth side. In some embodiments, the first side is aligned with the third side and the second side is aligned with the fourth side when the adjustable member is in the collapsed position. In some embodiments, the control shaft is configured to enable a fluid to move between an exterior of the expandable implant and an interior of the expandable implant.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

Figure 1:
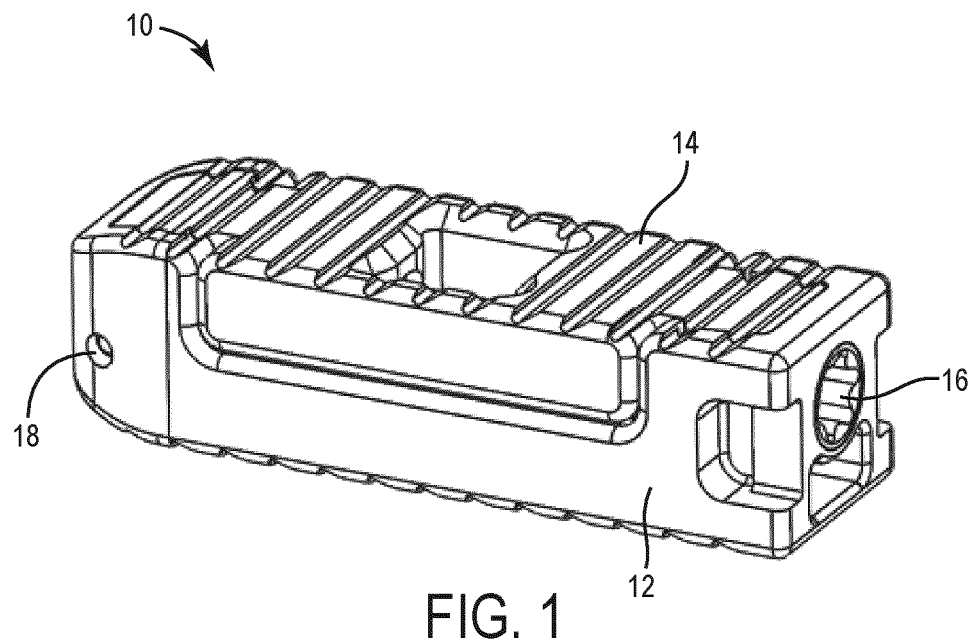
FIG. 1 is perspective view of an expandable implant in a collapsed position according to one embodiment.

Corresponding reference characters indicate corresponding parts throughout the several views. Although the drawings represent embodiments of the disclosure, the drawings are not necessarily to scale and certain features may be exaggerated in order to better illustrate and explain the principles of the present disclosure. The exemplifications set out herein illustrate several embodiments, but the exemplifications are not to be construed as limiting the scope of the disclosure in any manner.

DETAILED DESCRIPTION

The present disclosure relates to expandable and/or dynamic implants, including, but not limited to, interbody (between adjacent vertebrae), intravertebral-body (inside the vertebrae) and/or spinal stabilization devices that may or may not be used as interbody fusion cages or devices, interbody/intravertebral bodies/body stabilization devices and/or the like (e.g., spinal device(s)) for providing support, stabilization and/or promoting bone growth between or inside vertebrae or other portions of bone that have been destabilized or otherwise due to injury, illness and/or the like. Particularly, the present disclosure provides various versions of dynamic (expandable and/or expandable and retractable) interbody/intravertebral body devices that are usable in a spinal column or other areas of a human.

Various embodiments disclosed herein are directed to expandable implants that are implantable between adjacent bodies of bone. For example, the implant may be implanted or inserted into a human spine adjacent upper and lower vertebrae of the spine. According to various exemplary embodiments, the components of the implants disclosed herein may be made of any suitable material(s), including a variety of metals, plastics, composites, or other suitable bio-compatible materials. In some embodiments, one or more components of the implants disclosed herein may be made of the same material, while in other embodiments, different materials may be used for different components of the various implants.

Referring now to FIGS. 1-9C, an expandable implant 10 is shown according to an exemplary embodiment. Implant 10 is usable, for example, between and/or within vertebral bodies of the spine, and may share many of the features of the other inter/intra-body implants discussed elsewhere herein. It should be understood that implant 10 may in some embodiments be usable in other portions of the body in addition to the spine, and all such applications are to be understood to be within the scope of the present disclosure.

Figure 2:
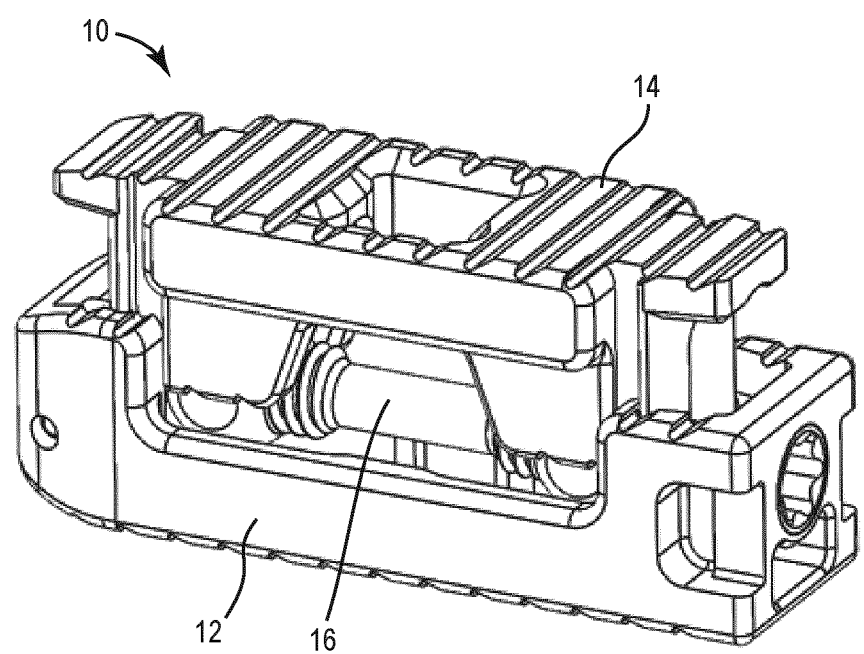
FIG. 2 is a perspective view of the implant of FIG. 1 in an expanded position according to one embodiment.
Figure 3:
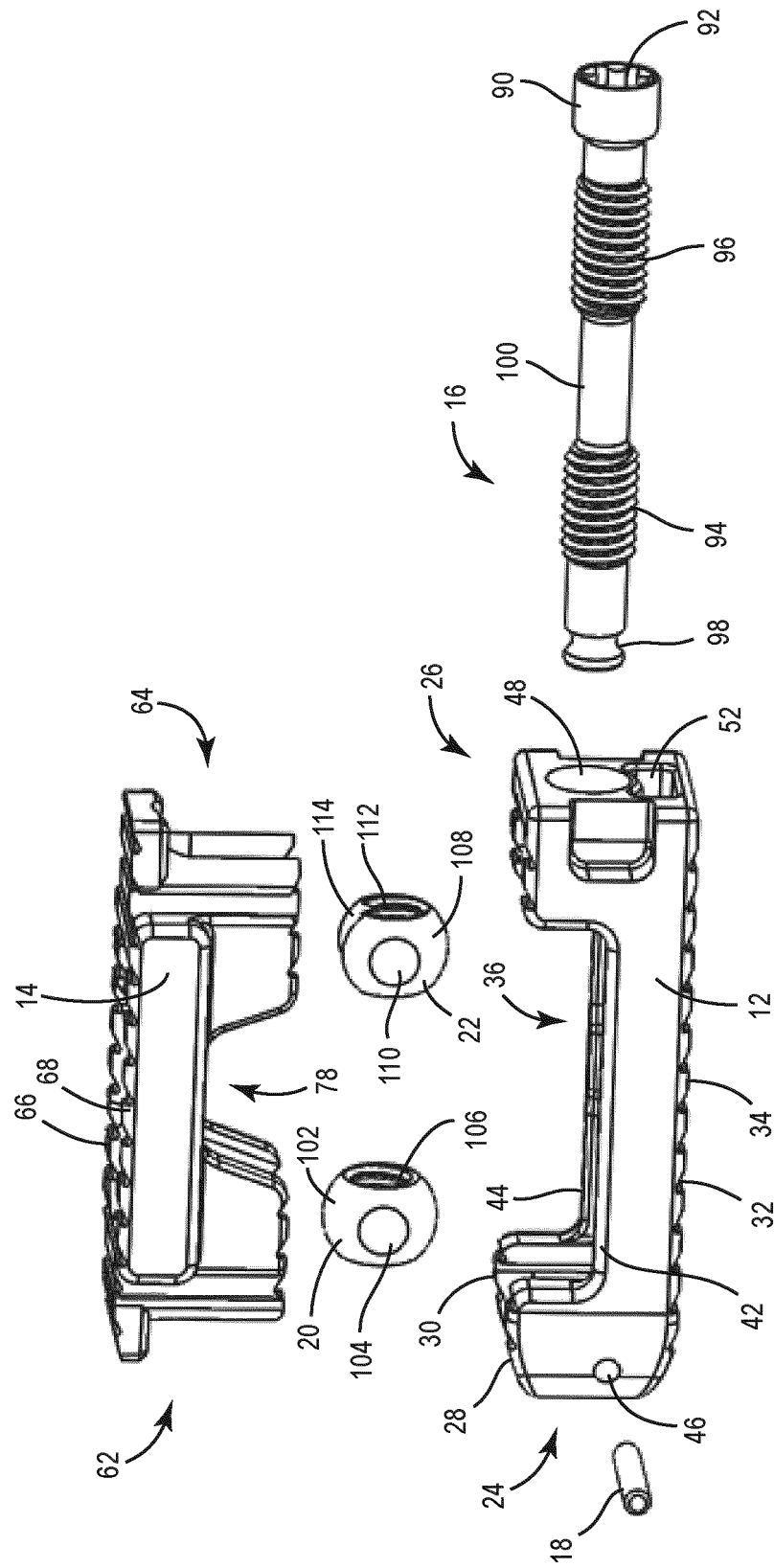
FIG. 3 is an exploded view of the implant of FIG. 1 according to one embodiment.

According to an exemplary embodiment, implant 10 includes a base member 12 and an adjustable member 14 adjustably coupled to the base member 12. A control shaft 16 is received by the base member 12 and is retained by a retention pin 18 passing through a portion of the base member 12. A first control member 20 and a second control member 22 are received on the control shaft 16 and are movable along the control shaft 16 to adjust a position of the adjustable member 14 between a collapsed position, as shown in FIG. 1, and an expanded position, as shown in FIG. 2.

Figure 6:
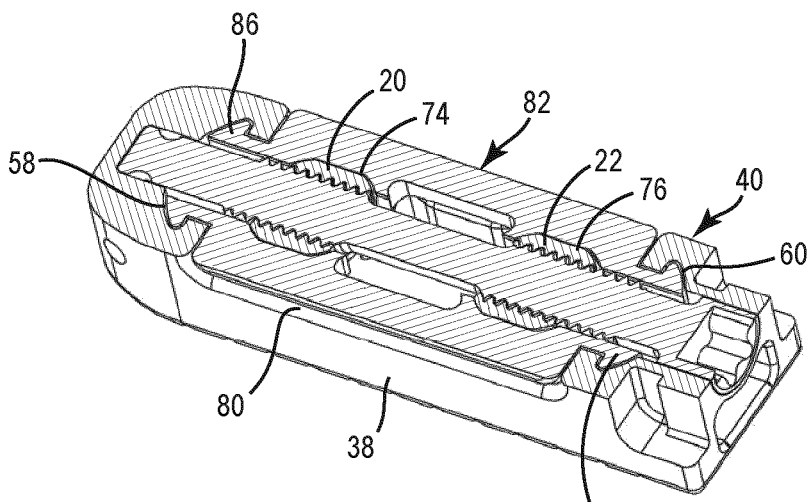
FIG. 6 is a top cross-sectional view of the implant of FIG. 1 according to one embodiment.
Figure 7:
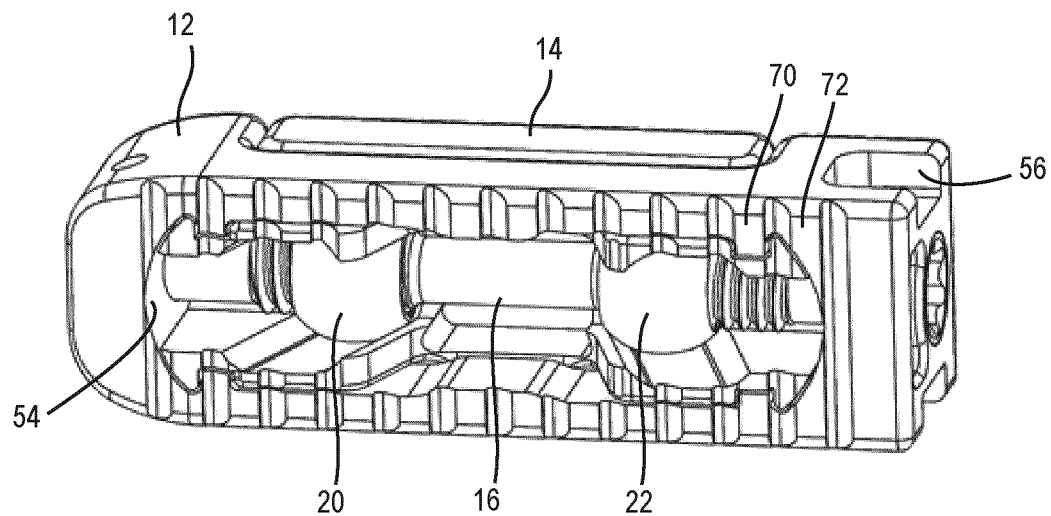
FIG. 7 is a bottom perspective view of the implant of FIG. 1 in a collapsed position according to one embodiment.
Figure 8:
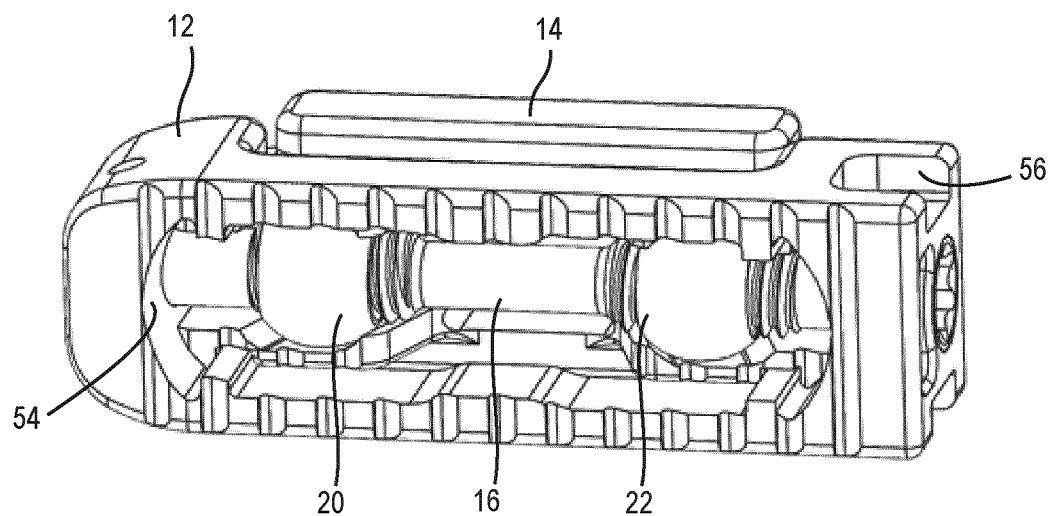
FIG. 8 is a bottom perspective view of the implant of FIG. 1 in an expanded position according to one embodiment.

In one embodiment, the base member 12 includes a front or first end 24, a rear or second end 26, and a central cavity 36 disposed between the first end 24 and the second end 26. The base member 12 further includes a top surface 28 having ridges or projections 30 formed by corresponding grooves, a bottom surface 32 opposite the top surface 28 and having ridges or projections 34 formed by corresponding grooves, a first side 38, and a second side 40. The projections 30, 34 are configured to engage adjacent portions of bone. The first side 38 defines a first side recess 42, and the second side 40 defines a second side recess 44. A pin aperture 46 extends through one or both of first side 38 and second side 40 and is configured to receive the retention pin 18 (e.g., in a press fit or other manner). The second end 26 of the base member 12 includes a control bore 48 configured to receive a first portion of the control shaft 16. The first end 24 of the base member 12 includes a control counterbore 50 (see FIG. 4) configured to receive a second portion of the control shaft 16. As shown in FIG. 6, in some embodiments, the first end 24 of the base member 12 further includes a dovetail recess 58, and the second end 26 of the base member 12 further includes a dovetail recess 60.

In one embodiment, the adjustable member 14 includes a front or first end 62, a rear or second end 64, and a central recess or cavity 78 positioned between the first end 62 and the second end 64. A top cavity 84 (see FIG. 5) in the adjustable member 14 extends to the central cavity 78. The adjustable member 14 further includes a top surface 66 having ridges or projections 68 formed by corresponding grooves, a bottom surface 70 including ridges or projections 72 (see FIG. 8) formed by corresponding grooves, a first side portion 80, and a second side portion 82. In some embodiments, the first and second side portions 80, 82 have shapes generally corresponding to the shapes of the first and second side recesses 42, 44 of base member 12. In other embodiments, the first and second side portions 80, 82 have shapes differing from the shapes of the first and second side recesses 42, 44 of the base member 12. The first end 62 of the adjustable member 14 further includes a dovetail projection 86, and the second end 64 of the adjustable member 14 further includes a dovetail projection 88.

Figure 4:
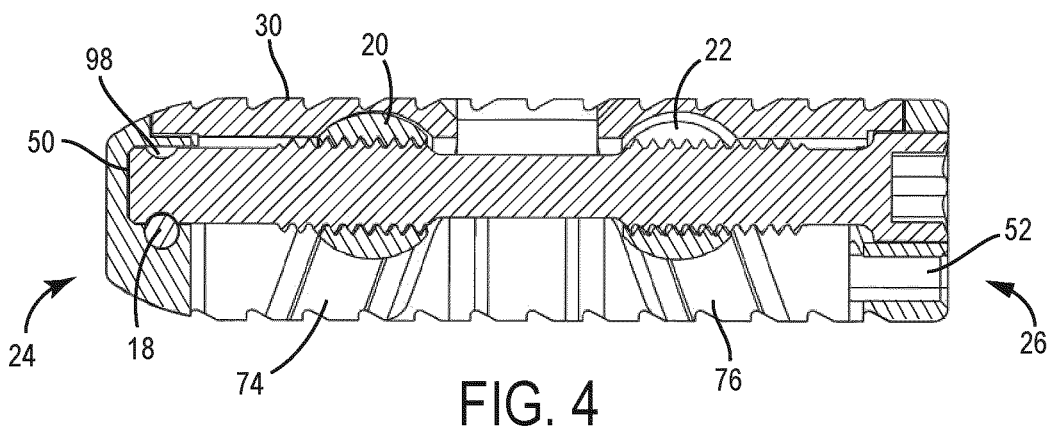
FIG. 4 is a side cross-sectional view of the implant of FIG. 1 in a collapsed position according to one embodiment.
Figure 5:
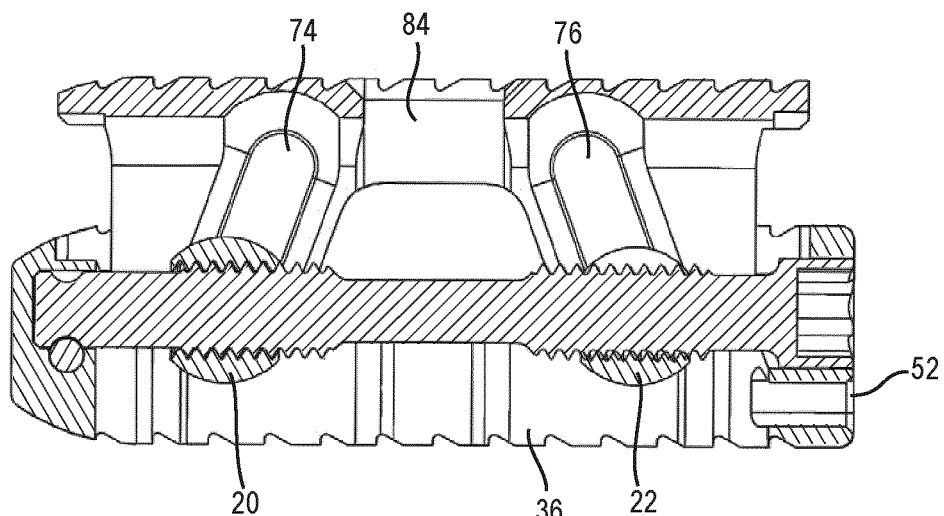
FIG. 5 is a side cross-sectional view of the implant of FIG. 1 in an expanded position according to one embodiment.

Referring to FIGS. 4-6, in one embodiment, the adjustable member 14 includes one or more control channels, such as a first control channel 74 and a second control channel 76. The first control channel 74 receives the first control member 20, and the second control channel 76 receives the second control member 22. In some embodiments, the control members 20, 22 are received in the control channels 74, 76 in a sliding manner such that the control members 20, 22 are able to translate within the control channels 74, 76. In further embodiments, each control channel has a shape such that the control channel surrounds the control member and at least partially corresponds in shape to the control member.

Referring back to FIG. 3, the control shaft 16 includes a head portion 90, a tool port 92 disposed within the head portion 90, and a retention groove 98 located at an end opposite the head portion 90. In some embodiments, the control shaft 16 further includes a first control thread 94 and a second control thread 96. A non-threaded portion 100 may be located between the first control thread 94 and the second control thread 96.

The first control member 20 includes a body 102, one or more flat portions 104, and a first internal thread 106. The second control member 22 includes a body 108, one or more flat portions 110, and a second internal thread 112. In some embodiments, the second control member 22 further includes a slotted portion 114 configured to enable passing the second control member 22 over a portion (e.g., non-threaded portion 100) of the control shaft 16. The first control member 20 and the second control member 22 move or translate both along the control shaft 16 and within or on the first control channel 74 and the second control channel 76.

Referring back to FIGS. 1 and 2, implant 10 is movable between a first, collapsed position, as shown in FIG. 1, to a second, expanded position, shown in FIG. 2. In the first position, the adjustable member 14 is received within the central cavity 36 of the base member 12. The dovetail projections 86, 88 on the adjustable member 14 are received within the dovetail recesses 58, 60 in the base member 12 (see FIG. 6). In some embodiments, the projections and recesses have a relatively close fit to enable proper alignment between the adjustable member 14 and the base member 12, while in other embodiments, the projections and recesses have a relatively loose fit to enable a desired angular offset between the adjustable member 14 and the base member 12.

Referring to FIGS. 3-6, the control shaft 16 is received by the base member 12 such that the retention groove 98 is positioned with the first end 24 of the base member 12 and the head portion 90 is positioned within the second end 26 of the base member 12. In one embodiment, the control shaft 16 is rotatable within the base member 12, and the retention pin 18 extends through the first end 24 and into the retention groove 98 of the control shaft 16 to enable rotation of the control shaft 16 while inhibiting translation of the control shaft 16 relative to the base member 12. The first control member 20 is received on the first control thread 94 of the control shaft 16, and the second control member 22 is received on the second control thread 96 of the control shaft 16. To facilitate assembly of implant 10, in some embodiments, the slot 114 enables passage of the second control member 22 over the non-threaded portion 100 of the control shaft 16 and subsequent threading of the second control member 22 onto the second control thread 96.

In one embodiment, the first control thread 94 and the second control thread 96 are threaded in opposite manners (e.g., left-handed and right-handed), such that upon rotation of the control shaft 16, the control members 20, 22 move in opposite directions along the control shaft 16. For example, the control shaft may be configured that rotation of the control shaft 16 in a first direction (e.g., clockwise) causes the first and second control members 20, 22 to move toward each other, and rotation of the control shaft 16 in a second direction (e.g., counter-clockwise) causes the first and second control member 20, 22 to move away from each other.

As shown in FIGS. 4 and 5, as the control members 20, 22 move along the control shaft 16, the control members 20, 22 further move within the control channels 74, 76, thereby causing relative movement of the adjustable member 14 and the base member 12. For example, FIGS. 4 and 5 show the control members 20, 22 moving away from each other along the control shaft 16. As the control members 20, 22 translate along the control shaft 16, the adjustable member 14 is moved upward or downward due to the angled shape of the first and second control channels 74, 76. The rate of movement of the control members 20, 22, and therefore the adjustable member 14, can be adjusted by modifying the slope of the control channels 74, 76 relative to the control shaft 16.

Figure 9A:
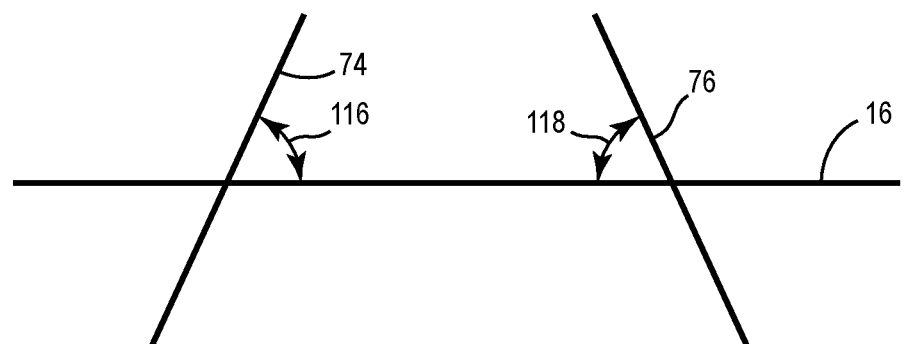
FIG. 9A is a schematic view of a control scheme usable with the implants disclosed herein according to one embodiment.
Figure 9B:
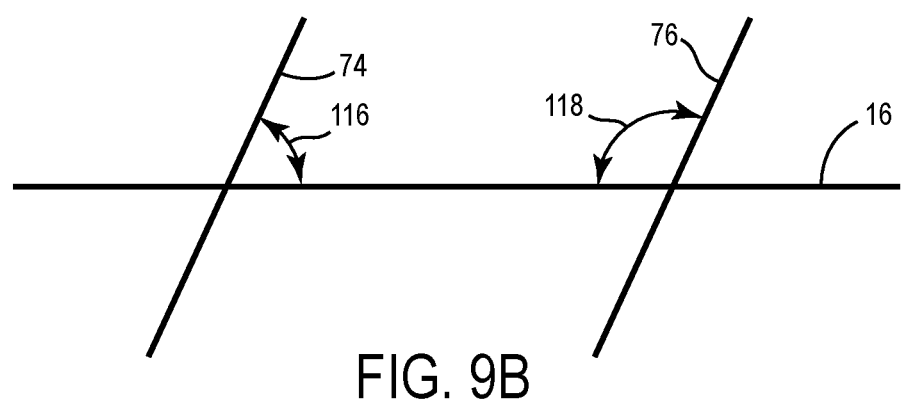
FIG. 9B is a schematic view of a control scheme usable with the implants disclosed herein according to another embodiment.
Figure 9C:
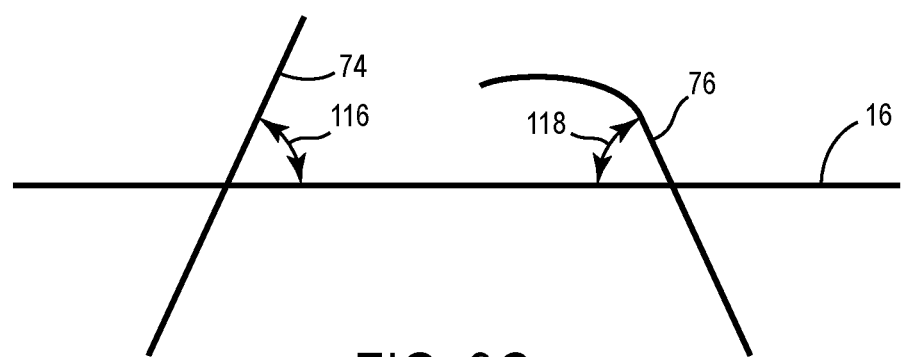
FIG. 9C is a schematic view of a control scheme usable with the implants disclosed herein according to another embodiment.

For example, referring to FIGS. 9A-9C, schematic representations of the control shaft 16, the first control channel 74, and the second control channel 76 are shown according to various alternative embodiments. The first control channel 74 extends at a first angle 116 relative to the control shaft 16, and the second control channel 76 extends at a second angle 118 relative to the control shaft 16. The first and second angles 116, 118 define the rate at which first control member 20 and second control member 22 cause corresponding movement (e.g., expansion) of the first and second ends 62, 64 of the adjustable member 14 relative to the base member 12. As shown in FIG. 9A, in some embodiments, the first angle 116 and second angle 118 are approximately the same, and the control channels 74, 76 define linear paths, such that the rates of movement of the first and second ends 62, 64 of the adjustable member 14 are substantially the same and constant (assuming a constant rate of rotation of the control shaft 16). As shown in FIG. 9B, in some embodiments, rather than being angled toward each other in an upward direction, the first and second control channels 74, 76 may extend in a parallel manner or be configured to extend upward at angles in the same general direction. In yet further embodiments, one or both of the control channels 74, 76 may define a non-linear channel. For example, as shown in FIG. 9C, the second control channel 76 defines a curved path, thereby providing a changing rate of movement of the second end 64 of adjustable member 14. In further alternative embodiments, angles 116, 118 may differ from each other to provide different amounts of movement and to suit a particular application.

Providing differing configurations for the first control channel 74 and the second control channel 76 enables customization of the characteristics of the implant 10 in the second, expanded position. For example, the control channels 74, 76 may be configured such that in a fully expanded position of implant 10, one of the first end 62 and the second end 64 of the adjustable member 14 is expanded to a greater degree than the opposing end. An example of such a configuration is reflected in FIG. 9C, and shown in greater detail with the embodiment of FIGS. 27-34. Other configurations of the first and second control channels 74, 76 are possible according to various alternative embodiments.

In use, implant 10 is positioned within a desired space (e.g., between adjacent portions of bone) while in the first, collapsed position, as shown in FIG. 1. To position implant 10, an appropriate tool may be used to engage tool recesses 56 and manipulate implant 10 into a desired position. Once in a desired position, a subsequent tool may be utilized to engage tool port 92 and rotate control shaft 16 to move adjustable member 14 to a desired degree of expansion. It should be noted that based on a particular application, the adjustable member 14 may be utilized in a fully collapsed position, a fully expanded position, or any intermediate position therebetween. Once implant 10 is properly positioned and expanded to a desired height, bone graft material may be delivered by way of, for example, access aperture 52 and placed into central cavity 36. The various apertures in and through the base member 12 and adjustable member 14 may in some embodiments facilitate the growth of bone material in and around implant 10 to further stabilize the device.

It should be noted that implant 10 may share various features with the other implants described herein, and be made of the same, similar, or different materials. For example, various components of implant 10 may be made of metal, plastic, composites, or other suitable bio-compatible materials. Further, implant 10 may be usable in connection with the spine or other parts of the body.

Referring now to FIGS. 10-15, an expandable implant 210 is shown according to an exemplary embodiment. Implant 210 may share many of the features of the other inter/intra-body implants discussed elsewhere herein. All such combinations of features are to be understood to be within the scope of the present disclosure. Implant 110 is generally similar to implant 10 in structure and function except that, while implant 10 expands to vary an implant height, implant 210 expands to vary an implant width.

Figure 10:
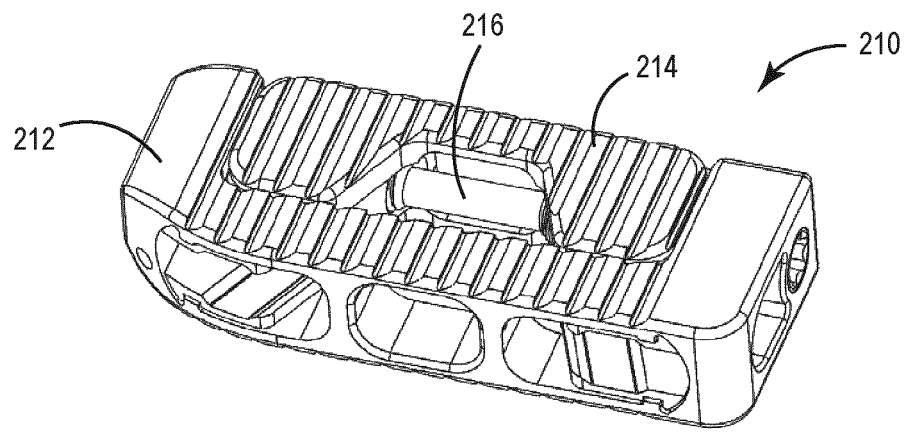
FIG. 10 is a perspective view of an expandable implant in a collapsed position according to another embodiment.
Figure 11:
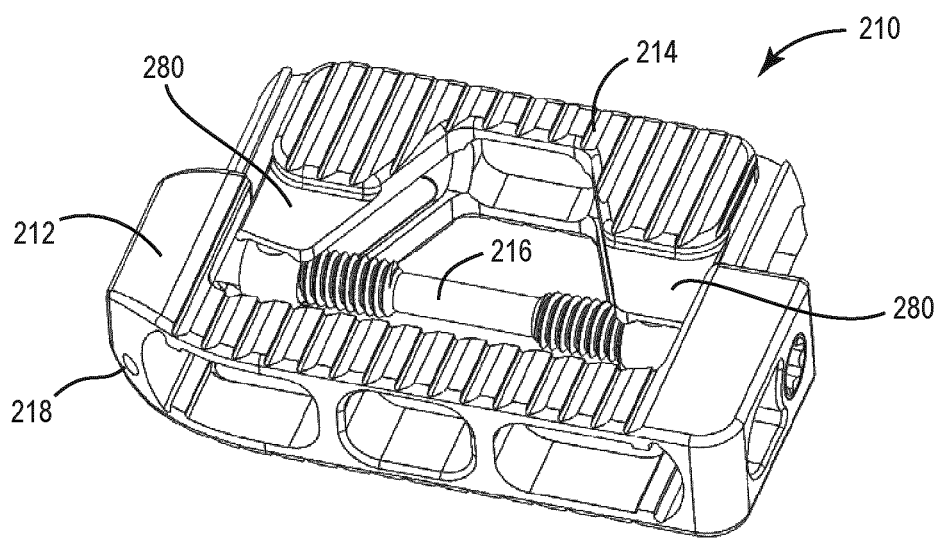
FIG. 11 is a perspective view of the implant of FIG. 10 in an expanded position according to one embodiment.
Figure 12:
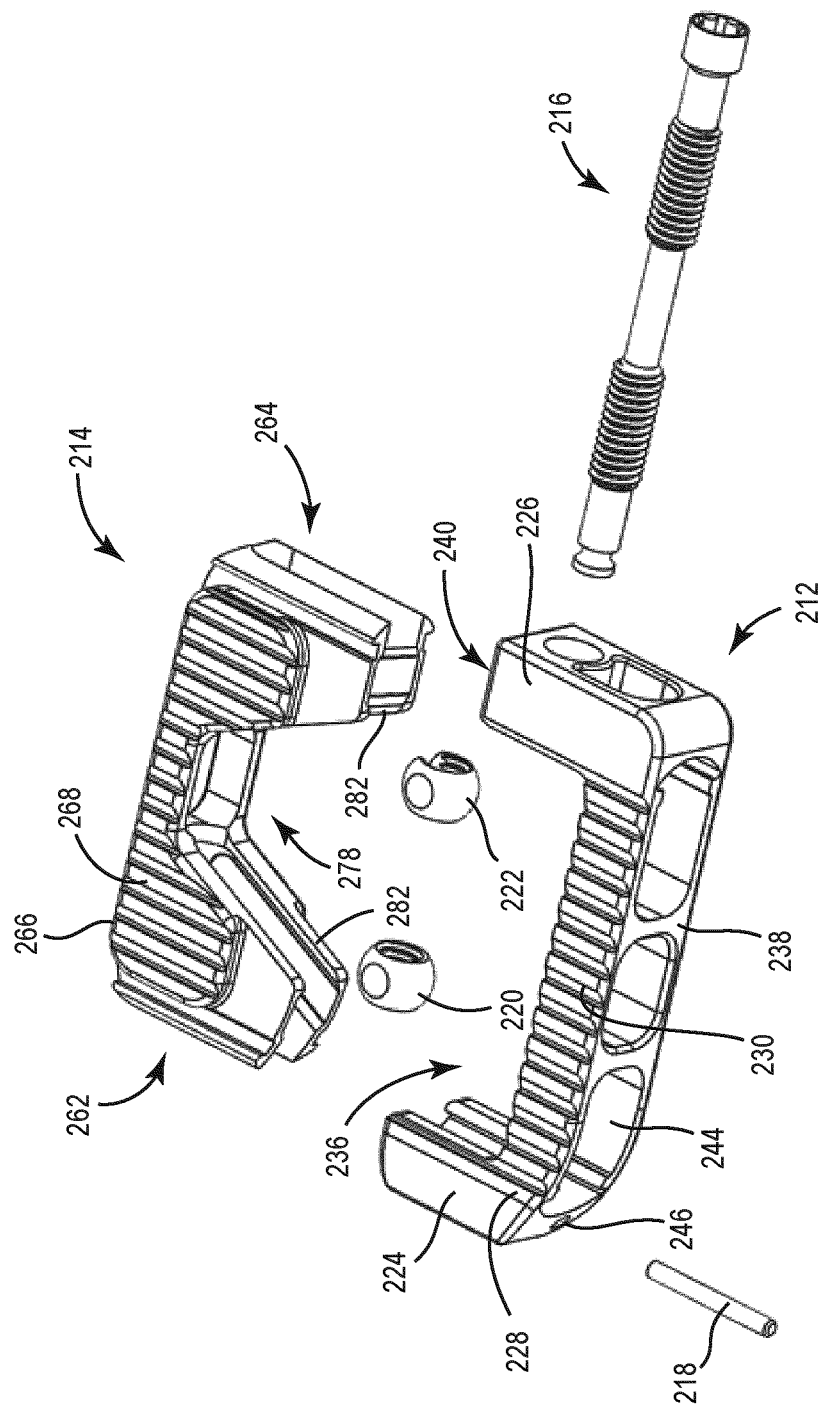
FIG. 12 is an exploded view of the implant of FIG. 10 according to one embodiment.

Implant 210 includes a base member 212 and an adjustable member 214 adjustably coupled to the base member 212. A control shaft 216 is received by the base member 212 and is retained by a retention pin 218 passing through a portion of the base member 212. A first control member 220 and a second control member 222 are received on the control shaft 216 and are movable along the control shaft 216 to adjust a position of the adjustable member 214 between a collapsed position, as shown in FIG. 10, and an expanded position, as shown in FIG. 11.

In one embodiment, the base member 212 includes a front or first end 224, a rear or second end 226, and a central cavity 236 disposed between the first end 224 and the second end 226. The base member 212 further includes a top surface 228 having ridges or projections 230 formed by corresponding grooves, a bottom surface 232 opposite the top surface 228 and having ridges or projections 234 formed by corresponding grooves, a first side 238, and a second side 240. The projections 230, 234 are configured to engage adjacent portions of bone. The first side 238 defines a plurality of recesses 244. A pin aperture 246 extends through one or both of the first side 238 and the second side 240 and is configured to receive the retention pin 218 (e.g., in a press fit or other manner). The second end 226 of the base member 212 includes a control bore 248 configured to receive a first portion of the control shaft 216. The first end 224 of the base member 212 includes a control counterbore 250 configured to receive a second portion of the control shaft 216. In some embodiments, the first end 224 of the base member 212 further includes a dovetail recess 258, and the second end 226 of the base member 212 further includes a dovetail recess 260.

In one embodiment, the adjustable member 214 includes a front or first end 262, a rear or second end 264, and a central recess or cavity 278 positioned between the first end 262 and the second end 264. A side cavity 284 in the adjustable member 214 extends to the central cavity 278. The adjustable member 214 further includes a top surface 266 having ridges or projections 268 formed by corresponding grooves, a bottom surface 270 including ridges or projections 272 formed by corresponding grooves, a pair of top portions 280, and a pair of bottom portions 282. In some embodiments, top and bottom portions 280, 282 are configured to slide underneath or within the top and bottom portions of base member 212 when implant 210 is in the first, collapsed position. The first end 262 of the adjustable member 214 further includes a dovetail projection 286, and the second end 264 of the adjustable member 214 further includes a dovetail projection 288.

Figure 13:
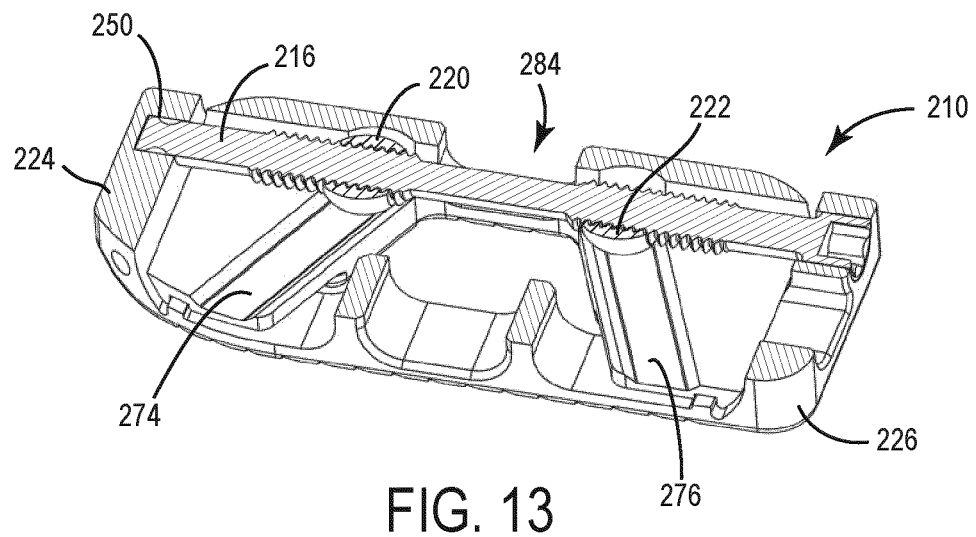
FIG. 13 is a side perspective cross-sectional view of the implant of FIG. 10 in a collapsed position according to one embodiment.
Figure 14:
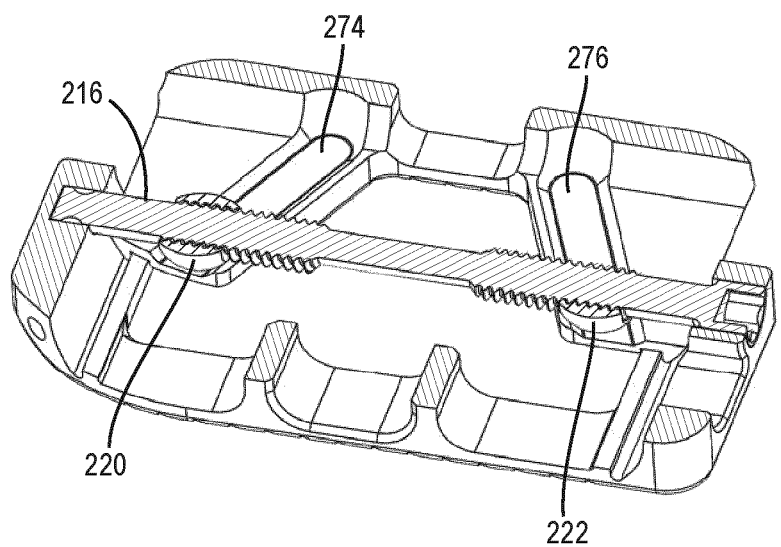
FIG. 14 is a side perspective cross-sectional view of the implant of FIG. 10 in an expanded position according to one embodiment.
Figure 15:
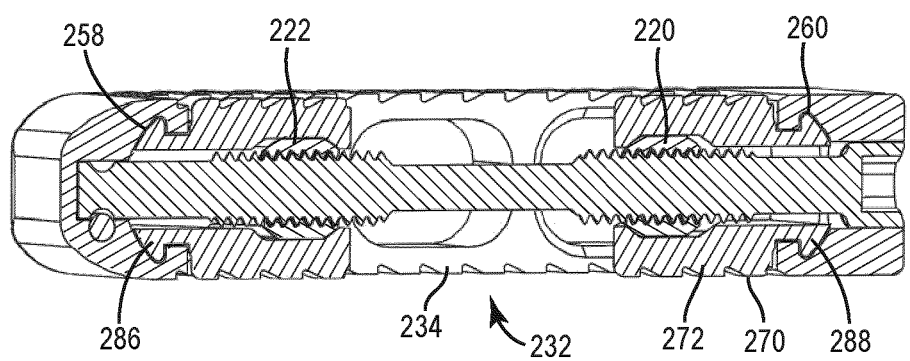
FIG. 15 is a top cross-sectional view of the implant of FIG. 1 according to one embodiment.

Referring to FIGS. 13-14, in one embodiment, the adjustable member 214 includes one or more control channels, such as a first control channel 274 and a second control channel 276. The first control channel 274 receives the first control member 220, and the second control channel 276 receives the second control member 222. In some embodiments, the control members 220, 222 are received in or on the control channels 274, 276 in a sliding manner such that the control members 220, 222 are able to translate within the control channels 274, 276. In further embodiments, each control channel has a shape such that the control channel surrounds the control member and at least partially corresponds in shape to the control member.

Implant 210 is adjustable in a similar manner to implant 10. However, while adjustment of implant 10 causes a change in height of the implant 10, adjustment of the implant 210 causes a change in width of the implant 210 (while maintaining a constant height). As such, while during adjustment of the implant 10, the top surface 66 of the adjustable member 14 may be offset from the top surface 28 of the base member 12, during adjustment of implant 210, the top surface 266 of the adjustable member 214 stays generally aligned with the top surface 228 of the base member 212. As such, the implant 210 may be used to provide, for example, a more stable implant by increasing the footprint of the implant and engagement areas with adjacent portions of bone. The implantation of the implant 210 is otherwise similar to that of the implant 10.

It should be noted that the implant 210 may share various features with the other implants described herein, and be made of the same, similar, or different materials. For example, various components of implant 210 may be made of metal, plastic, composites, or other suitable bio-compatible materials. Further, implant 210 may be usable in connection with the spine or other parts of the body.

Figure 16:
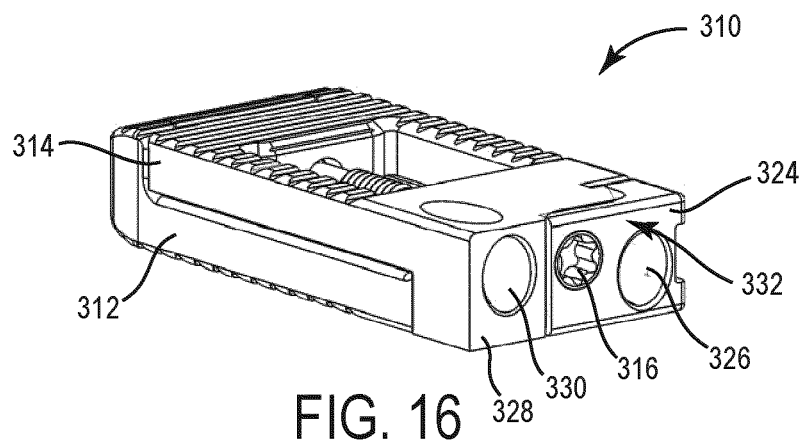
FIG. 16 is a perspective view of an expandable implant in a collapsed position according to another embodiment.
Figure 17:
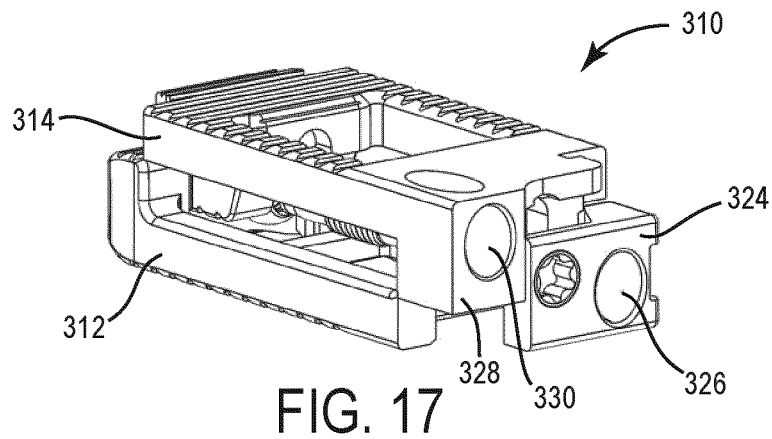
FIG. 17 is a perspective view of the implant of FIG. 16 in an expanded position according to one embodiment.
Figure 18:
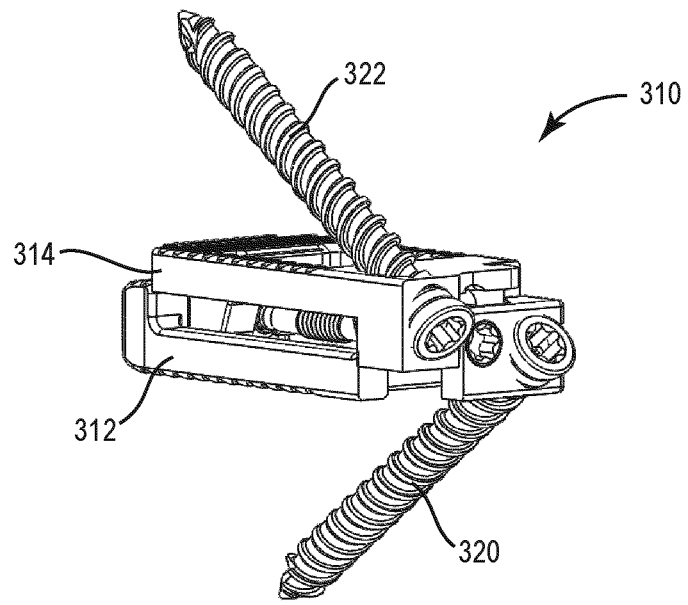
FIG. 18 is a perspective view of bone screws usable with the implant of FIG. 16 according to one embodiment.

Referring now to FIGS. 16-18, in some embodiments, one or both of a base member or an adjustable member of an implant may be configured to receive a bone screw to further secure the implant to adjacent portions of bone. For example, as shown in FIGS. 16-18, an implant 310 includes a base member 312 and an adjustable member 314 adjustably coupled to the base member 312. A control shaft 316 is received by the base member 312 and is retained by a retention pin passing through a portion of the base member 312. A first control member and a second control member are received on the control shaft 316 and are movable along the control shaft 316 to adjust a position of the adjustable member 314 between a collapsed position, as shown in FIG. 16, and an expanded position, as shown in FIG. 17. Bone screws 320, 322 extend through base member 312 and adjustable member 314.

Implant 310 may share any combination of the features disclosed herein with respect to the other implants, and all such combinations of features are to be understood to be within the scope of the present disclosure. In one embodiment, the implant 310 is generally rectangular in shape when in a first, collapsed position. As shown in FIG. 17, in some embodiments, the base member 312 includes a first bone screw support portion 324 having a first bone screw bore 326 configured to receive bone screw 320. Similarly, adjustable member 314 includes a second bone screw support portion 328 having a second bone screw bore 330 configured to receive bone screw 322. The first bone screw support portion 324 and the second bone screw support portion 328 collectively form a proximal face 332 for implant 310. As shown in FIG. 16, the first bone screw bore 326, the second bone screw bore 330, and the control shaft 316 are accessible by way of the proximal face 332 of the implant 310.

It should be noted that the implant 310 may share various features with the other implants described herein, and be made of the same, similar, or different materials. For example, various components of the implant 310 may be made of metal, plastic, composites, or other suitable bio-compatible materials. Further, the implant 310 may be usable in connection with the spine or other parts of the body.

Referring now to FIGS. 19-26, an expandable implant 410 is shown according to an exemplary embodiment. The implant 410 is usable, for example, between and/or within vertebral bodies of the spine, and may share any or all of the features of the other inter/intra-body implants discussed elsewhere herein. All such combinations of features are to be understood to be within the scope of the present disclosure. It should be understood that the implant 410 may in some embodiments be usable in other portions of the body in addition to the spine, and all such applications are to be understood to be within the scope of the present disclosure. The implant 410 is substantially similar to the implant 10 in structure and function except as discussed herein with respect to the control members and corresponding control rails.

Figure 19:
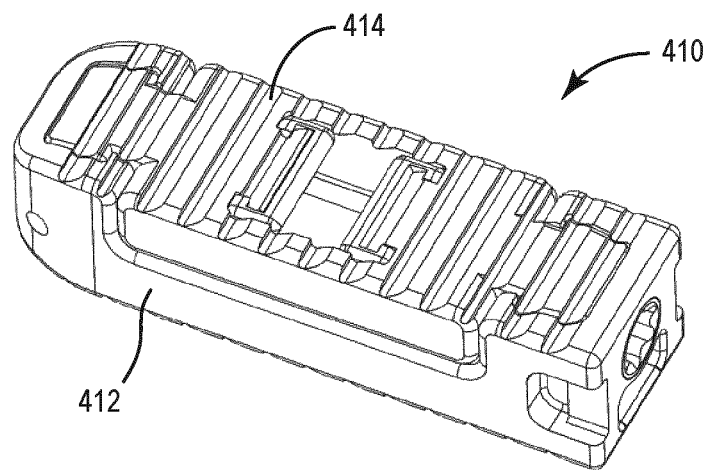
FIG. 19 is a perspective view of an expandable implant in a collapsed position according to another embodiment.
Figure 20:
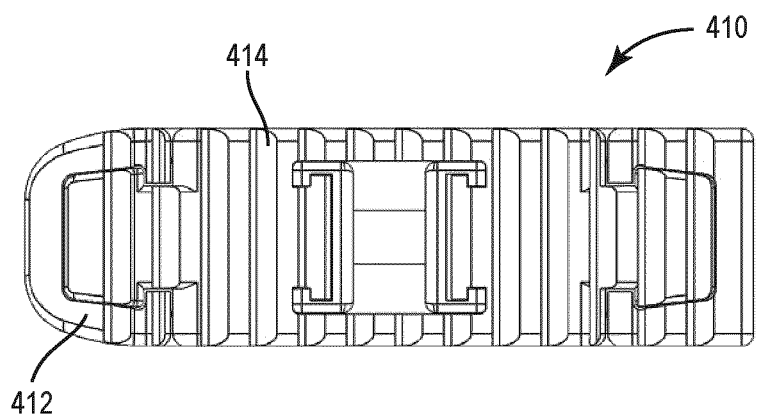
FIG. 20 is a top view of the implant of FIG. 19 according to one embodiment.
Figure 21:
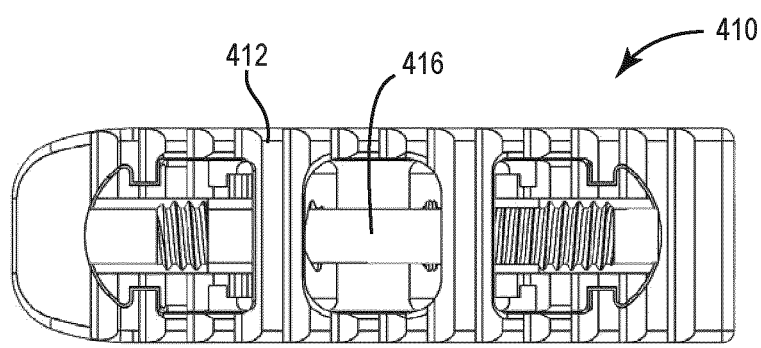
FIG. 21 is a bottom view of the implant of FIG. 19 according to one embodiment.
Figure 22:
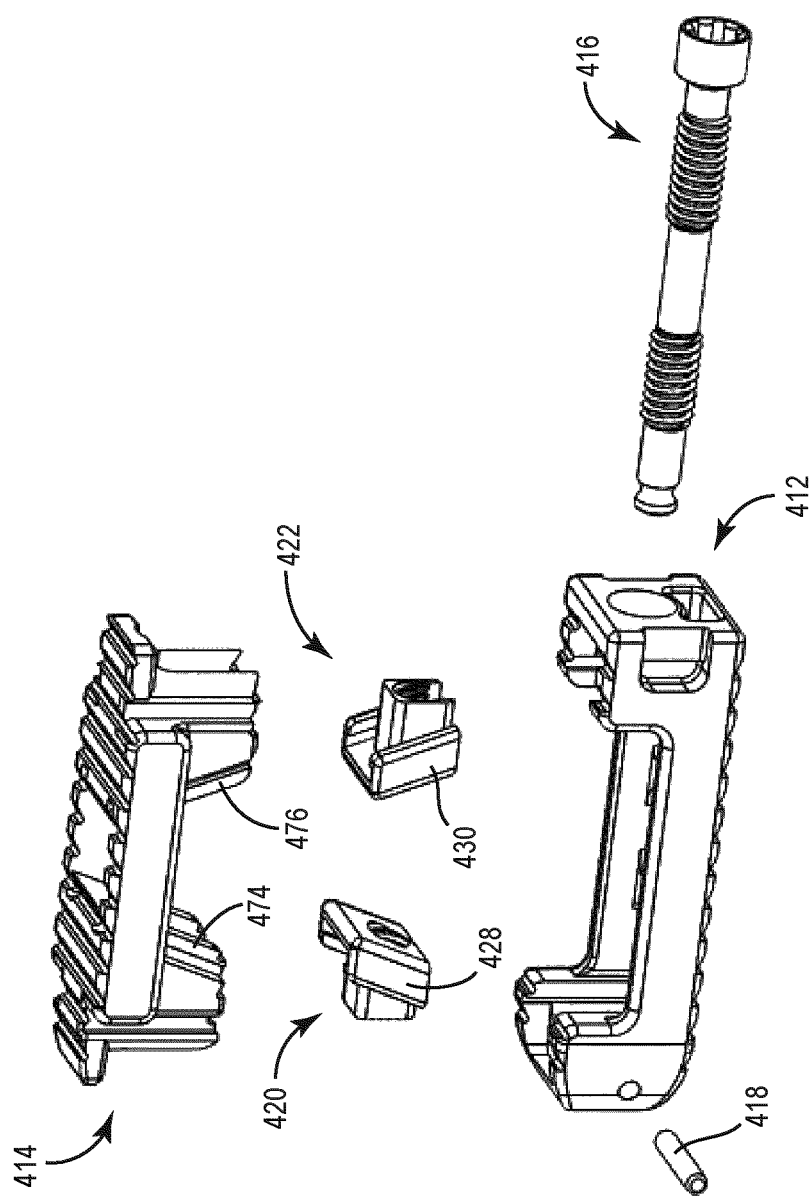
FIG. 22 is an exploded view of the implant of FIG. 19 according to one embodiment.

According to an exemplary embodiment, the implant 410 includes a base member 412 and an adjustable member 414 adjustably coupled to the base member 412. A control shaft 416 is received by the base member 412 and is retained by a retention pin 418 passing through a portion of the base member 412. A first control member 420 and a second control member 422 are received on the control shaft 416 and are movable along the control shaft 416 to adjust a position of the adjustable member 414 between a collapsed position, as shown in FIG. 19, and an expanded position, as shown in FIG. 23.

Referring to FIGS. 22-26, in one embodiment, the adjustable member 414 includes one or more control rails, such as a first control rail 474 and a second control rail 476. First control rail 474 receives first control member 420, and second control rail 476 receives second control member 422. In some embodiments, control members 420, 422 are received on control rails 474, 476 in a sliding manner such that the control members 420, 422 are able to translate on the control rails 474, 476. For example, the control rails 474, 476 may define control channels on or in which the control members 420, 422 are received. In further embodiments, each control rail has a shape such that the control member surrounds all or a portion of the control rail and at least partially corresponds in shape to the control rail.

The first control member 420 includes control arms 428 configured to engage the first control rail 474. The second control member 422 includes control arms 430 configured to engage the second control rail 476. The first control member 420 and the second control member 422 move or translate both along the control shaft 416 and along the first control rail 474 and the second control rail 476. In some embodiments, each control arm is substantially U-shaped and configured to wrap around an end portion of the corresponding control rail. In other embodiments, other shapes and/or configurations of control rails and control arms or other components may be utilized.

Figure 23:
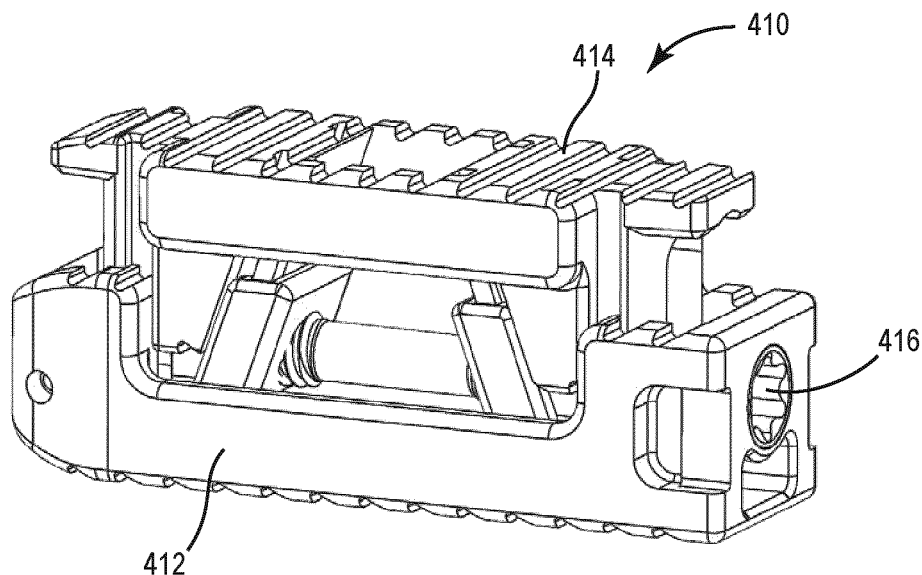
FIG. 23 is a perspective view of the implant of FIG. 19 in an expanded position according to one embodiment.
Figure 24:
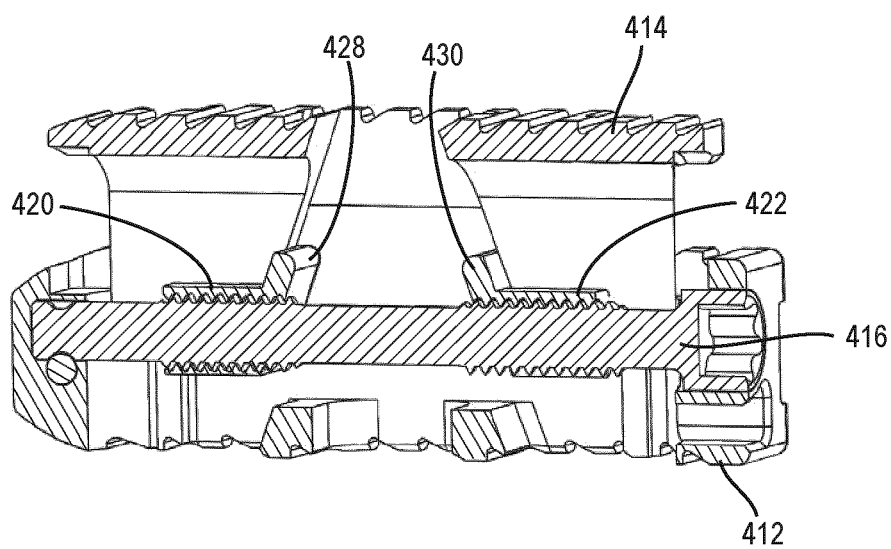
FIG. 24 is a cross-sectional view of the implant of FIG. 19 in an expanded position according to one embodiment.
Figure 25:
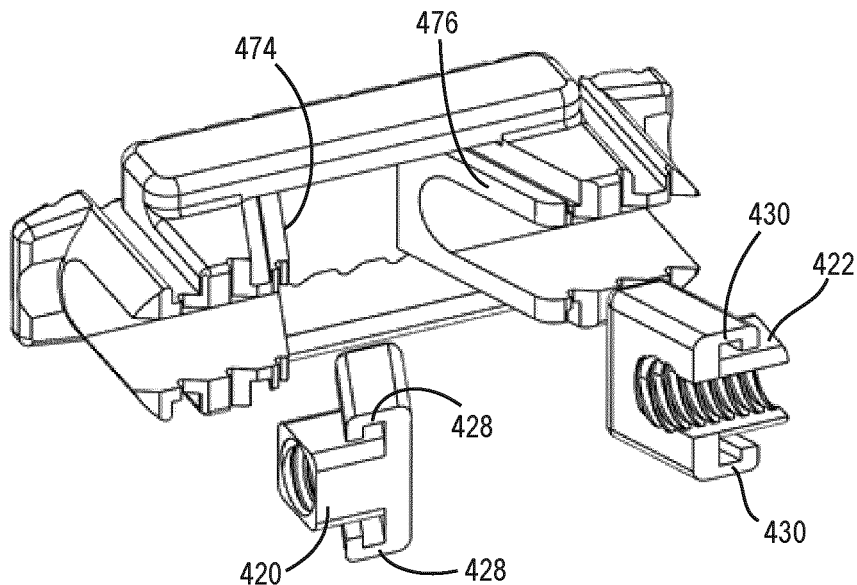
FIG. 25 is a partial exploded view of the implant of FIG. 19 according to one embodiment.
Figure 26:
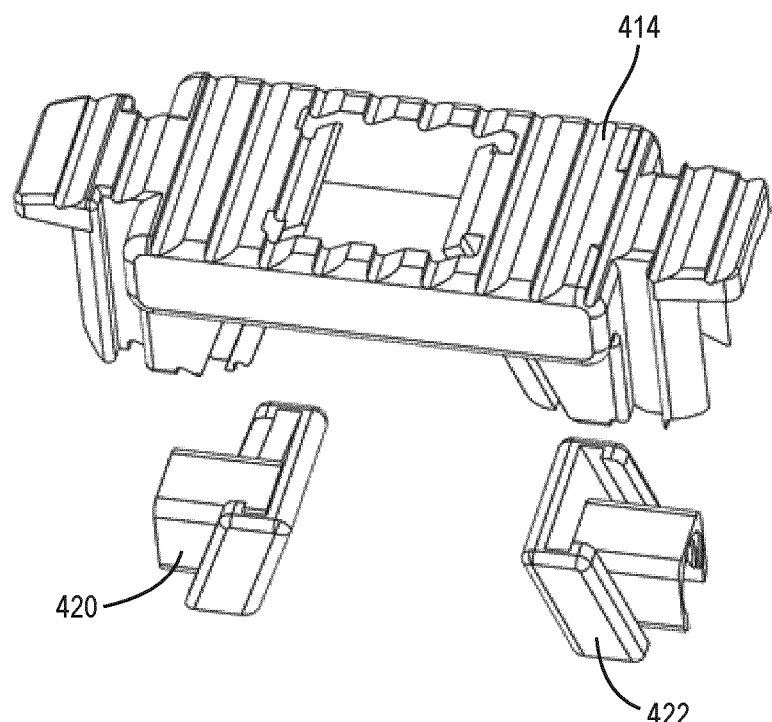
FIG. 26 is a partial exploded view of the implant of FIG. 19 according to another embodiment.

Similar to implant 10, and as shown in FIGS. 23 and 24, as the control members 420, 422 move along the control shaft 416, the control members 420, 422 further move along the control rails 474, 476, thereby causing relative movement of the adjustable member 414 and the base member 412. As the control members 420, 422 translate along the control shaft 416, the adjustable member 414 is moved due to the orientation and shape of the first and second control rails 474, 476. The rate of movement of the control members 420, 422, and therefore adjustable member 414, can be adjusted by modifying the slope of the control rails 474, 476 relative to the control shaft 416, as discussed in greater detail elsewhere herein, including FIGS. 9A-9C.

It should be noted that implant 410 may share various features with the other implants described herein, and be made of the same, similar, or different materials. For example, various components of implant 410 may be made of metal, plastic, composites, or other suitable bio-compatible materials. Further, implant 410 may be usable in connection with the spine or other parts of the body.

Referring now to FIGS. 27-34, an expandable implant 510 is shown according to an exemplary embodiment. The implant 510 is usable, for example, between and/or within vertebral bodies of the spine, and may share any or all of the features of the other inter/intra-body implants discussed elsewhere herein. All such combinations of features are to be understood to be within the scope of the present disclosure. It should be understood that the implant 510 may in some embodiments be usable in other portions of the body in addition to the spine, and all such applications are to be understood to be within the scope of the present disclosure. The implant 510 is substantially similar to implant 10, with the exception of the configuration of the control channels as discussed below.

Figure 27:
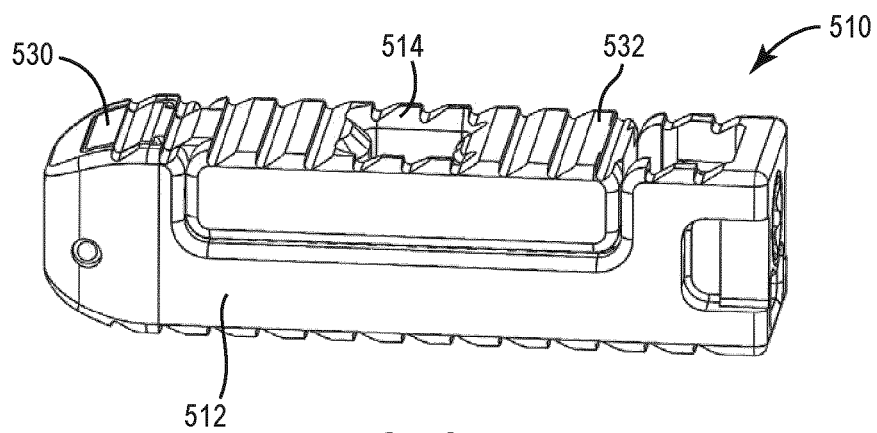
FIG. 27 is a perspective view of an implant in a collapsed position according to another embodiment.
Figure 29:
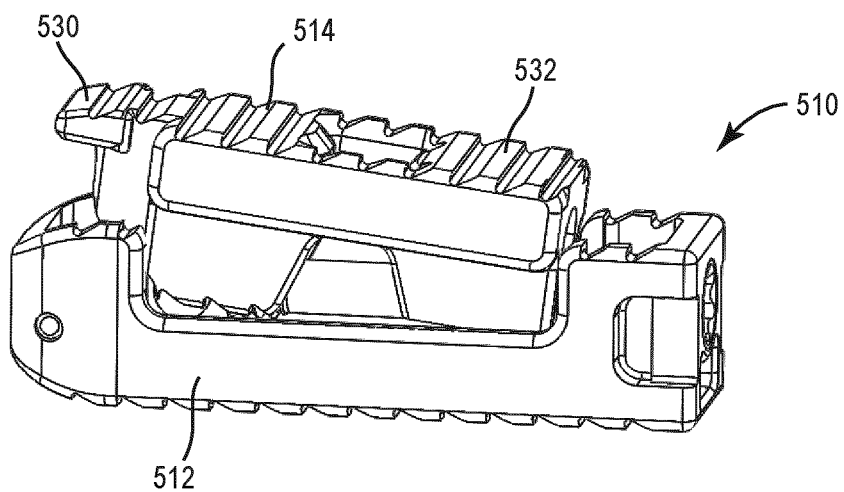
FIG. 29 is a perspective view of the implant of FIG. 27 in an expanded position according to one embodiment.
Figure 30:
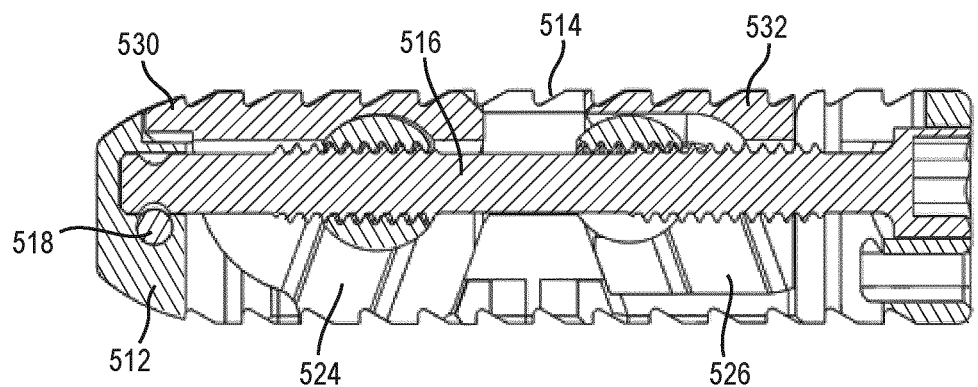
FIG. 30 is a side cross-section view of the implant of FIG. 27 in a collapsed position according to one embodiment.
Figure 32:
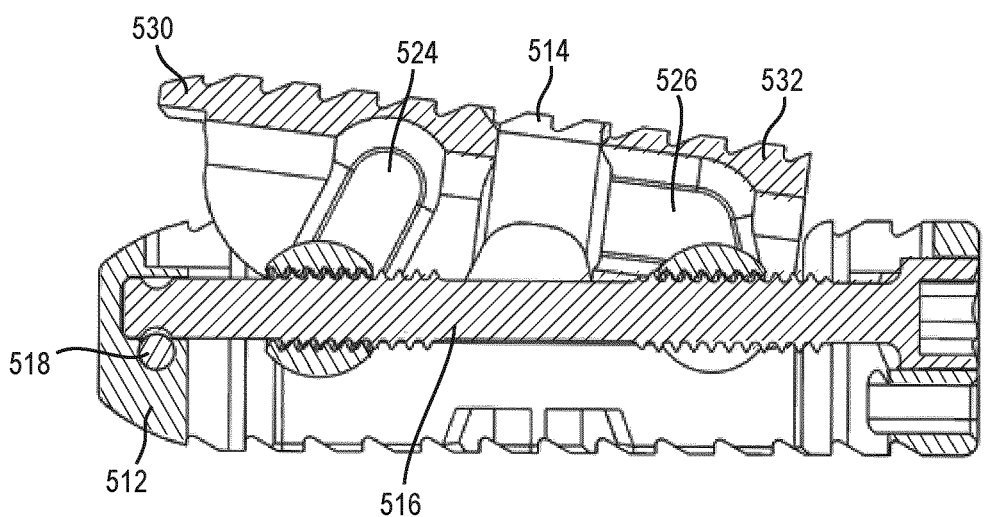
FIG. 32 is a side cross-section view of the implant of FIG. 27 in an expanded position according to one embodiment.
Figure 33:
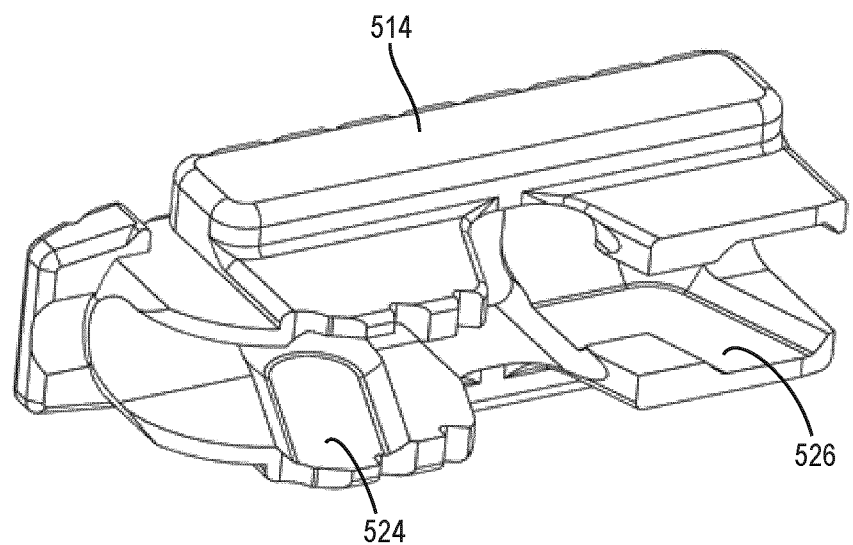
FIG. 33 is a perspective view of a portion of the implant of FIG. 27 according to one embodiment.

According to an exemplary embodiment, the implant 510 includes a base member 512 and an adjustable member 514 adjustably coupled to the base member 512. A control shaft 516 is received by the base member 512 and is retained by a retention pin 518 passing through a portion of the base member 512. A first control member 520 and a second control member 522 are received on the control shaft 516 and are movable along the control shaft 516 to adjust a position of the adjustable member 514 between a collapsed position, as shown in FIGS. 27 and 30, and an expanded position, as shown in FIGS. 29 and 32.

In one embodiment, the adjustable member 514 includes a front or first end 530, and a rear or second end 532. The adjustable member 514 further includes one or more control channels, such as a first control channel 524 and a second control channel 526. The first control channel 524 receives the first control member 520, and the second control channel 526 receives the second control member 522. In some embodiments, the control members 520, 522 are received in the control channels 524, 526 in a sliding manner such that the control members 520, 522 are able to translate within the control channels 524, 526. In further embodiments, each control channel has a shape such that the control channel surrounds the control member and at least partially corresponds in shape to the control member.

As shown in FIGS. 27-32, as the control members 520, 522 move along the control shaft 516, the control members 520, 522 further move within the control channels 524, 526, thereby causing relative movement of the adjustable member 514 and the base member 512. As the control members 520, 522 translate along the control shaft 516, the adjustable member 514 is moved based on the shape of the first and second control channels 524, 526. The rate of movement of the control members 520, 522, and therefore the adjustable member 514, can be adjusted by modifying the slope of the control channels 524, 526 relative to the control shaft 516.

Figure 34:
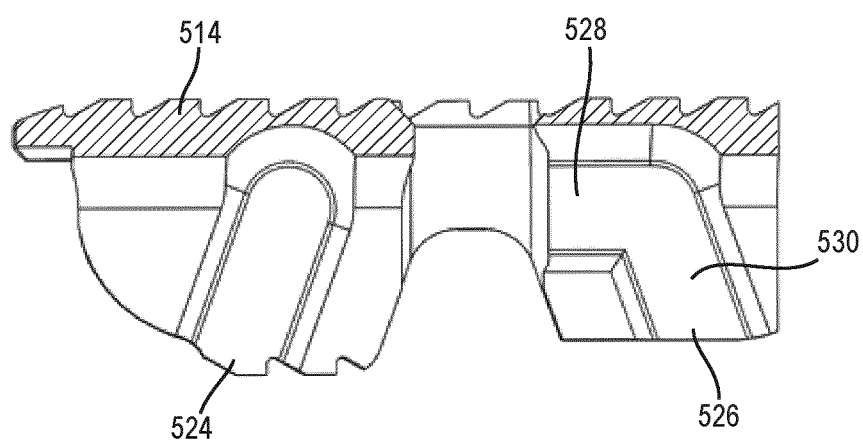
FIG. 34 is a cross-section view of the portion of the implant of FIG. 33 according to one embodiment.

For example, as shown in FIG. 34, the first control channel 524 extends at an angle relative to the control shaft 516, and has a substantially linear form and constant slope, thereby providing a generally constant corresponding rate of movement of the first end 530 of the adjustable member 514. The second control channel 526 includes a first channel portion 528 and a second channel portion 530 which extend at different angles relative to the control shaft 516. As shown in FIG. 34, the first channel portion 528 is generally parallel to the control shaft 516, and the second channel portion 530 extends at an angle similar to that of first control channel 524. As such, the second control channel 526 provides a non-constant rate of movement of second end 532 of the adjustable member 514.

Figure 28:
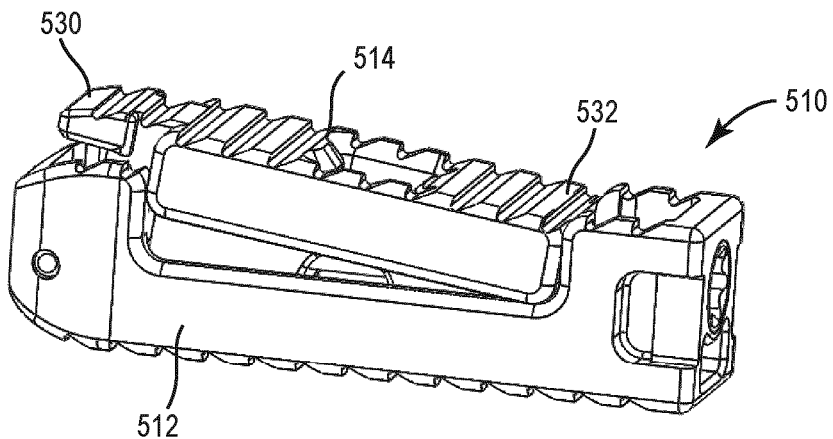
FIG. 28 is a perspective view of the implant of FIG. 27 in an intermediate position according to one embodiment.
Figure 31:
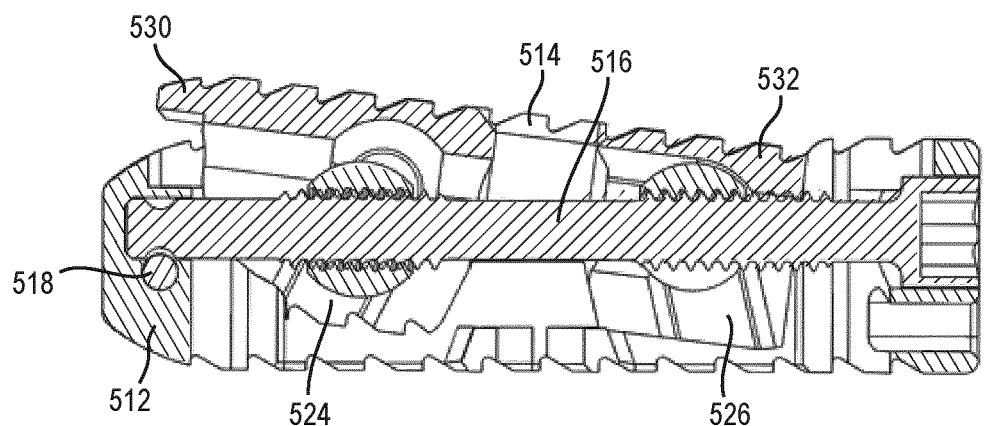
FIG. 31 is a side cross-section view of the implant of FIG. 27 in an intermediate position according to one embodiment.

FIGS. 27-32 illustrate the corresponding movement of the adjustable member 514 resulting from the differing configurations of the first control channel 524 and the second control channel 526. In FIGS. 27 and 30, the implant 510 is in a collapsed position, such that the control members 520, 522 reside in the upper/inner—most positions within the first and second control channels 524, 526. FIGS. 28 and 31 illustrate implant 510 in an intermediate expanded position, where second control member 522 is positioned generally at the intersection of the first channel portion 528 and the second channel portion 530. Due to the orientation of the first channel portion 528, the second end 532 of adjustable member 514 has remained generally at the same height as that shown in FIGS. 28 and 30, while due to the configuration of first control channel 524, the first end 530 of the adjustable portion 514 has moved upward relative to the base member 512. FIGS. 29-32 show the implant 510 in a fully expanded position, where control members 520, 522 reside in the lower/outer—most positions within the first and second control channels 524, 526. Due to the angled configurations of both the first control channel 524 and the second channel portion 530 of the second control channel 526, both the first end 530 and the second end 532 move relative to the base member 512.

Providing an implant with adjustment features such as those provided by implant 510 may facilitate accommodating a desired spinal curvature or other anatomical features where non-parallel supporting surfaces are suitable for a particular application. It should be noted that the control channels and/or control rails herein may take any desired configuration to provide desired expansion and contraction characteristics for a particular implant.

Referring now to FIGS. 35-44, an expandable implant 610 is shown according to an exemplary embodiment. Implant 610 may share many of the features of the other inter/intra-body implants discussed elsewhere herein. All such combinations of features are to be understood to be within the scope of the present disclosure. Implant 610 is generally similar to the other implants disclosed herein in structure and function except that implant 610 utilizes a single control member/control channel configuration, and further utilizes a pivot pin about which an adjustable member pivots relative to a base member.

Figure 35:
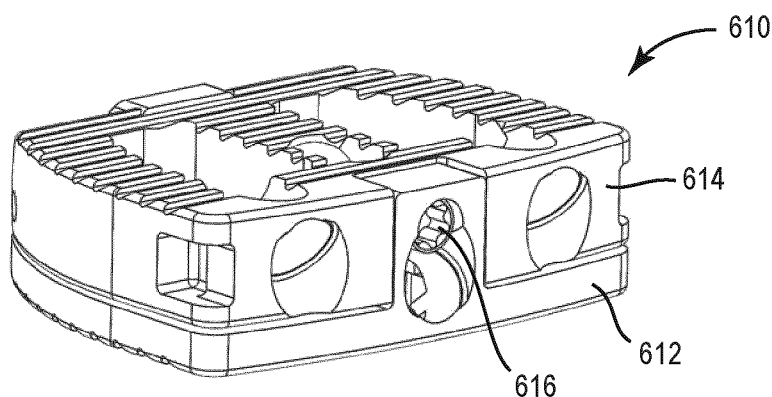
FIG. 35 is a side perspective view of an implant in a collapsed position according to another embodiment.
Figure 36:
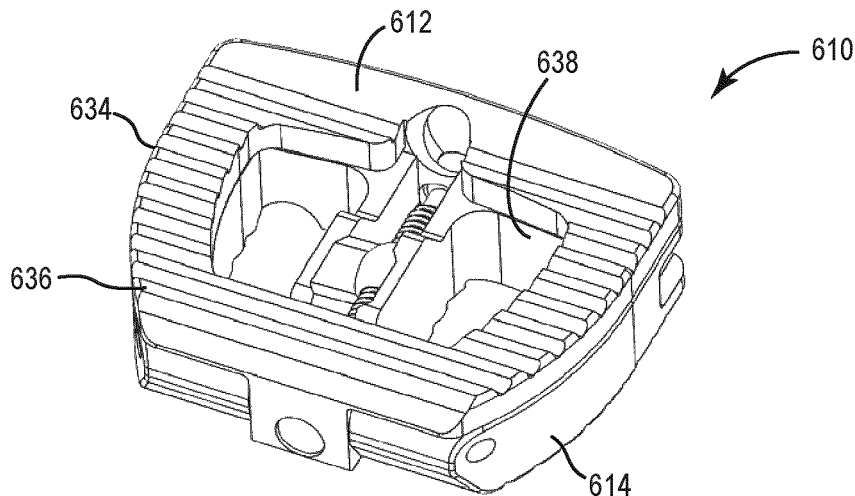
FIG. 36 is a bottom perspective view of the implant of FIG. 35 according to one embodiment.
Figure 37:
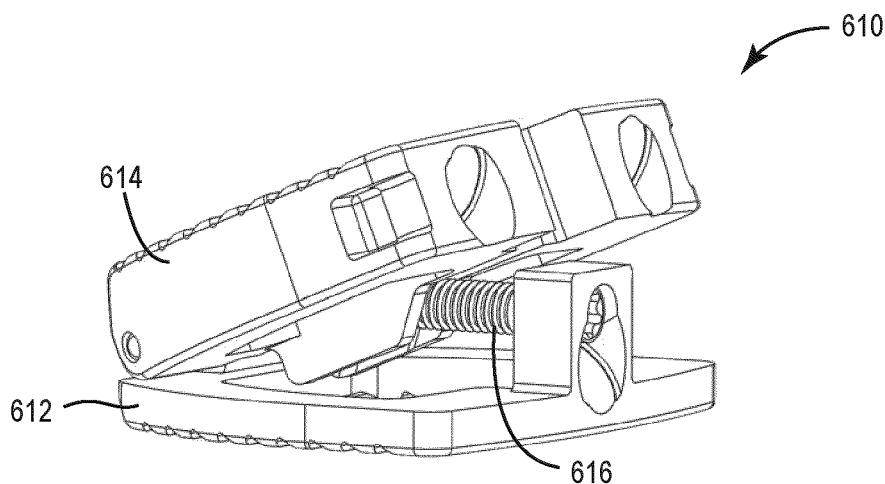
FIG. 37 is a perspective view of the implant of FIG. 35 in an expanded position according to one embodiment.
Figure 38:
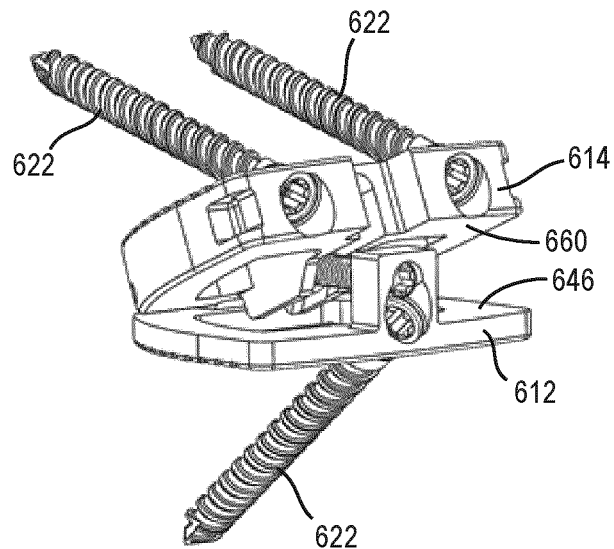
FIG. 38 is perspective view of the implant of FIG. 35 in an expanded position with bone screws according to one embodiment.

According to an exemplary embodiment, implant 610 includes a base member 612 and an adjustable member 614 adjustably coupled to the base member 612. A control shaft 616 is received by the base member 612 and is retained by a retention pin 618 (e.g., a pivot pin or member, retaining pin) passing through a portion of the base member 612 and/or the adjustable member 614. A control member 620 is received on the control shaft 616 and is movable along the control shaft 616 to adjust a position of the adjustable member 614 between a collapsed position, as shown in FIGS. 35 and 36, and an expanded position, as shown in FIGS. 37 and 38.

In one embodiment, the base member 612 includes a front or first end 624, a rear or second end 626, and a central cavity 638 disposed between the first end 624 and the second end 626. The base member 612 further includes a top surface 646 and a bottom surface 634 opposite the top surface 646 and having ridges or projections 636 formed by corresponding grooves. The projections 636 are configured to engage adjacent portions of bone. The base member 612 further includes a planar portion 628. A first extension 630 is positioned at the first end 624 and extends upward from the planar portion 628, and a second extension 632 is positioned at the second end 626 and extends upward from the planar portion 628. A pin aperture 640 extends through the first extension 630 and is configured to receive the retention pin 618 (e.g., in a press fit, sliding, or other manner). The second extension 632 includes a bone screw bore 650 configured to receive a bone screw 622. The first extension 630 includes a first control bore 642 and the second extension includes a second control bore 644. Control bores 642, 644 receive opposing ends of the control shaft 616.

Figure 43:
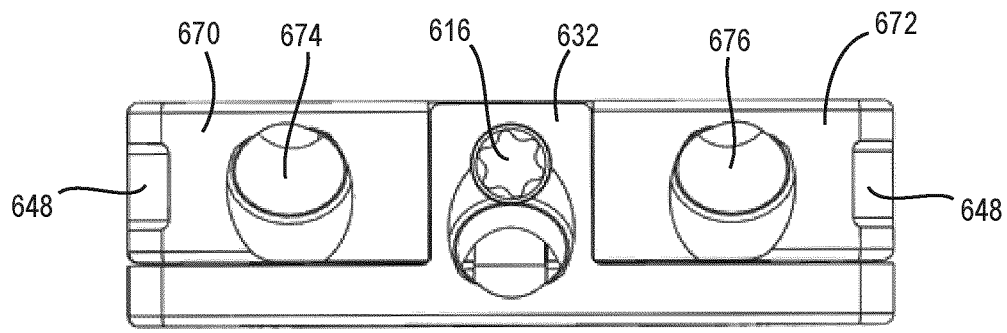
FIG. 43 is a front view of the implant of FIG. 35 according to one embodiment.
Figure 44:
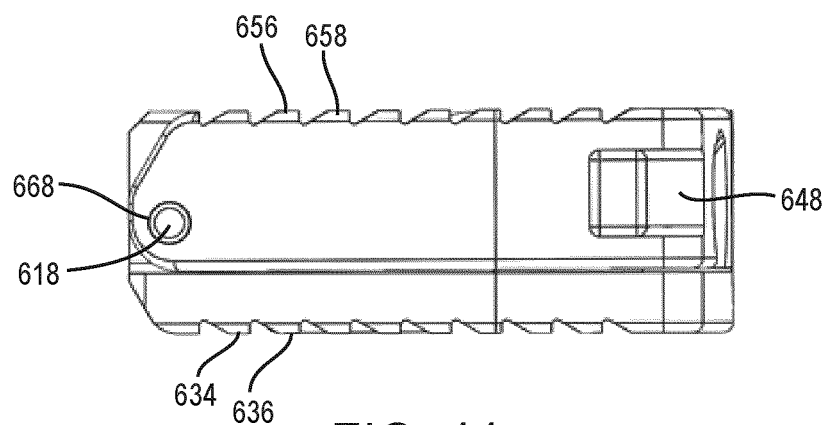
FIG. 44 is a side view of the implant of FIG. 35 according to one embodiment.

In one embodiment, the adjustable member 614 includes a front or first end 652, a rear or second end 654, and cavities 664 extending through the adjustable member 614 and positioned between the first end 652 and the second end 654. The adjustable member 614 further includes a top surface 656 having ridges or projections 658 formed by corresponding grooves, and a bottom surface 660. The adjustable member 614 further includes pin apertures 668 configured to receive the retention pin 618 to enable movement (e.g., pivoting) of the adjustable member 614 relative to the base member 612. Further, the adjustable member includes a first bone screw support portion 670 including a bone screw bore 674 and a second bone screw support portion 672 having a bone screw bore 676. As shown in FIG. 43, the first and second bone screw support portions 670, 672 of the adjustable member 614 and the second extension 632 of the base member 612 collectively form a front face of the implant 610, such that the control shaft 616 and the bone screws 622 are accessible via the front face of the implant 610 (e.g., when the implant 610 is in a collapsed position).

Figure 39:
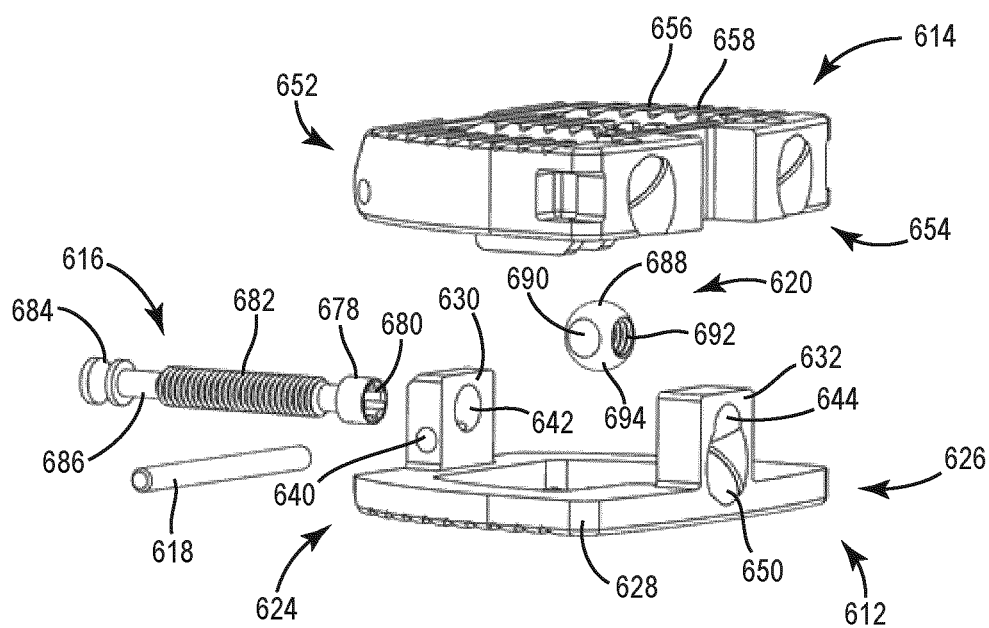
FIG. 39 is an exploded view of the implant of FIG. 35 according to one embodiment.
Figure 40:
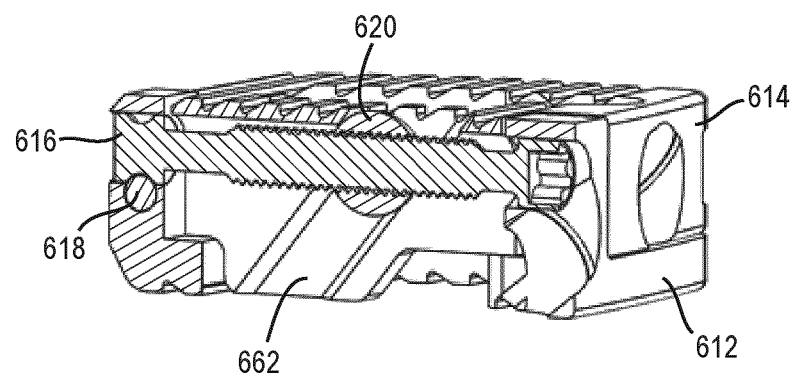
FIG. 40 is a cross-section view of the implant of FIG. 35 in a collapsed position according to one embodiment.
Figure 41:
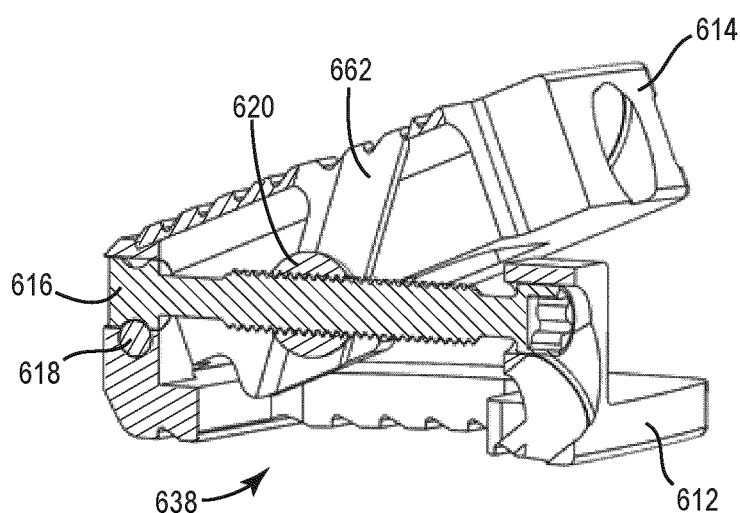
FIG. 41 is a cross-section view of the implant of FIG. 35 in an expanded position according to one embodiment.
Figure 42:
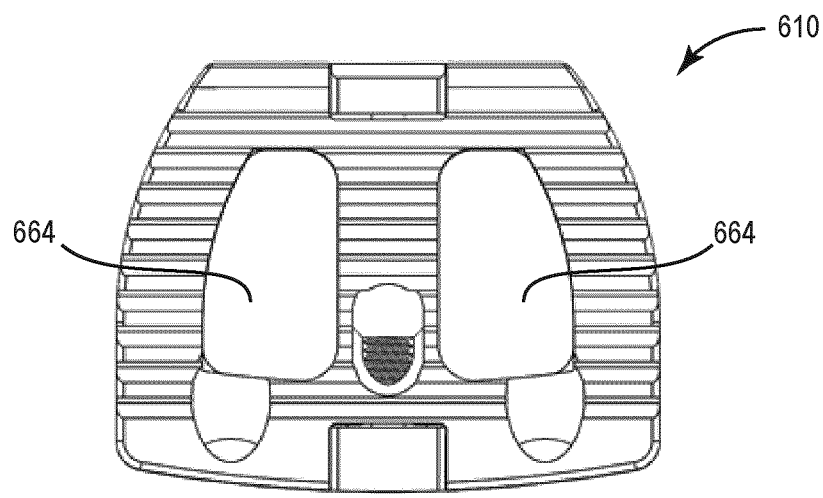
FIG. 42 is a top view of the implant of FIG. 35 according to one embodiment.

Referring to FIGS. 39-41, in one embodiment, the adjustable member 614 includes one or more control channels, such as control channel 662. The control channel 662 receives the control member 620. In some embodiments, the control member 620 is received in the control channel 662 in a sliding manner such that the control member 620 is able to translate within the control channel 662. In further embodiments, the control channel 662 has a shape such that the control channel 662 surrounds the control member 620 and at least partially corresponds in shape to the control member 620.

Referring to FIG. 39, the control shaft 616 includes a head portion 678, a tool port 680 disposed within the head portion 678, and a retention groove 684 located at an end opposite the head portion 678. In some embodiments, the control shaft 616 further includes a control thread 682. Non-threaded portions 686 may be located on one or both side of the control thread 682.

The control member 620 includes a body 688, one or more flat portions 690, and an internal thread 692. In some embodiments, the control member 620 further includes a slotted portion configured to enable passing the control member 620 over a portion (e.g., non-threaded portion 686) of the control shaft 616. The control member 620 moves or translates both along the control shaft 616 and within or on the control channel 662.

Referring to FIGS. 40-41 the control shaft 616 is received by the base member 612 such that the retention groove 684 is positioned with the first extension 630 of the base member 612 and the head portion 678 is positioned within the second extension 632 of the base member 612. In one embodiment, the control shaft 616 is rotatable within the base member 612, and the retention pin 618 extends through the first extension 630 and into the retention groove 684 of the control shaft 616 to enable rotation of the control shaft 616 while inhibiting translation of the control shaft 616 relative to the base member 612. The internal thread 692 of the control member 620 is received on the control thread 682 of the control shaft 616 such that as the control member 620 moves along the control shaft 616, the control member 620 further moves within the control channel 662, thereby causing relative movement (e.g., pivotal movement) of the adjustable member 614 relative to the base member 612 (e.g., about retention pin 618). For example, FIGS. 40 and 41 show the control member 620 moving along the control shaft 616. As the control member 620 translates along the control shaft 616, the adjustable member 614 pivots about the retention pin 618. The rate of movement of the control member 620, and therefore the adjustable member 614, can be adjusted by modifying the slope of the control channel 662 relative to the control shaft 616.

In use, implant 610 is positioned within a desired space (e.g., between adjacent portions of bone) while in the first, collapsed position, as shown in FIG. 35. To position implant 610, an appropriate tool may be used to engage tool recesses 648 and manipulate implant 610 into a desired position. Once in a desired position, a subsequent tool may be utilized to engage tool port 680 and rotate control shaft 616 to pivot adjustable member 614 to a desired degree of expansion. It should be noted that based on a particular application, the adjustable member 614 may be utilized in a fully collapsed position, a fully expanded position, or any intermediate position therebetween. One or more bone screws 622 may be screwed into adjacent portions of bone as shown in FIG. 38. Once implant 610 is properly positioned and expanded to a desired height, bone graft material may be delivered by way of, for example, apertures 664 or alternatively, by the space formed due to the expansion of adjustable member 614. The various apertures in and through the base member 612 and adjustable member 614 may in some embodiments facilitate the growth of bone material in and around implant 610 to further stabilize the device.

It should be noted that implant 610 may share various features with the other implants described herein, and be made of the same, similar, or different materials. For example, various components of implant 610 may be made of metal, plastic, composites, or other suitable bio-compatible materials. Further, implant 160 may be usable in connection with the spine or other parts of the body.

Referring now to FIGS. 45-54, an expandable implant 710 is shown according to an exemplary embodiment. Implant 710 may include any of the features shown and described with respect to the other expandable implants disclosed herein. For example, implant 710 is in many ways similar to implant 10, and may include any of the features of implant 10. Implant 710 is usable, for example, between and/or within vertebral bodies of the spine, and may share many of the features of the other inter/intra-body implants discussed elsewhere herein. It should be understood that implant 710 may in some embodiments be usable in other portions of the body in addition to the spine, and all such applications are to be understood to be within the scope of the present disclosure.

Figure 45:
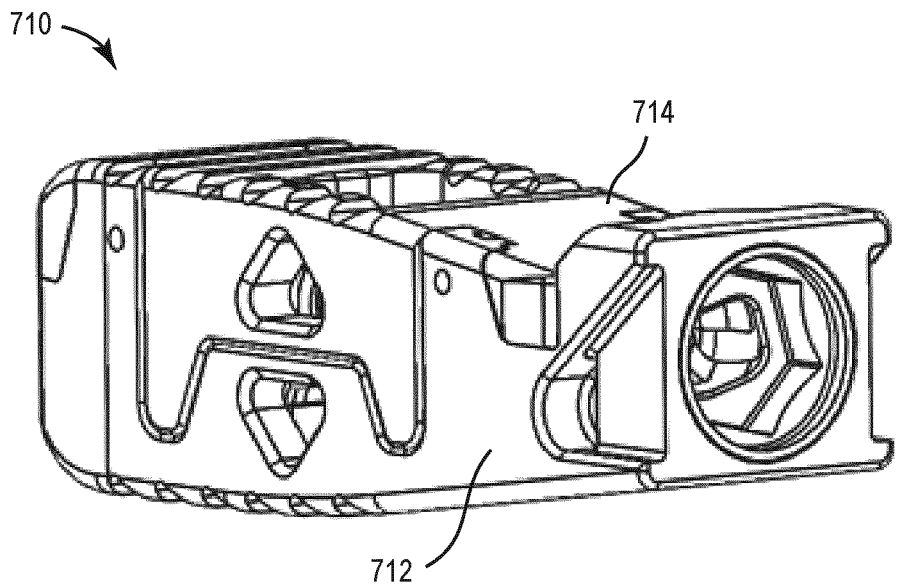
FIG. 45 is a perspective view of an implant in a collapsed position according to one embodiment.
Figure 46:
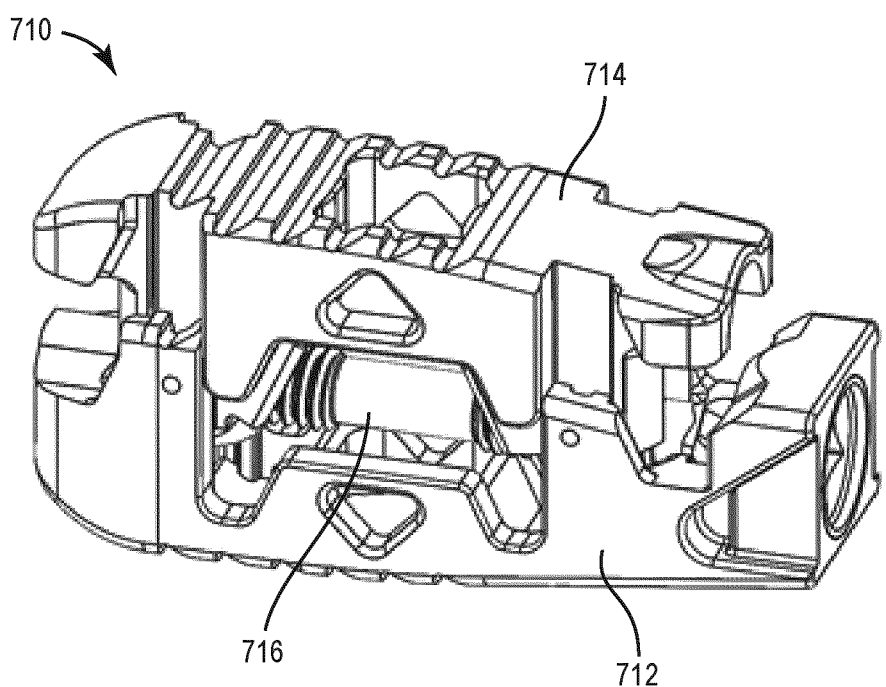
FIG. 46 is a perspective view of the implant of FIG. 45 in an expanded position according to one embodiment.
Figure 47:
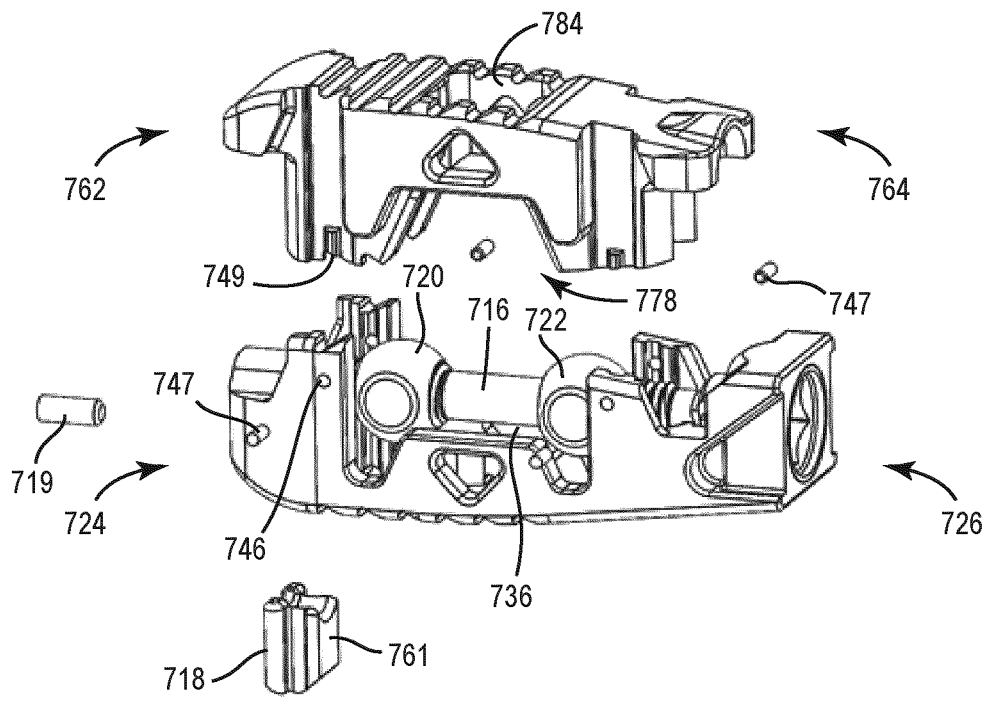
FIG. 47 is a partial exploded view of the implant of FIG. 45 according to one embodiment.
Figure 48:
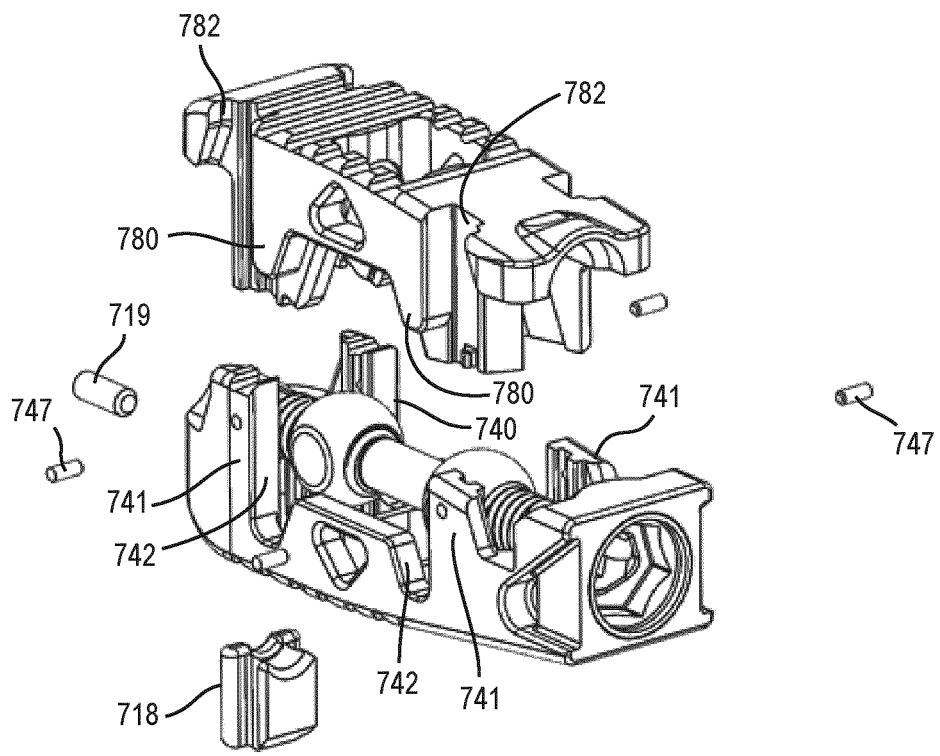
FIG. 48 is a partial exploded view of the implant of FIG. 45 according to one embodiment.
Figure 54:
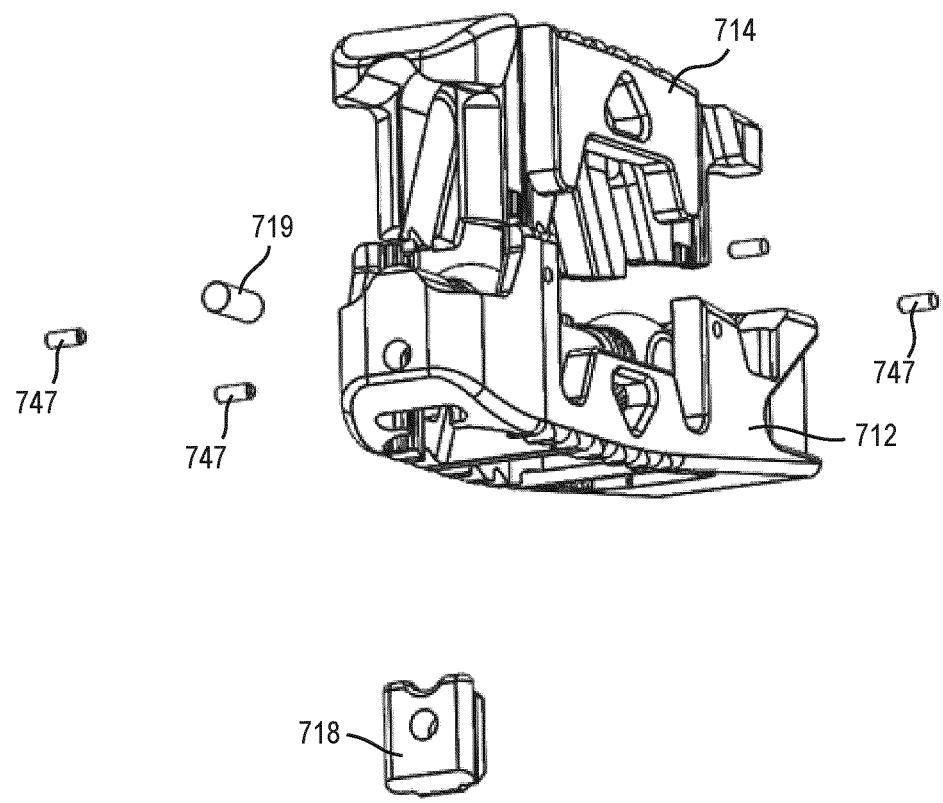
FIG. 54 is a partial exploded view of the implant of FIG. 45 according to one embodiment.

According to an exemplary embodiment, implant 710 includes a base member 712 and an adjustable member 714 adjustably coupled to the base member 712. A control shaft 716 is received by the base member 712 and is retained by a retention member 718 passing through a portion of the base member 712. Retention member 718 is in turn retained in place by a retention pin 719, which may further be welded, press-fit, or otherwise secured in place, as shown in FIG. 54. A first control member 720 and a second control member 722 are received on the control shaft 716 and are movable along the control shaft 716 to adjust a position of the adjustable member 714 between a collapsed position, as shown in FIG. 45, and an expanded position, as shown in FIG. 46.

In one embodiment, the base member 712 includes a front or first end 724, a rear or second end 726, and a central cavity 736 disposed between the first end 724 and the second end 726. The base member 712 further includes a top surface 728, a bottom surface 732 opposite the top surface 728 and having ridges or projections 734 formed by corresponding grooves, a first side 738, and a second side 740. The projections 734 are configured to engage adjacent portions of bone. The base member 712 further includes alignment guides 742 and alignment recesses 744, which engage corresponding guides and recesses on adjustable member 714. Limiting pin apertures 746 extends through one or both of first side 738 and second side 740 and are configured to receive limiting pins 747 (e.g., in a press fit or other manner). Limiting pins 747 engage corresponding projections 749 on adjustable member 714 to limit an amount of expansion of adjustable member 714 relative to base member 712. The second end 726 of the base member 712 includes a control bore 748 configured to receive a first portion of the control shaft 716. The first end 724 of the base member 712 includes a control counterbore 750 (see FIG. 50) configured to receive a second portion of the control shaft 716.

In one embodiment, the adjustable member 714 includes a front or first end 762, a rear or second end 764, and a central recess or cavity 778 positioned between the first end 762 and the second end 764. A top cavity 784 (see FIG. 5) in the adjustable member 714 extends to the central cavity 778. The adjustable member 714 further includes a top surface 766 having ridges or projections 768 formed by corresponding grooves, and a bottom surface 770 including ridges or projections 772 (see FIG. 52) formed by corresponding grooves. Alignment guides 780 and alignment recesses 782 are received by alignment recesses 742 and alignment guides 741 of base member 712 to maintain a desired alignment between the base member 712 and the adjustable member 714 (e.g., to provide linear relative movement, permit non-linear relative movement, etc.). In one embodiment, projections 749 are disposed within recesses 782 and are configured to engage limiting pins 747 to limit an amount of expansion of adjustable member 714 relative to base member 712.

Figure 50:
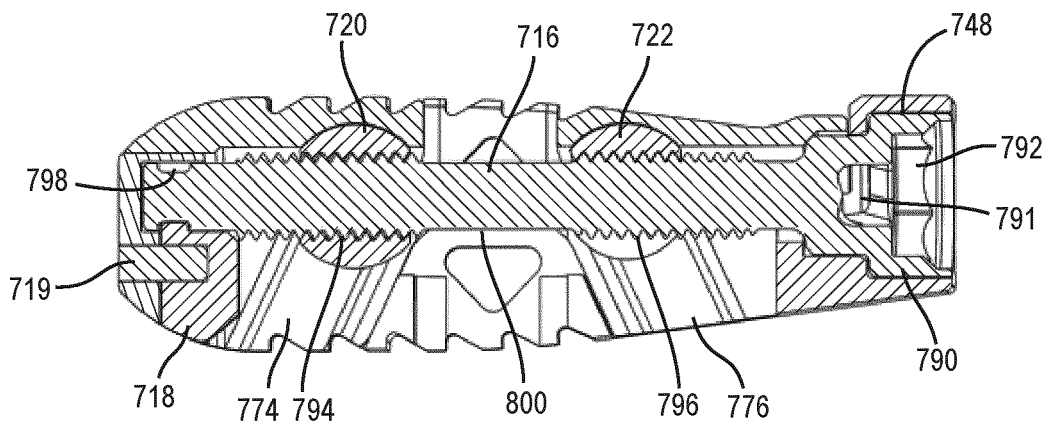
FIG. 50 is a cross-section view of the implant of FIG. 45 according to one embodiment.
Figure 51:
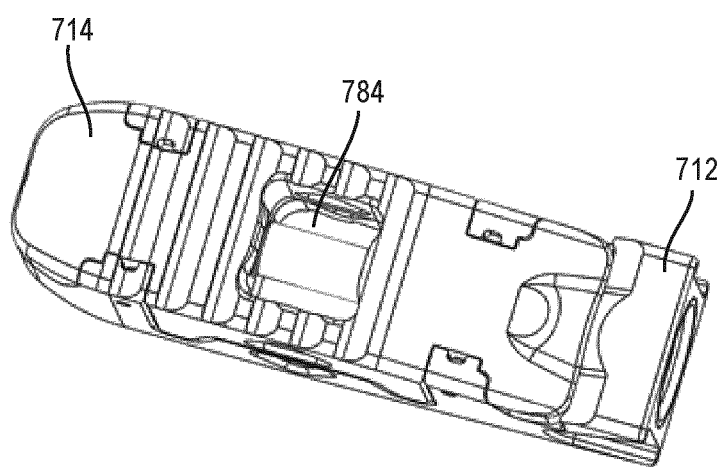
FIG. 51 is a top perspective view of the implant of FIG. 45 according to one embodiment.
Figure 52:
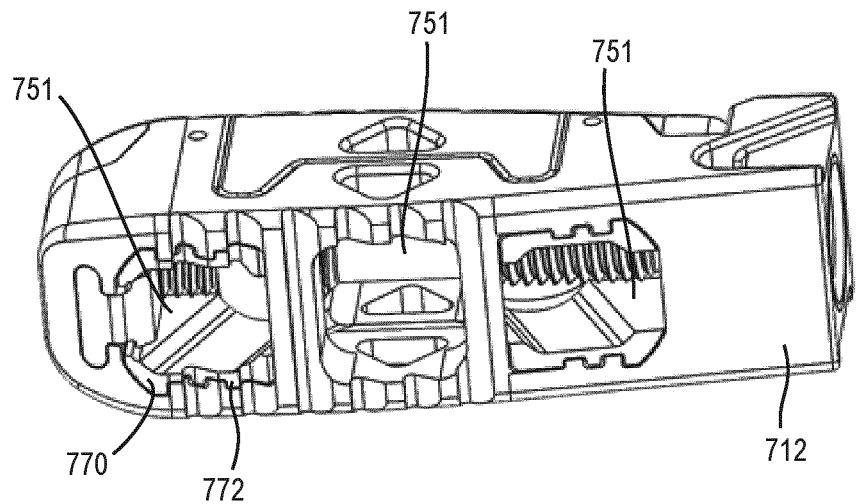
FIG. 52 is a bottom perspective view of the implant of FIG. 45 according to one embodiment.
Figure 53:
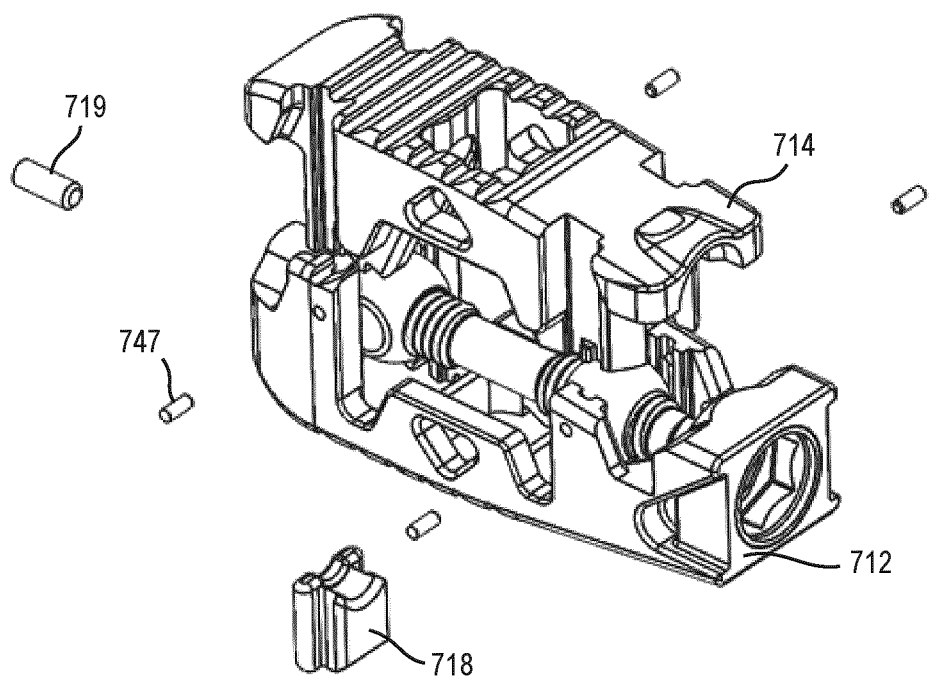
FIG. 53 is a partial exploded view of the implant of FIG. 45 according to one embodiment.

Referring to FIG. 50, in one embodiment, the adjustable member 714 includes one or more control channels, such as a first control channel 774 and a second control channel 776. The first control channel 774 receives the first control member 720, and the second control channel 776 receives the second control member 722. In some embodiments, the control members 720, 722 are received in the control channels 774, 776 in a sliding manner such that the control members 720, 722 are able to translate within the control channels 774, 776. In further embodiments, each control channel has a shape such that the control channel surrounds the control member and at least partially corresponds in shape to the control member. In some embodiments, retention member 718 includes a surface 761 (see FIG. 47) that acts as a limit surface for first control member 720, such that first control member 720 engages surface 761 at a maximum expansion position for adjustable member 714. As such, surface 761 acts to limit the maximum expansion of adjustable member 714 by limiting the degree of movement of first control member 720 (and therefore second control member 722) along control shaft 716.

Referring further to FIG. 50, the control shaft 716 includes a head portion 790, a tool port 792 disposed within the head portion 790, and a retention groove 798 located at an end opposite the head portion 790. In some embodiments, the control shaft 716 further includes a first control thread 794 and a second control thread 796. A non-threaded portion 800 may be located between the first control thread 794 and the second control thread 796.

Similar to control member 20 (see, e.g., FIGS. 1-8), the first control member 720 includes a body, one or more flat portions, and a first internal thread. Similar to control member 22 (see, e.g., FIGS. 1-8), the second control member 722 includes a body, one or more flat portions, and a second internal thread. In some embodiments, the second control member 722 further includes a slotted portion configured to enable passing the second control member 722 over a portion (e.g., non-threaded portion 800) of the control shaft 716. The first control member 720 and the second control member 722 move or translate both along the control shaft 716 and within or on the first control channel 774 and the second control channel 776.

Referring back to FIGS. 45 and 46, implant 710 is movable between a first, collapsed position, as shown in FIG. 45, to a second, expanded position, shown in FIG. 46. In the first position, the adjustable member 714 is collapsed against the base member 712. The alignment guides 741 and alignment recesses 742 on base member 712 are received by alignment recesses 780 and alignment guides 782 on adjustable member 714. In some embodiments, the alignment guides and recesses have a relatively close fit to enable proper alignment between the adjustable member 714 and the base member 712, while in other embodiments, the alignment guides and recesses have a relatively loose fit to enable a desired angular offset between the adjustable member 714 and the base member 712.

Referring to FIG. 50, the control shaft 716 is received by the base member 712 such that the retention groove 798 is positioned with the first end 724 of the base member 712 and the head portion 790 is positioned within the second end 726 of the base member 712. In one embodiment, the control shaft 716 is rotatable within the base member 712, and the retention member 718 extends through the first end 724 and into the retention groove 798 of the control shaft 16 to enable rotation of the control shaft 716 while inhibiting translation of the control shaft 716 relative to the base member 712. The first control member 720 is received on the first control thread 794 of the control shaft 716, and the second control member 722 is received on the second control thread 796 of the control shaft 716. To facilitate assembly of implant 710, in some embodiments, a slot enables passage of the second control member 722 over the non-threaded portion 800 of the control shaft 716 and subsequent threading of the second control member 722 onto the second control thread 796 (as discussed with respect to, for example, control member 22 shown in FIGS. 1-8).

In one embodiment, the first control thread 794 and the second control thread 796 are threaded in opposite manners (e.g., left-handed and right-handed), such that upon rotation of the control shaft 716, the control members 720, 722 move in opposite directions along the control shaft 716. For example, the control shaft 716 may be configured such that rotation of the control shaft 716 in a first direction (e.g., clockwise) causes the first and second control members 720, 722 to move toward each other, and rotation of the control shaft 716 in a second direction (e.g., counter-clockwise) causes the first and second control member 720, 722 to move away from each other. In other embodiments, the first and second control members 720, 722 are configured to translate in a same direction upon rotation of control shaft 716.

As shown in FIG. 50, as the control members 720, 722 move along the control shaft 716, the control members 720, 722 further move within the control channels 774, 776, thereby causing relative movement of the adjustable member 714 and the base member 712. As the control members 720, 722 translate along the control shaft 716, the adjustable member 714 is moved upward or downward due to the angled shape of the first and second control channels 774, 776. The rate of movement of the control members 720, 722, and therefore the adjustable member 714, can be adjusted by modifying the slope of the control channels 774, 776 relative to the control shaft 716, as discussed in greater detail with respect to FIGS. 9A-9C.

Providing differing configurations for the first control channel 774 and the second control channel 776 enables customization of the characteristics of the implant 710 in the second, expanded position. For example, the control channels 774, 776 may be configured such that in a fully expanded position of implant 710, one of the first end 762 and the second end 764 of the adjustable member 714 is expanded to a greater degree than the opposing end. An example of such a configuration is reflected in FIG. 9C, and shown in greater detail with the embodiment of FIGS. 27-34. Other configurations of the first and second control channels 774, 776 are possible according to various alternative embodiments. All such modifications and features are to be understood to be within the scope of the present disclosure and may form part of any of the expandable implants disclosed herein.

In use, implant 710 is positioned within a desired space (e.g., between adjacent portions of bone) while in the first, collapsed position, as shown in FIG. 45. To position implant 710, an appropriate tool may be used to engage tool recesses 756 and manipulate implant 710 into a desired position. Once in a desired position, a subsequent tool may be utilized to engage tool port 792 and rotate control shaft 716 to move adjustable member 714 to a desired degree of expansion. It should be noted that based on a particular application, the adjustable member 714 may be utilized in a fully collapsed position, a fully expanded position, or any intermediate position therebetween.

Figure 49:
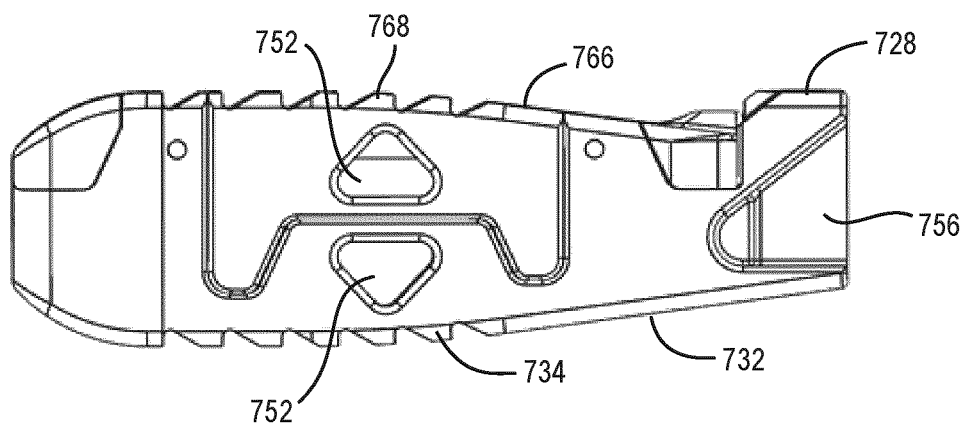
FIG. 49 is a side view of the implant of FIG. 45 according to one embodiment.

Once implant 710 is properly positioned and expanded to a desired height, bone graft material may be delivered by way of, for example, access aperture 752 (see FIG. 49) and placed into central cavity 736. The various apertures in and through the base member 712 and adjustable member 714 may in some embodiments facilitate the growth of bone material in and around implant 710 to further stabilize the device. As shown in FIG. 49, side apertures 752 may extend through one or both sides of the base member 712 and the adjustable member 714 and communicate with an interior of implant 710 to promote bone growth, etc. Similarly, aperture 784 in adjustable member 714 and apertures 751 in the base member 712 provide access to the interior of implant 710 via the top/bottom of implant 710. Further, control member 716 may include an access port 791 accessible by way of tool port 792 that is in fluid communication with the interior of implant 710 and enables delivery of bone graft or other material to the interior of implant 710 (e.g., by way of a tool, etc.).

It should be noted that implant 710 may share various features with the other implants described herein, and be made of the same, similar, or different materials. For example, various components of implant 710 may be made of metal, plastic, composites, or other suitable bio-compatible materials. Further, implant 710 may be usable in connection with the spine or other parts of the body.

Figure 55:
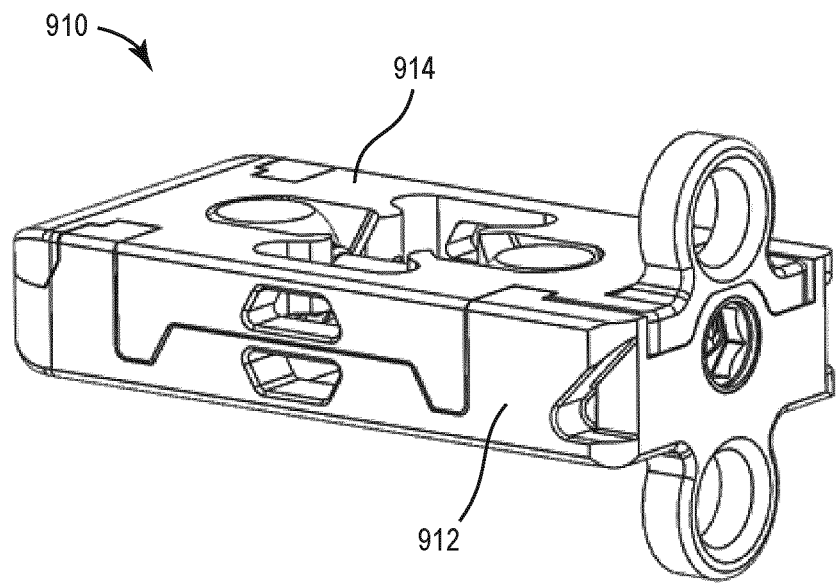
FIG. 55 is a perspective view of an expandable implant in a collapsed position according to another embodiment.
Figure 56:
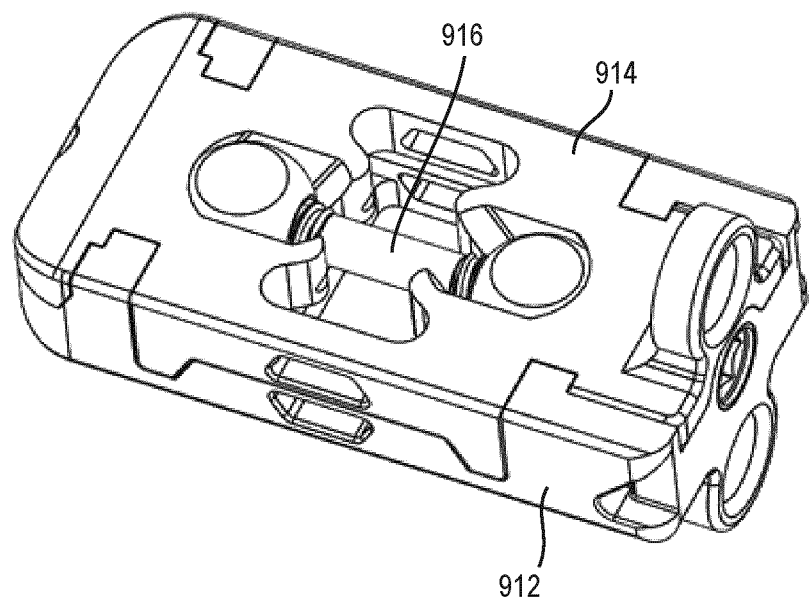
FIG. 56 is another perspective view of the implant of FIG. 55 in a collapsed position according to one embodiment.
Figure 57:
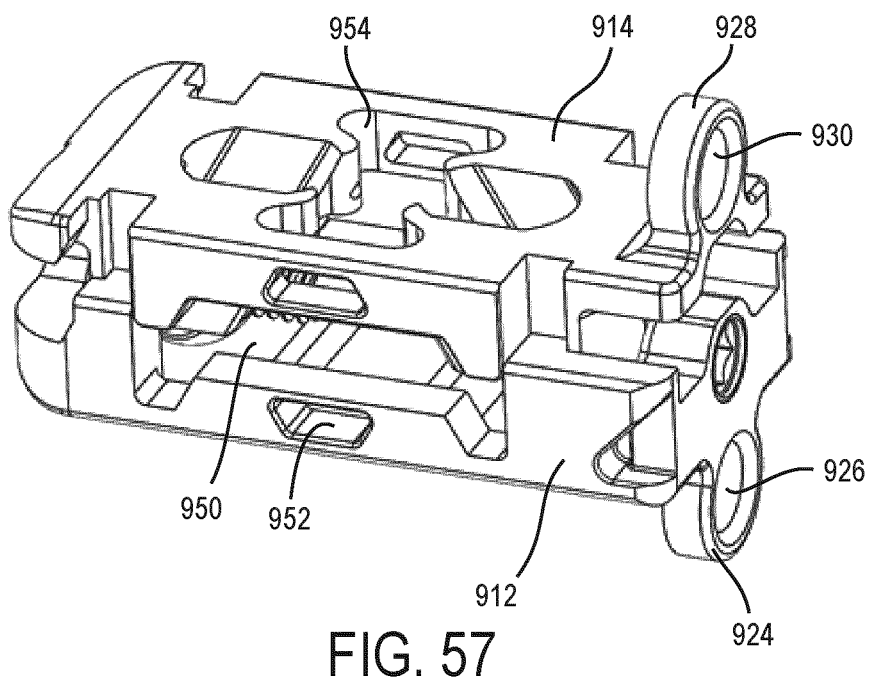
FIG. 57 is a perspective view of the implant of FIG. 55 in an expanded position according to one embodiment.
Figure 58:
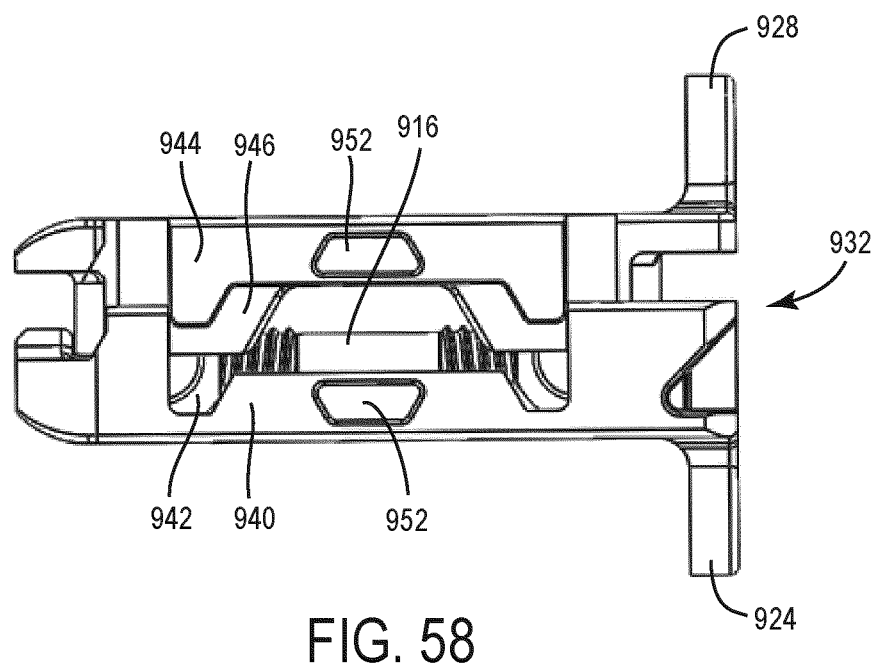
FIG. 58 is a side view of the implant of FIG. 55 in an expanded embodiment.
Figure 59:
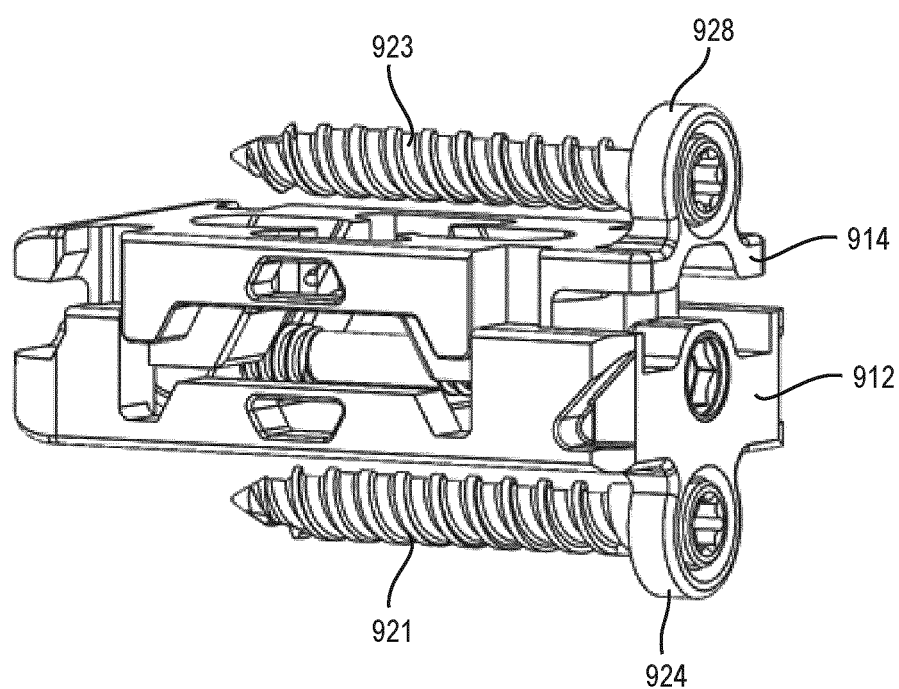
FIG. 59 is a perspective view of the implant of FIG. 55 with bone screws inserted according to one embodiment.

Referring now to FIGS. 55-59, in some embodiments, one or both of a base member or an adjustable member of an implant may be configured to receive a bone screw to further secure the implant to adjacent portions of bone. For example, as shown in FIGS. 55-59, an implant 910 includes a base member 912 and an adjustable member 914 is adjustably coupled to the base member 912. A control shaft 916 is received by the base member 912 and may be retained by a retention pin passing through a portion of the base member 912. A first control member 920 and a second control member 922 are received on the control shaft 916 and are movable along the control shaft 916 to adjust a position of the adjustable member 914 between a collapsed position, as shown in FIGS. 55-56, and an expanded position, as shown in FIGS. 57-59. Bone screws 921, 923 extend through base member 912 and adjustable member 914 (see FIG. 59).

Implant 910 may include any combination of the features disclosed herein with respect to the other implants, and all such combinations of features are to be understood to be within the scope of the present disclosure, particularly, but not limited to, those features of implant 310 shown and described with respect to FIGS. 16-18. In one embodiment, a substantial portion of implant 910 is generally rectangular in shape when in a first, collapsed position. As shown in FIGS. 57-59, in some embodiments, the base member 912 includes a first bone screw support portion or extension 924 having a first bone screw bore 926 configured to receive bone screw 921. Similarly, adjustable member 914 includes a second bone screw support portion or extension 928 having a second bone screw bore 930 configured to receive bone screw 923. The first extension 924 and the second extension 928 collectively form a proximal face 932 (see FIG. 58) for implant 910 with the corresponding end portions of base member 912 and adjustable member 914. As shown in FIG. 58, the first bone screw bore 926, the second bone screw bore 930, and the control shaft 916 are accessible by way of the proximal face 932 of the implant 910.

Referring further to FIG. 58, in some embodiments, extensions 924, 928 extend in generally opposite directions relative to the remaining portions of the base member 912 and the adjustable member 914 (e.g., in a perpendicular fashion, in an angled fashion, etc.). As such, extensions 924, 928 may act as to limit the insertion of implant 910 into a vertebral or other space by way of extensions 924, 928 interfacing with adjacent portions of bone. Furthermore, extensions 924, 928 and bone screw bores 926, 930 may be configured such that bone screws 921, 923 extend in a generally parallel manner to the longitudinal axis of implant 910 (see FIG. 59). This configuration may facilitate fastening screws 921, 923 into adjacent portions of bone due to the alignment of the screws with an incision and/or the implant.

In some embodiments and similar to various other implants disclosed herein, implant 910 may include lower alignment guides 940 and lower alignment recesses 942 provided on base member 912 that are configured to be received by corresponding upper alignment recesses 946 and upper alignment guides 944 provided on adjustable member 914 to maintain a desired alignment (e.g., linear, non-linear, etc.) between adjustable member 914 and base member 912. The alignment guides and recesses may be provide on both sides of implant 910, and any suitable number of guides and recesses may be utilized. Further, implant 910 includes a central cavity 950 that is accessible (e.g., to promote bone growth, to receive bone growth material, etc.) by way of side apertures 952, which may be provide on one or both sides of base member 912 and/or adjustable member 914. Implant may further include a top aperture 954 to provide access to the central cavity 950.

As shown in FIGS. 55-59, implant 910 may have a relatively flat profile, such that the width of the implant 910 is substantially greater than the height of the main portion or body of implant 910 excluding the extensions 924, 928. For example, in various embodiments the width of the main body of implant 910 may be two, three, four, or more times the height. A flatter profile may provide a more stable implant. Furthermore, in some embodiments, in the collapsed position, as shown in FIG. 56, the first and second control members 920, 922 may be flush with or adjacent the top and/or bottom surfaces of implant 910, and the corresponding control channels may open up to the top and/or bottom surfaces of implant 910.

It should be noted that the implant 910 may share various features with the other implants described herein, and be made of the same, similar, or different materials. For example, various components of the implant 910 may be made of metal, plastic, composites, or other suitable bio-compatible materials. Further, the implant 910 may be usable in connection with the spine or other parts of the body.

Referring now to FIGS. 60-65, an expandable implant 1010 is shown according to an exemplary embodiment. Implant 1010 may include many of the features of the other inter/intra-body implants discussed elsewhere herein, particularly implant 610 shown and described with respect to FIGS. 35-44. All such combinations of features are to be understood to be within the scope of the present disclosure. Implant 1010 is generally similar to the other implants disclosed herein in structure and function except that implant 1010 utilizes a single control member/control channel configuration, and further utilizes a pivot pin about which an adjustable member pivots relative to a base member.

Figure 60:
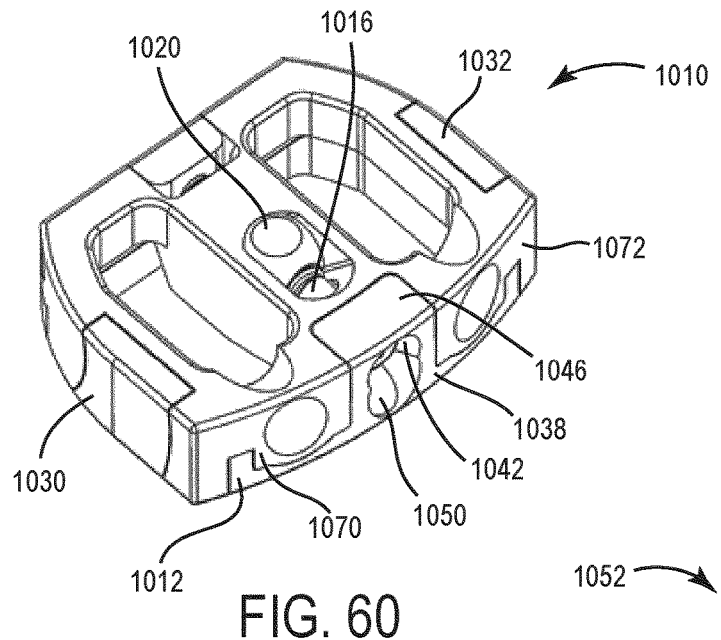
FIG. 60 is a perspective view of an expandable implant in a collapsed position according to another embodiment.

According to an exemplary embodiment, implant 1010 includes a base member 1012 and an adjustable member 1014 adjustably coupled to the base member 1012. A control shaft 1016 is received by the base member 1012 and is retained by a retention pin 1018 (e.g., a pivot pin or member, retaining pin) passing through a portion of the base member 1012 and/or the adjustable member 1014. A control member 1020 is received on the control shaft 1016 and is movable along the control shaft 1016 to adjust a position of the adjustable member 1014 between a collapsed position, as shown in FIG. 60, and an expanded position, as shown in FIG. 61.

In one embodiment, the base member 1012 includes a front or first end 1024, a rear or second end 1026, and a central cavity 1039 disposed between the first end 1024 and the second end 1026. The base member 1012 further includes a top surface 1046 and a bottom surface 1034 opposite the top surface 1046. The top and bottom surfaces 1046, 1034 may include ridges or projections formed by corresponding grooves, as similarly shown in FIGS. 35-44. The projections are configured to engage adjacent portions of bone. The base member 1012 further includes a bottom portion 1028. A first extension 1030 is positioned at a first side and extends upward from the bottom portion 1028, and a second extension 1032 is positioned at a second side and extends upward from the bottom portion 1028. Extensions 1030, 1032 include curved lateral surfaces 1033 (see FIG. 61) configured to engage corresponding curved surfaces 1035 (see FIG. 63) within recesses 1036 formed in adjustable member 1014 to maintain a desired pivotal alignment during movement of adjustable member 1014. A pin aperture 1068 extends through the bottom portion 1028 and is configured to receive the retention pin 1018 (e.g., in a press fit, sliding, or other manner). A front extension 1038 includes a bone screw bore 1050 configured to receive a bone screw 1022. The front extension 1038 includes a control bore 1042 configured to receive a head portion of the control shaft 1016.

Figure 61:
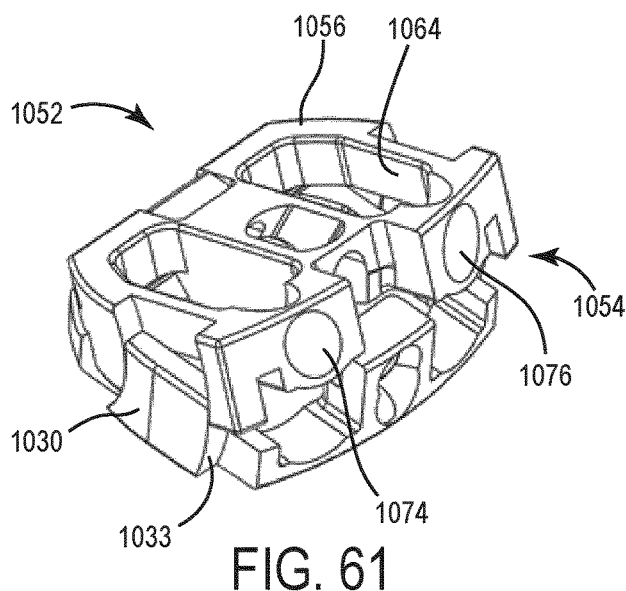
FIG. 61 is a perspective view of the implant of FIG. 60 in an expanded position according to one embodiment.

In one embodiment, the adjustable member 1014 includes a front or first end 1052, a rear or second end 1054, and cavities 1064 extending through the adjustable member 1014 and positioned between the first end 1052 and the second end 1054 (see FIG. 61). The adjustable member 1014 further includes a top surface 1056 that may include ridges or projections formed by corresponding grooves. The adjustable member 1014 further includes pin apertures 1068 (see FIG. 65) configured to receive the retention pin 1018 to enable movement (e.g., pivoting) of the adjustable member 1014 relative to the base member 1012. Further, the adjustable member includes a first bone screw support portion 1070 including a bone screw bore 1074 and a second bone screw support portion 1072 having a bone screw bore 1076. As shown in FIG. 60, the first and second bone screw support portions 1070, 1072 of the adjustable member 1014 and the front extension 1038 of the base member 1012 collectively form a front face of the implant 1010, such that the control shaft 1016 and the bone screws 1022 are accessible via the front face of the implant 1010 (e.g., when the implant 1010 is in a collapsed position). Furthermore, the first and second bone screw support portions 1070, 1072 and the front extension 1038 may be sized and spaced relative to each other so as to prevent undesired relative lateral movement between base member 1012 and adjustable member 1014.

In one embodiment, the adjustable member 1014 includes one or more control channels, such as control channel 1062. The control channel 1062 receives the control member 1020. In some embodiments, the control member 1020 is received in the control channel 1062 in a sliding manner such that the control member 1020 is able to translate within the control channel 1062. In further embodiments, the control channel 1062 has a shape such that the control channel 1062 surrounds the control member 1020 and at least partially corresponds in shape to the control member 1020.

The control shaft 1016 may include the features of control shaft 616 disclosed herein, and may include a head portion, a tool port disposed within the head portion, and a retention groove located at an end opposite the head portion. In some embodiments, the control shaft 1016 further includes a control thread 1082. Non-threaded portions may be located on one or both side of the control thread 1082. The control member 1020 may include the features of control member 620, and may include a body, one or more flat portions, and an internal thread. In some embodiments, the control member 1020 further includes a slotted portion configured to enable passing the control member 1020 over a portion (e.g., a non-threaded portion) of the control shaft 1016. The control member 1020 moves or translates both along the control shaft 1016 and within or on the control channel 1062.

Figure 62:
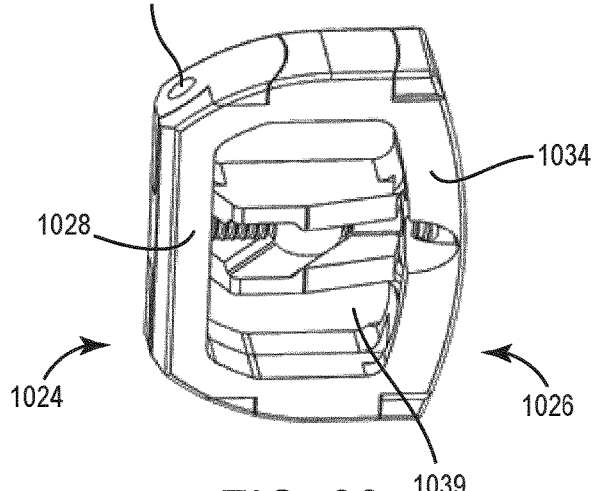
FIG. 62 is a bottom perspective view of the implant of FIG. 60 in an expanded position according to one embodiment.
Figure 63:
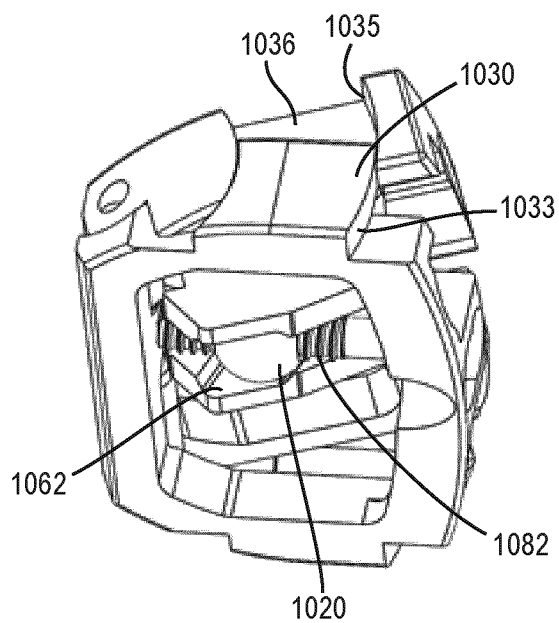
FIG. 63 is another bottom perspective view of the implant of FIG. 60 in an expanded position according to one embodiment.

Referring further to FIGS. 60-62, the control shaft 1016 is received by the base member 1012 such that the head portion of control shaft 1016 is positioned within the front extension 1038 of the base member 1012. In one embodiment, the control shaft 1016 is rotatable within the base member 1012, and a retention pin (e.g., retention pin 1018) extends into a retention groove of the control shaft 1016 to enable rotation of the control shaft 1016 while inhibiting translation of the control shaft 1016 relative to the base member 1012. The internal thread of the control member 1020 is received on the control thread 1082 of the control shaft 1016 such that as the control member 1020 moves along the control shaft 1016, the control member 1020 further moves within the control channel 1062, thereby causing relative movement (e.g., pivotal movement) of the adjustable member 1014 relative to the base member 1012 (e.g., about retention pin 1018). As the control member 1020 translates along the control shaft 1016, the adjustable member 1014 pivots about the retention pin 1018. The rate of movement of the control member 1020, and therefore the adjustable member 1014, can be adjusted by modifying the slope of the control channel 1062 relative to the control shaft 1016.

Figure 64:
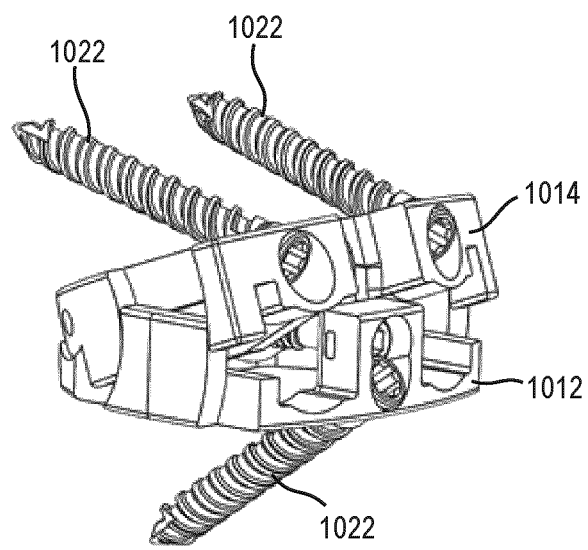
FIG. 64 is side perspective view of the implant of FIG. 60 in an expanded position with bone screws inserted according to one embodiment.
Figure 65:
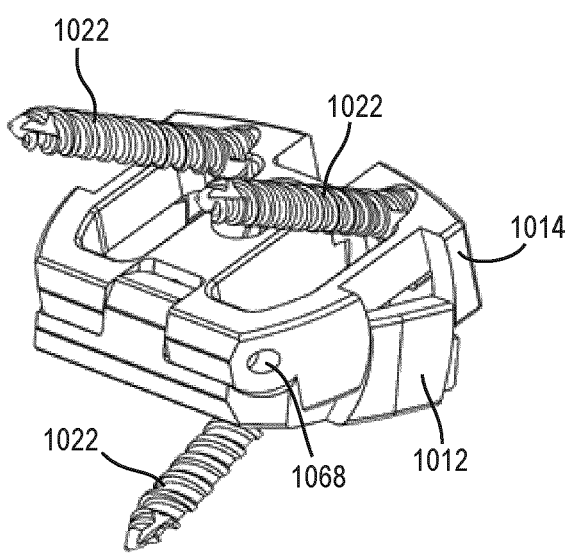
FIG. 65 is a rear perspective view of the implant of FIG. 60 in an expanded position with bone screws inserted according to another embodiment.

In use, implant 1010 is positioned within a desired space (e.g., between adjacent portions of bone) while in the first, collapsed position, as shown in FIG. 60. To position implant 1010, an appropriate tool may be used to engage tool recesses (similar to tool recesses 648) and manipulate implant 1010 into a desired position. Once in a desired position, a subsequent tool may be utilized to engage control shaft 1016 to pivot adjustable member 1014 to a desired degree of expansion. It should be noted that based on a particular application, the adjustable member 1014 may be utilized in a fully collapsed position, a fully expanded position, or any intermediate position therebetween. One or more bone screws 1022 may be screwed into adjacent portions of bone as shown in FIG. 64. Once implant 1010 is properly positioned and expanded to a desired height, bone graft material may be delivered by way of, for example, apertures 1064 or alternatively, by the space formed due to the expansion of adjustable member 1014. The various apertures in and through the base member 1012 and adjustable member 1014 may in some embodiments facilitate the growth of bone material in and around implant 1010 to further stabilize the device.

It should be noted that implant 1010 may share various features with the other implants described herein, and be made of the same, similar, or different materials. For example, various components of implant 1010 may be made of metal, plastic, composites, or other suitable bio-compatible materials. Further, implant 1010 may be usable in connection with the spine or other parts of the body.

Referring now to FIGS. 66-69, an expandable implant 1110 is shown according to an exemplary embodiment. Implant 1110 may include many of the features of the other inter/intra-body implants discussed elsewhere herein, particularly those features of implant 210 shown and described with respect to FIGS. 10-15. All such combinations of features are to be understood to be within the scope of the present disclosure. Implant 1110 is generally similar to implant 210 in structure and function except that implant 1110 includes extensions to receive bone screws.

Figure 66:
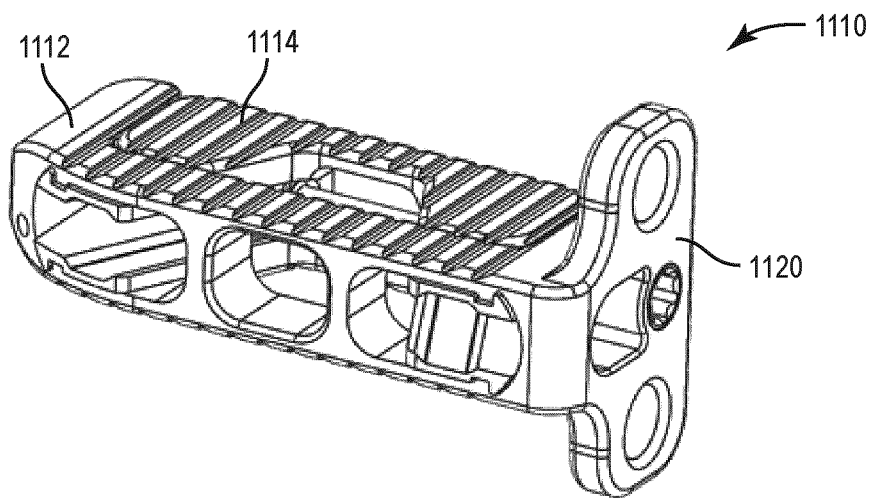
FIG. 66 is a perspective view of an expandable implant in a collapsed position according to one embodiment.
Figure 67:
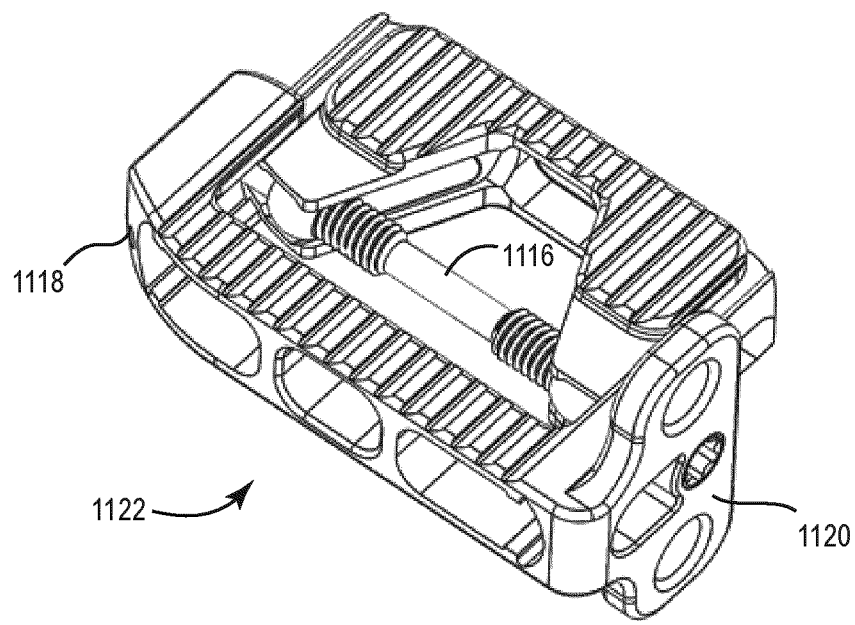
FIG. 67 is a perspective view of the implant of FIG. 66 in an expanded position according to one embodiment.
Figure 68:
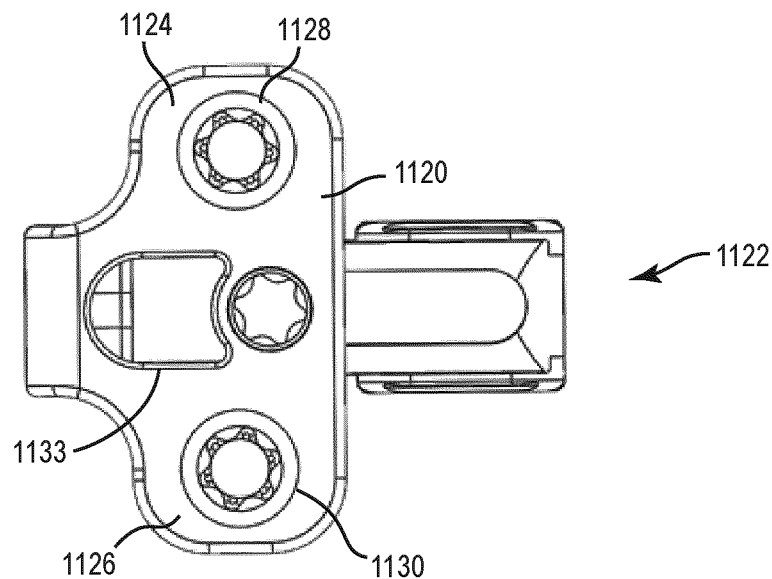
FIG. 68 is a front view of the implant of FIG. 66 in an expanded position according to one embodiment.
Figure 69:
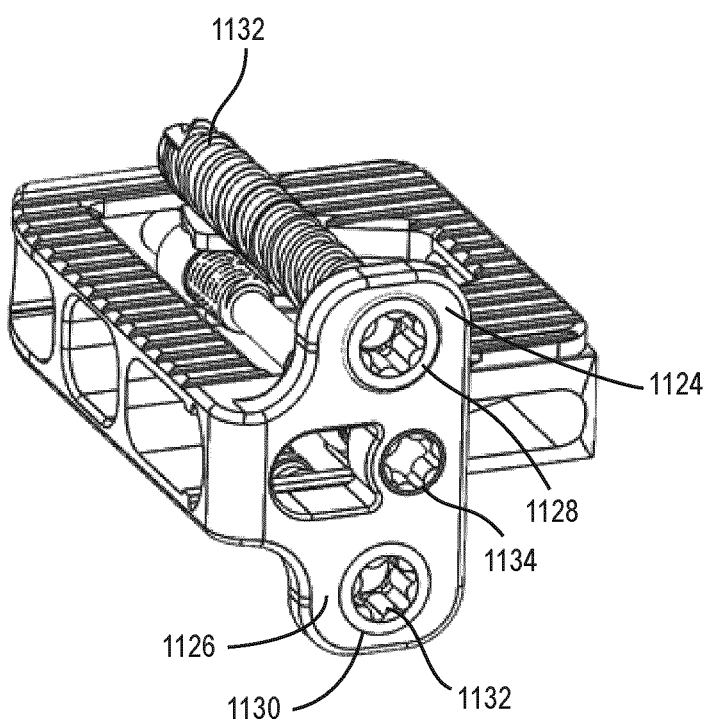
FIG. 69 is a perspective view of the implant of FIG. 66 in an expanded position with bone screws inserted according to one embodiment.

Implant 1110 includes a base member 1112 and an adjustable member 1114 adjustably coupled to the base member 1112. A control shaft 1116 is received by the base member 1112 and is retained by a retention pin 1118 passing through a portion of the base member 1112. A first control member and a second control member are received on the control shaft 1116 and are movable along the control shaft 1116 to adjust a position of the adjustable member 1114 between a collapsed position, as shown in FIG. 66, and an expanded position, as shown in FIG. 67.

In addition to those features discussed with respect to implant 210, any of which may be included as part of implant 1110, implant 1110 further includes a flange portion or extension 1120. Extension 1120 extends from a main body portion 1122 of base member 1112 and includes an upper extension 1124 and a lower extension 1126. Upper extension 1124 includes a first bone screw bore 1128, and lower extension 1126 includes a second bone screw bore 1130. Extension 1120 further includes an aperture 1133 and a control bore 1134.

Implant 1110 is adjustable in a similar manner to implant 10. However, while adjustment of implant 10 causes a change in height of the implant 10, adjustment of the implant 1110 causes a change in width of the implant 1110 (while maintaining a constant height). As such, while during adjustment of the implant 10, the top surface of the adjustable member 14 may be offset from the top surface of the base member 12, during adjustment of implant 1110, the top surface of the adjustable member 1114 stays generally aligned with the top surface of the base member 1112. The implant 1110 may be used to provide, for example, a more stable implant by increasing the footprint of the implant and engagement areas with adjacent portions of bone. The implantation of the implant 1110 is otherwise similar to that of the implant 10 and the other implants noted herein.

In some embodiments, extensions 1124, 1126 extend in generally opposite directions relative to main portion 1122 of the base member 1112 (e.g., in a perpendicular fashion, in an angled fashion, etc.). As such, extensions 1124, 1126 may act as to limit the insertion of implant 1110 into a vertebral or other space by way of extensions 1124, 1126 interfacing or interfering with adjacent portions of bone. Furthermore, extensions 1124, 1126 and bone screw bores 1128, 1130 may be configured such that bone screws 1132 extend in a generally parallel manner to the longitudinal axis of implant 1110 (see FIG. 69). This configuration may facilitate fastening bone screws 1132 into adjacent portions of bone due to the alignment of the screws with an incision and/or the implant.

It should be noted that the implant 1110 may share various features with the other implants described herein, and be made of the same, similar, or different materials. For example, various components of implant 1110 may be made of metal, plastic, composites, or other suitable bio-compatible materials. Further, implant 1110 may be usable in connection with the spine or other parts of the body.

Referring now to FIGS. 70-78, an expandable implant 1210 is shown according to an exemplary embodiment. The implant 1210 is usable, for example, between and/or within vertebral bodies of the spine, and may include any or all of the features of the other inter/intra-body implants discussed elsewhere herein. All such combinations of features are to be understood to be within the scope of the present disclosure. It should be understood that the implant 1210 may in some embodiments be usable in other portions of the body in addition to the spine, and all such applications are to be understood to be within the scope of the present disclosure. The implant 1210 is in many ways similar to implant 510, and may include any of the features of implant 510 or the other implants disclosed herein.

Figure 70:
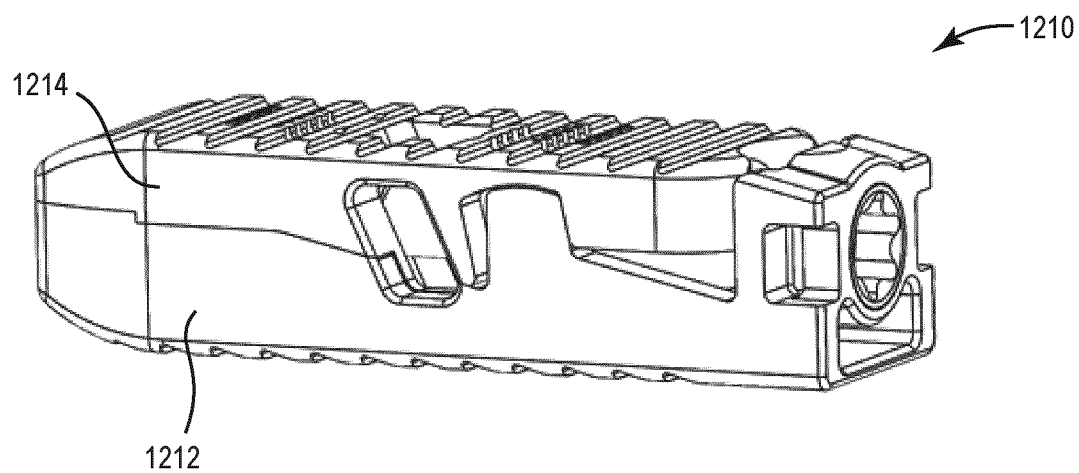
FIG. 70 is a side perspective view of an expandable implant in a collapsed position according to one embodiment.
Figure 71:
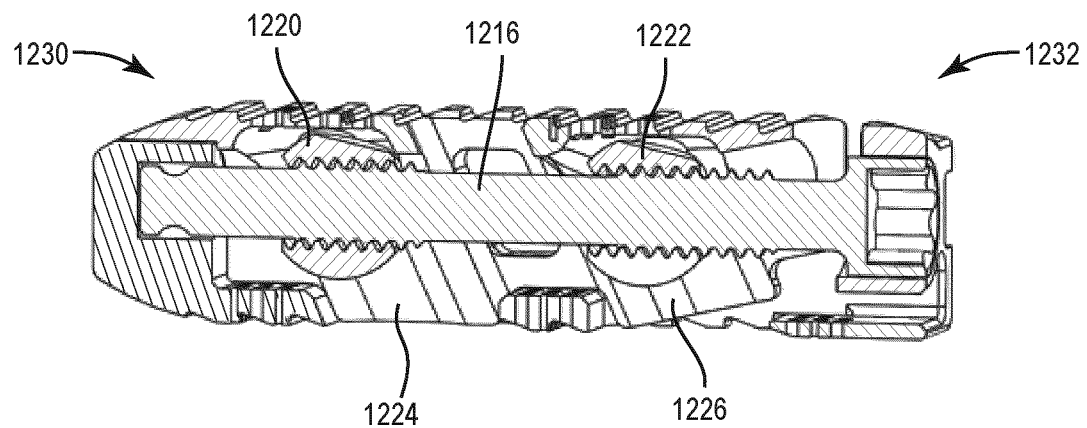
FIG. 71 is a cross section view of the implant of FIG. 70 is a collapsed position according to one embodiment.
Figure 74:
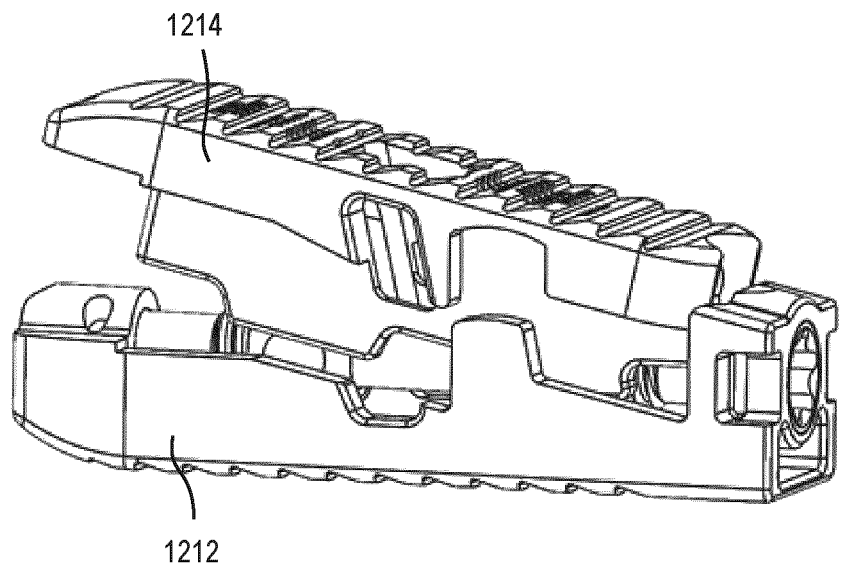
FIG. 74 is side perspective view of the implant of FIG. 70 in an expanded position according to one embodiment.
Figure 75:
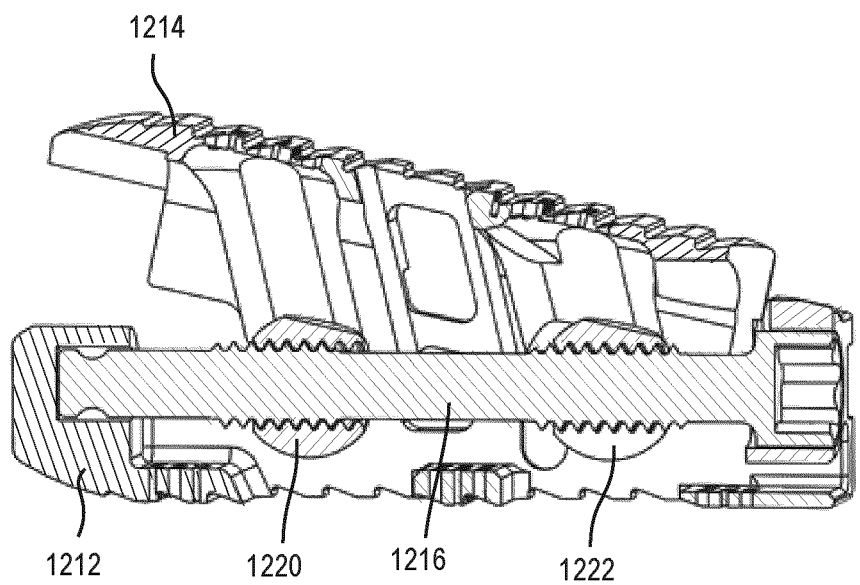
FIG. 75 is a cross section view of the implant of FIG. 70 in an expanded position according to one embodiment.
Figure 76:
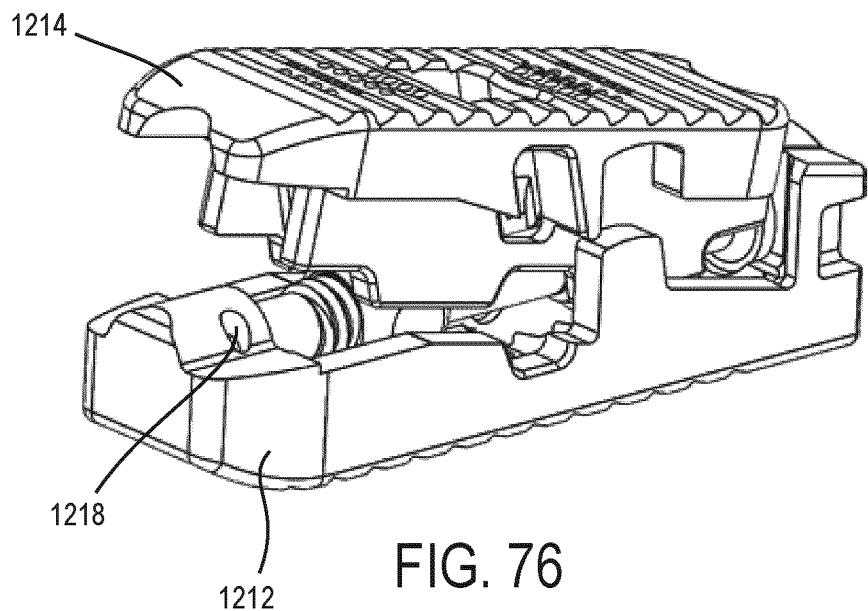
FIG. 76 is another perspective view of the implant of FIG. 70 in an expanded position according to one embodiment.

According to an exemplary embodiment, the implant 1210 includes a base member 1212 and an adjustable member 1214 adjustably coupled to the base member 1212. A control shaft 1216 is received by the base member 1212 and is retained by a retention pin 1218 passing through a portion of the base member 1212. A first control member 1220 and a second control member 1222 are received on the control shaft 1216 and are movable along the control shaft 1216 to adjust a position of the adjustable member 1214 between a collapsed position, as shown in FIGS. 70-71, and an expanded position, as shown in FIGS. 74-75. In some embodiments, expansion due to the control shaft 1216 may enable fluid communication (e.g., for the delivery of bone growth material, etc.) between an exterior and an interior of implant 1210.

In one embodiment, the adjustable member 1214 includes a front or first end 1230, and a rear or second end 1232. The adjustable member 1214 further includes one or more control channels, such as a first control channel 1224 and a second control channel 1226. The first control channel 1224 receives the first control member 1220, and the second control channel 1226 receives the second control member 1222. In some embodiments, the control members 1220, 1222 are received in the control channels 1224, 1226 in a sliding manner such that the control members 1220, 1222 are able to translate within the control channels 1224, 1226. In further embodiments, each control channel has a shape such that the control channel surrounds the control member and at least partially corresponds in shape to the control member.

As shown in FIGS. 71-75, as the control members 1220, 1222 move along the control shaft 1216, the control members 1220, 1222 further move within the control channels 1224, 1226, thereby causing relative movement of the adjustable member 1214 and the base member 1212. As the control members 1220, 1222 translate along the control shaft 1216, the adjustable member 1214 is moved based on the shape of the first and second control channels 1224, 1226. The rate of movement of the control members 1220, 1222, and therefore the adjustable member 1214, can be adjusted by modifying the slope of the control channels 1224, 1226 relative to the control shaft 1216.

Figure 77:
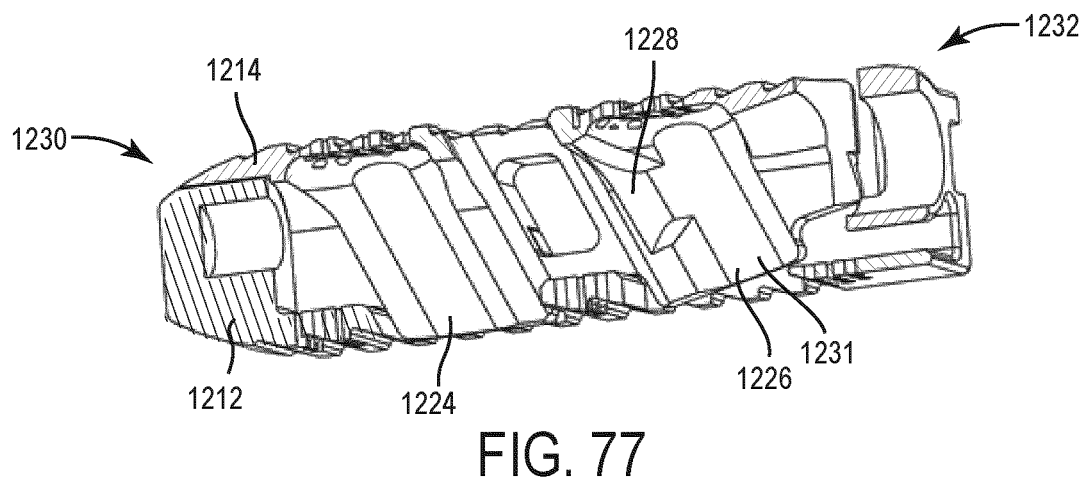
FIG. 77 is a partial cutaway view of the implant of FIG. 70 according to one embodiment.

For example, as shown in FIG. 77, the first control channel 1224 extends at an angle relative to the control shaft 1216, and has a substantially linear form and constant slope, thereby providing a generally constant corresponding rate of movement of the first end 1230 of the adjustable member 1214. The second control channel 1226 includes a first channel portion 1228 and a second channel portion 1231 which extend at different angles relative to the control shaft 1216. As shown in FIG. 34, the first channel portion 1228 is generally parallel to the control shaft 1216, and the second channel portion 1231 extends at an angle similar to that of first control channel 1224. As such, the second control channel 1226 provides a non-constant rate of movement of second end 1232 of the adjustable member 1214.

Figure 72:
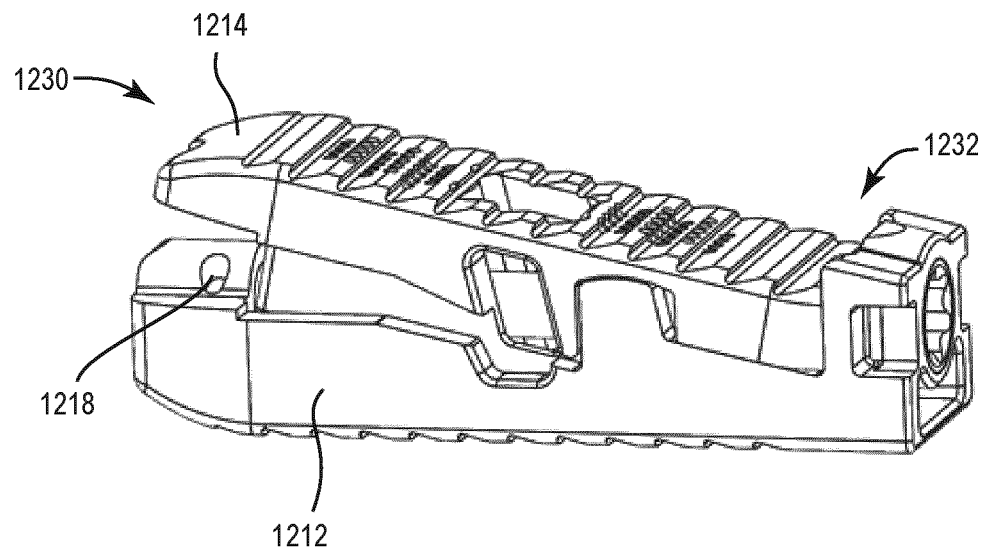
FIG. 72 is a side perspective view of the implant of FIG. 70 in an intermediate position according to one embodiment.
Figure 73:
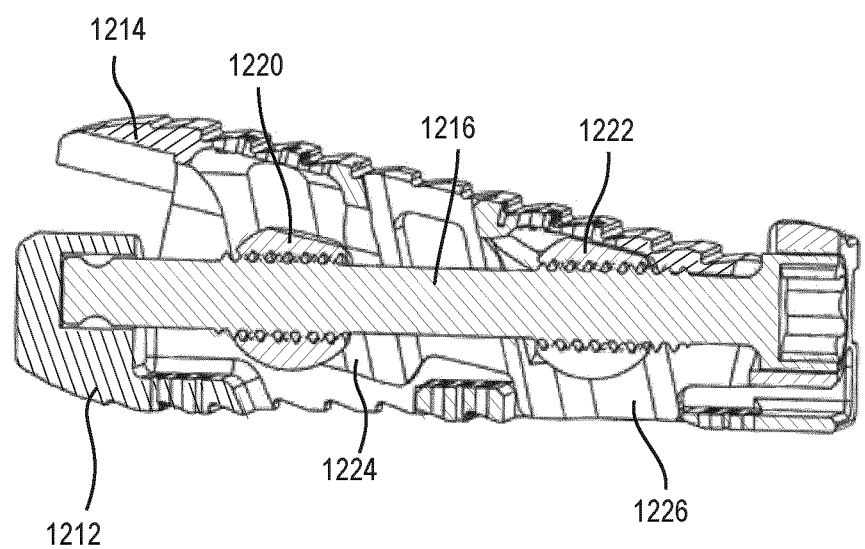
FIG. 73 is a cross section view of the implant of FIG. 70 in an intermediate position according to one embodiment.

FIGS. 70-75 illustrate the corresponding movement of the adjustable member 1214 resulting from the differing configurations of the first control channel 1224 and the second control channel 1226. In FIGS. 70-71, the implant 1210 is in a collapsed position, such that the control members 1220, 1222 reside in the upper positions within the first and second control channels 1224, 1226. FIGS. 72-73 illustrate implant 1210 in an intermediate expanded position, where second control member 1222 is positioned generally at the intersection of the first channel portion 1228 and the second channel portion 1231. Due to the orientation of the first channel portion 1228, the second end 1232 of adjustable member 1214 has moved downward relative to the height as that shown in FIGS. 70-71, while due to the configuration of first control channel 1224, the first end 1230 of the adjustable member 1214 has moved upward relative to the base member 1212. FIGS. 74-75 show the implant 1210 in a fully expanded position, where control members 1220, 1222 reside in the lower/outer—most positions within the first and second control channels 1224, 1226. Due to the angled configurations of both the first control channel 1224 and the second channel portion 1231 of the second control channel 1226, both the first end 1230 and the second end 1232 move relative to the base member 1212.

Figure 78:
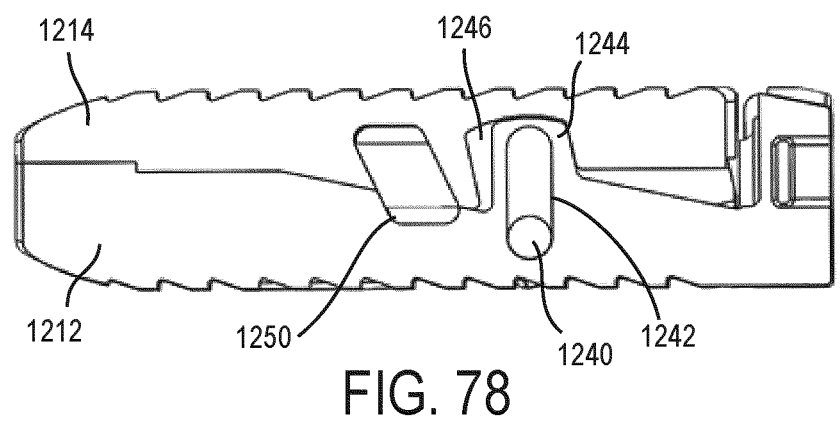
FIG. 78 is a side view of the implant of FIG. 70 according to another embodiment.

Referring to FIG. 78, in some embodiments, implant 1210 includes features intended to facilitate non-linear movement of adjustment member 1214 relative to base member 1212. For example, in one embodiment, a pin 1240 (e.g., a projection, etc.) provided on adjustment member 1214 resides within a slot 1242 (e.g., a recess, etc.) provided on base member 1212. The pin 1240 may rotate and/or translate within the slot 1242. Pin 1240 and a slot 1242 limit the range of relative motion between adjustable member 1214 and base member 1212. Further, base member 1212 may include an alignment guide 1244 (e.g., an upstanding wall portion, etc.) received within an alignment recess 1246 in adjustable member 1214. Alignment guide 1244 and alignment recess 1246 are configured such that in a first, collapsed position, a first side of alignment guide 1244 engages a first side of recess 1246 (see FIG. 70), and in an intermediate position a second side of alignment guide 1244 engages a second side of recess 1246 (see FIG. 72). In the fully expanded position, the alignment guide 1244 and recess 1246 may disengage due to the separation of the adjustable member 1214 and the base member 1212.

In one embodiment, implant 1210 includes one or more apertures intended to provide fluid communication (e.g., for the delivery of bone growth material, etc.) between an exterior and an interior of implant 1210. For example, in one embodiment, implant 1210 includes one or more apertures 1250 extending from an exterior of implant 1210 to an interior. Aperture 1250 may be formed in base member 1212, adjustable member 1214, or as shown in FIG. 78, collectively formed by members 1212, 1214.

Providing an implant with adjustment features such as those provided by implant 1210 may facilitate accommodating a desired spinal curvature or other anatomical features where non-parallel supporting surfaces are suitable for a particular application. In some embodiments, providing an implant with adjustment features such as those provided by implant 1210 may facilitate fluid delivery/fluid ingress into the implant. It should be noted that the control channels and/or control rails herein may take any desired configuration to provide desired expansion and contraction characteristics for a particular implant.

Referring now to FIGS. 79-85, an expandable implant 1310 is shown according to an exemplary embodiment. The implant 1310 is usable, for example, between and/or within vertebral bodies of the spine, and may include any or all of the features of the other inter/intra-body implants discussed elsewhere herein. All such combinations of features are to be understood to be within the scope of the present disclosure. It should be understood that the implant 1310 may in some embodiments be usable in other portions of the body in addition to the spine, and all such applications are to be understood to be within the scope of the present disclosure. The implant 1310 is in many ways similar to implant 410, and may include any of the features of implant 410 or the other implants disclosed herein.

Figure 79:
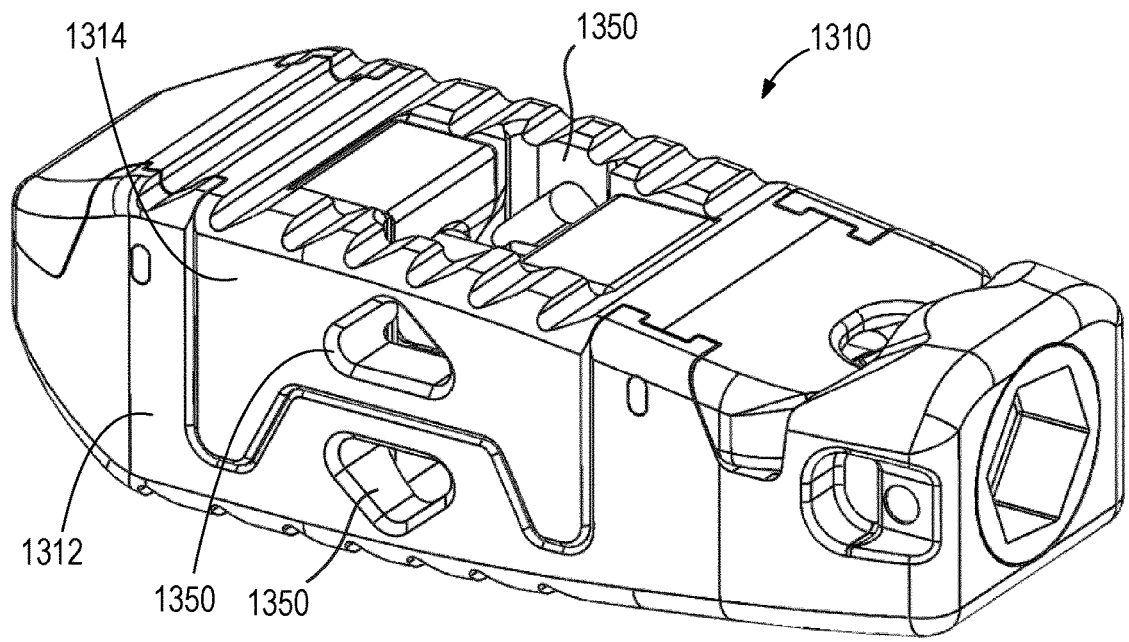
FIG. 79 is a side perspective view of an expandable implant in a collapsed position according to one embodiment.
Figure 80:
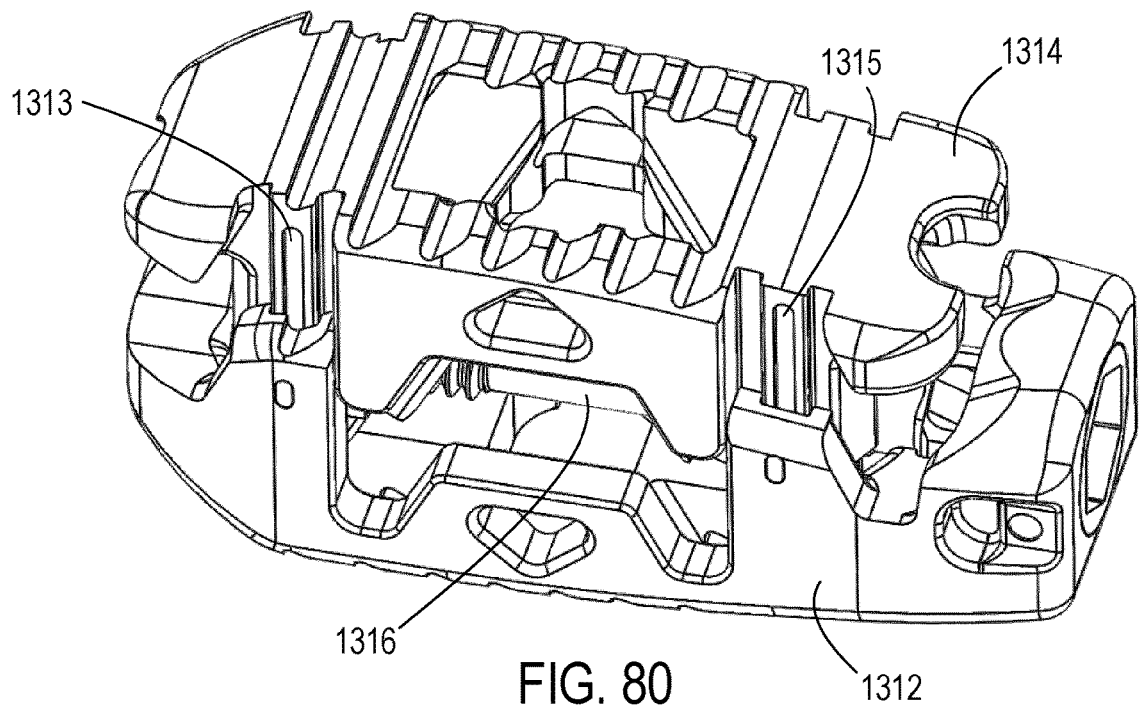
FIG. 80 is a side perspective view of the implant of FIG. 79 in an expanded position according to one embodiment.

According to an exemplary embodiment, the implant 1310 includes a base member 1312 and an adjustable member 1314 adjustably coupled to the base member 1312. A control shaft 1316 is received by the base member 1312 and is retained by a retention pin 1318 passing through a portion of the base member 1312 to be received by a groove 1321 on the control shaft 1316. The groove 1321 is configured to allow rotational motion of the control shaft 1316 while preventing lateral (e.g., side to side, in and out) translation of the control shaft 1316. A first control member 1320 and a second control member 1322 are received on the control shaft 1316 and are movable along the control shaft 1316 to adjust a position of the adjustable member 1314 between a collapsed position, as shown in FIG. 79, and an expanded position, as shown in FIG. 80.

Figure 81:
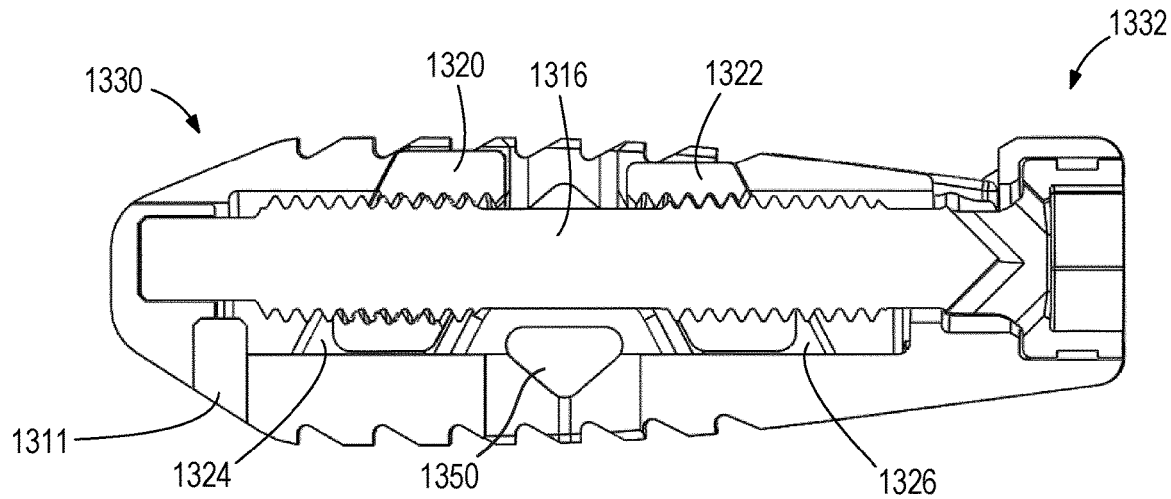
FIG. 81 is a cross section view of the implant of FIG. 79 in a collapsed position according to one embodiment.
Figure 84:
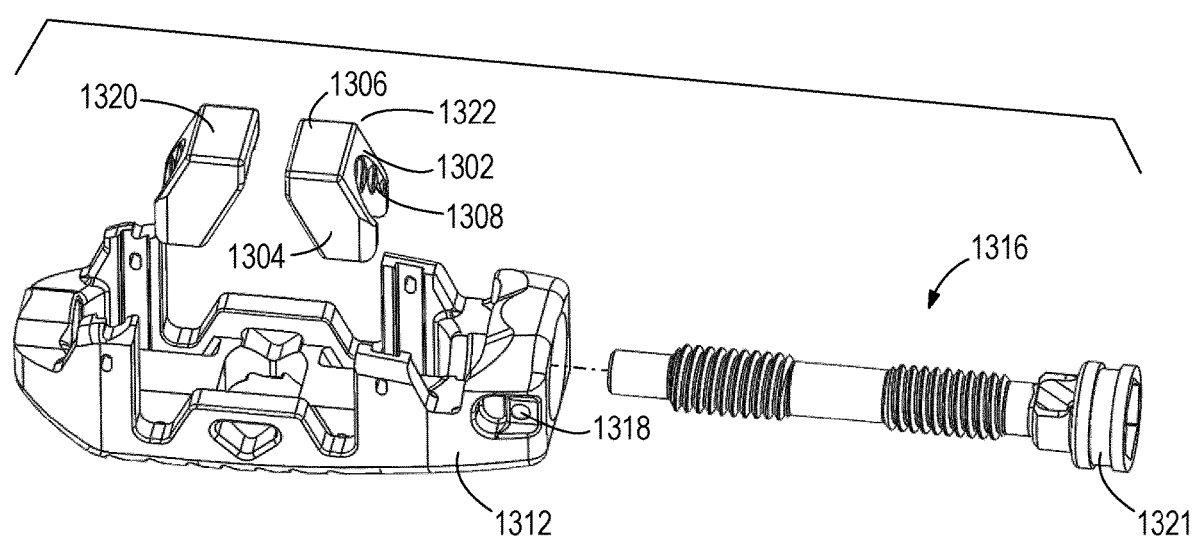
FIG. 84 is a partial exploded view of the implant of FIG. 79 according to one embodiment.
Figure 85:
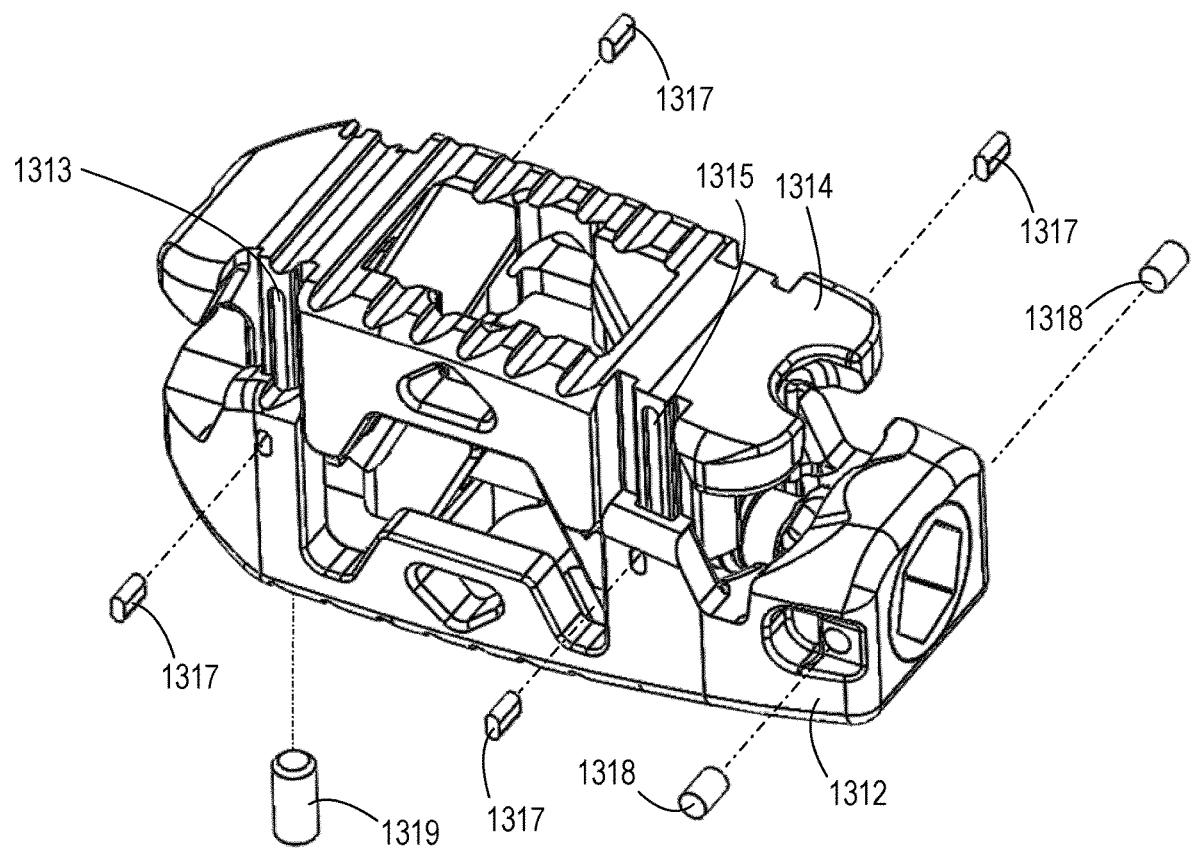
FIG. 85 is another partial exploded view of the implant of FIG. 79 according to one embodiment.

In one embodiment, the adjustable member 1314 includes a front or first end 1330, and a rear or second end 1332. The adjustable member 1314 further includes one or more control channels, such as first control channel 1324 and a second control channel 1326. The first control channel 1324 receives the first control member 1320, and the second control channel 1326 receives the second control member 1322. One or more retention pins 1317 may be received by the base member 1312 and prevent the adjustable member 1314 from becoming uncoupled from the base member 1312, as shown in FIG. 85. For example, the retention pins 1317 may contact channels 1313 and 1315 of the adjustable member 1314 to prevent the adjustable member 1314 from extending further. The channels 1313 and 1315 may align the adjustable member 1314 to the base member 1312 and further prevent the adjustable member 1314 from uncoupling from the base member 1312. Further, the channels 1313 and 1315 may define an amount of expansion allowable for the adjustable member 1314. Retention pin 1319 may be received by slot 1311 of the base member 1312 and limit translation of the first control member 1320, as shown in FIG. 81. Further, one or more retention pins 1318 may be received by the base member 1312 and contact the groove 1321 to secure the control shaft 1316, as shown in FIG. 84.

In some embodiments, the control members 1320, 1322 are received in the first control channels 1324, 1326 in a sliding manner such that the control members 1320, 1322 are able to translate within the control channels 1324, 1326. In further embodiments, each control channel has a shape such that the control channel surrounds the control member and at least partially corresponds in shape to the control member. In one embodiment, the control members 1320, 1322 are rhomboid prisms configured to engage the first and second control channels 1324, 1326. The control members 1320, 1322 include one or more flat portions 1302-1306, and an internal thread 1308. Relative to other shapes, rhomboidal control members may provide greater surface contact for the first and second control channels 1324, 1326 to increase the area over which an expanding force acts, thereby reducing part fatigue and increasing part lifetime.

Figure 82:
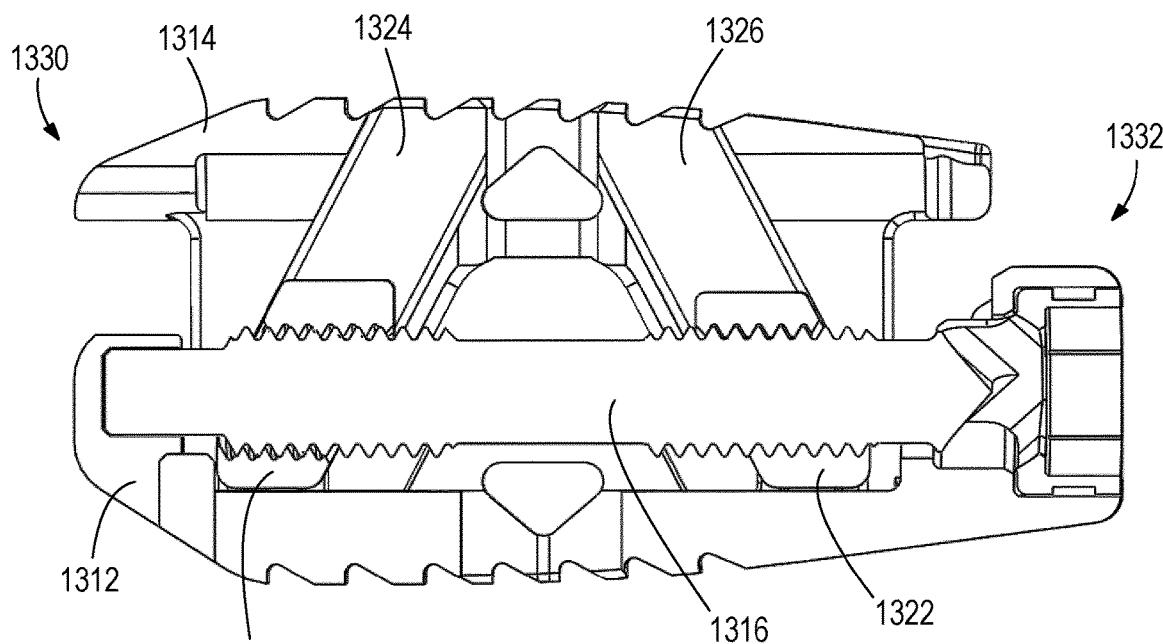
FIG. 82 is a cross section view of the implant of FIG. 79 in an expanded position according to one embodiment.
Figure 83:
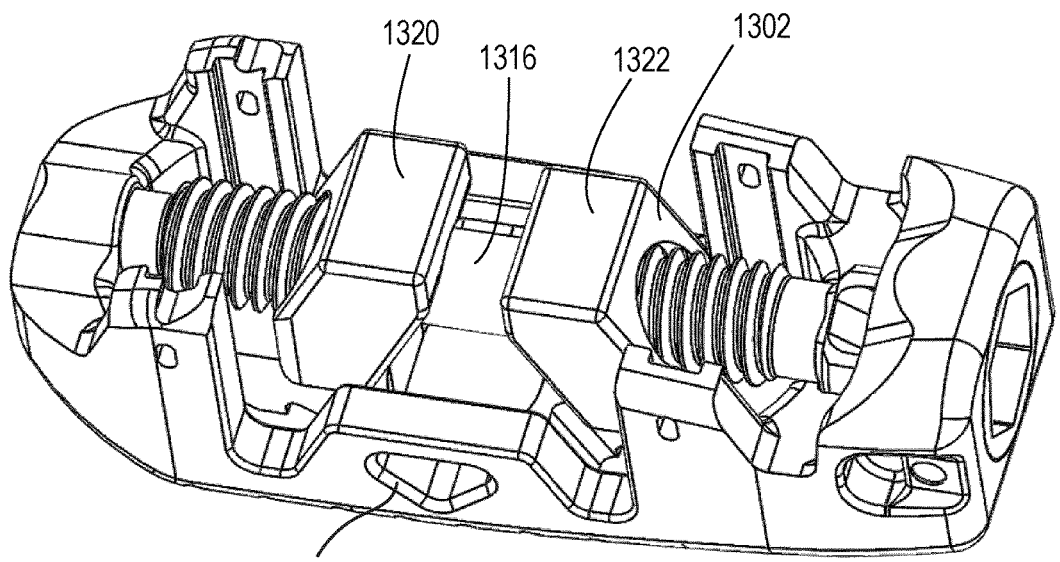
FIG. 83 is a partial cutaway view of the implant of FIG. 79 according to one embodiment.

As shown in FIGS. 81-82, as the control members 1320, 1322 move along the control shaft 1316, the control members 1320, 1322 further move within the control channels 1324, 1326, thereby causing relative movement of the adjustable member 1314 and the base member 1312. As the control members 1320, 1322 translate along the control shaft 1316, the adjustable member 1314 is moved based on the shape of the first and second control channels 1324, 1326. The rate of movement of the control members 1320, 1322, and therefore the adjustable member 1314, can be adjusted by modifying the slope of the control channels 1324, 1326 relative to the control shaft 1316 and/or by modifying the thread (e.g., lead, pitch, etc.) of the control shaft 1316 to cause greater or lesser translation of the control members 1320, 1322 for the same amount of rotation of the control shaft 1316.

In one embodiment, implant 1310 includes one or more apertures intended to provide fluid communication (e.g., for the delivery of bone growth material, etc.) between an exterior and an interior of implant 1310. For example, in one embodiment, implant 1310 includes one or more apertures 1350 extending from an exterior of implant 1310 to an interior. Aperture 1350 may be formed in base member 1312 or adjustable member 1314 and may extend through a top, bottom, side, or other surface.

Figure 86:
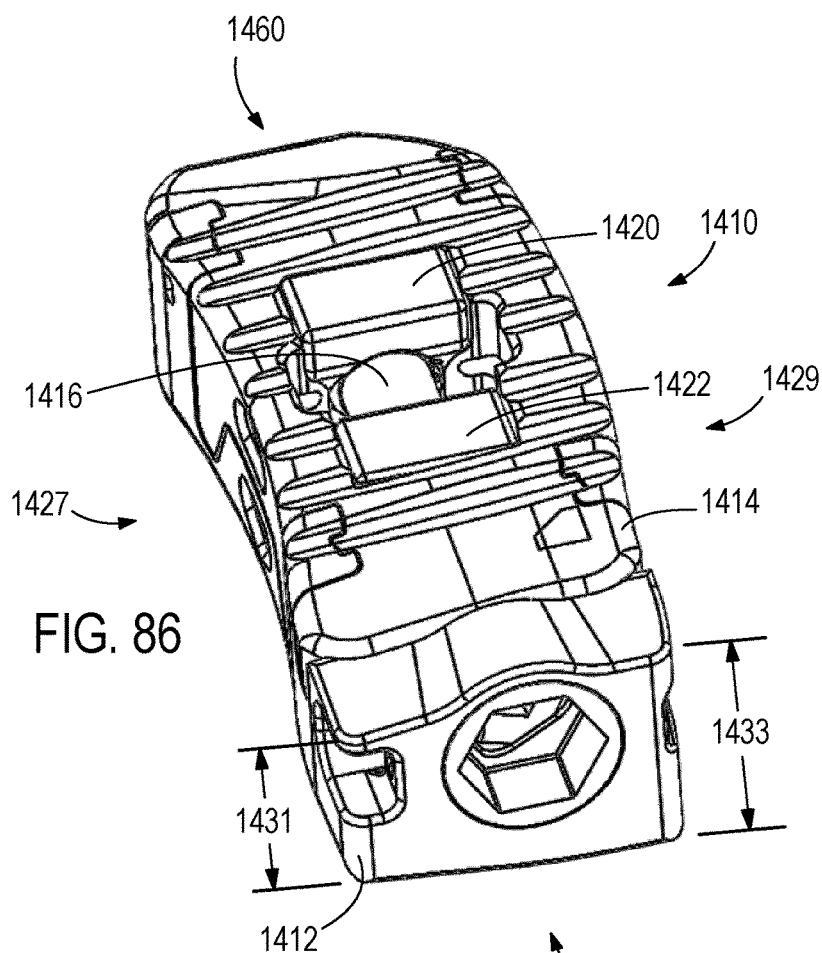
FIG. 86 is a front perspective view of an expandable implant in a collapsed position according to one embodiment.
Figure 87:
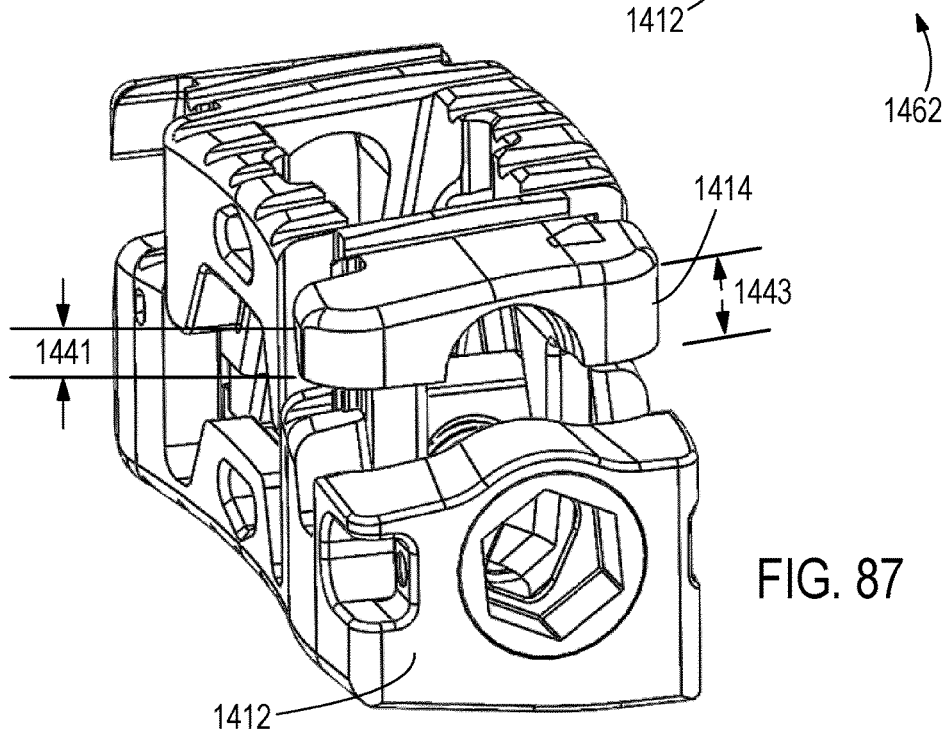
FIG. 87 is a front perspective view of the expandable implant of FIG. 86 in an expanded position according to one embodiment.
Figure 88:
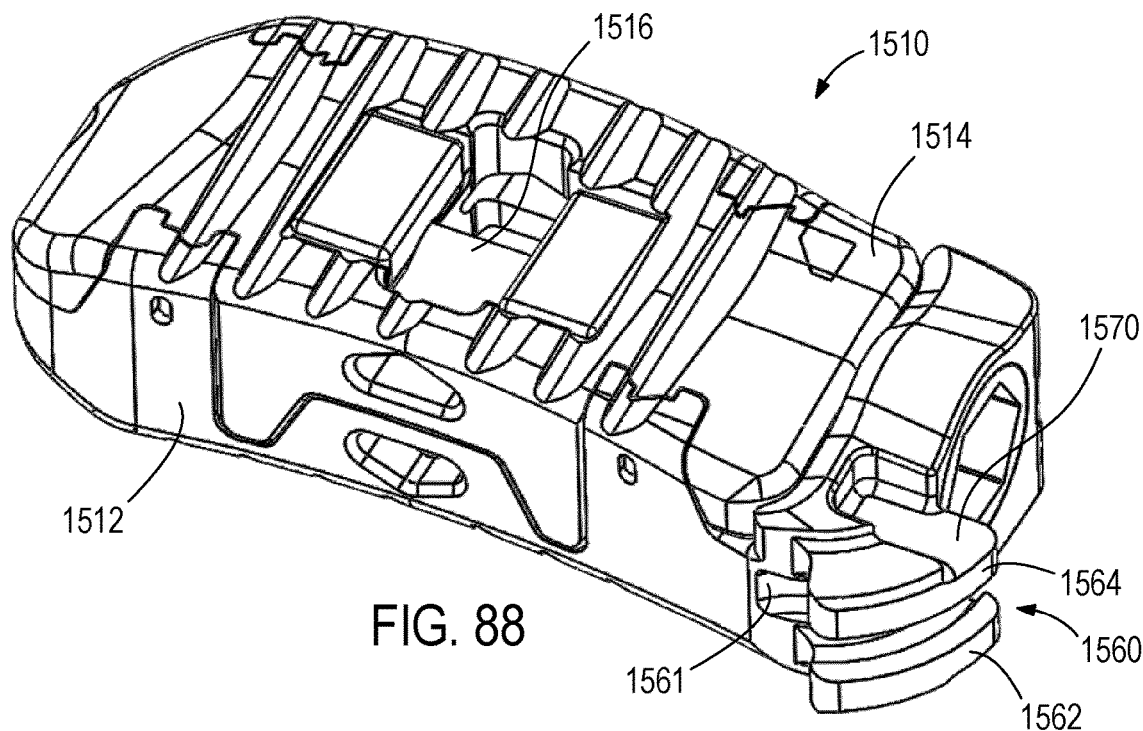
FIG. 88 is a side perspective view of an expandable implant in a collapsed position according to one embodiment.
Figure 89:
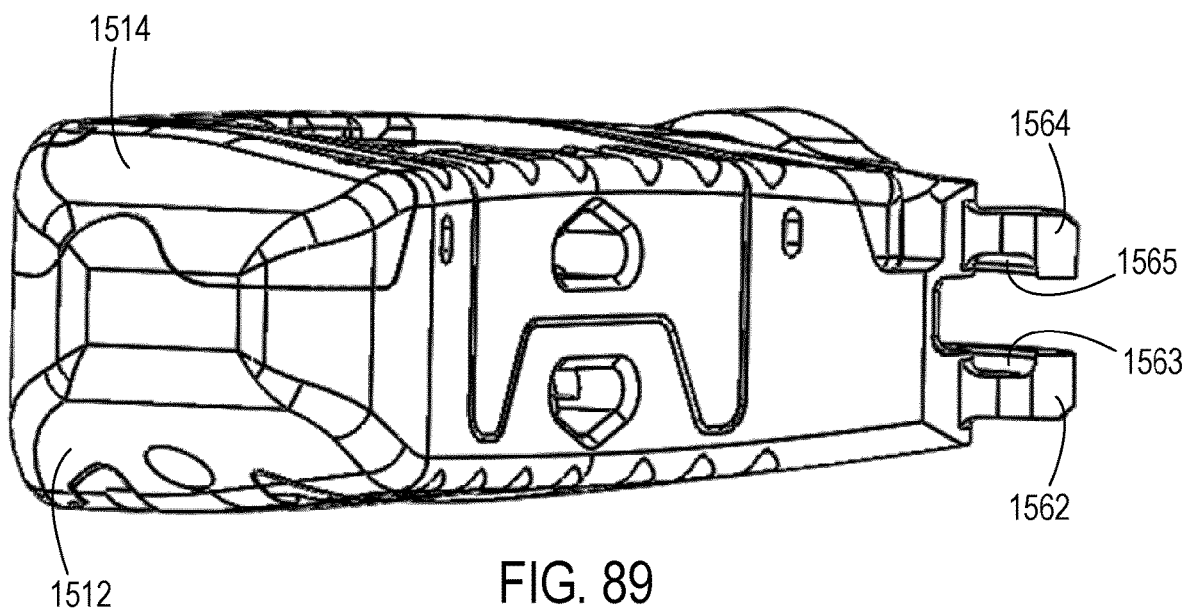
FIG. 89 is a rear perspective view of the expandable implant of FIG. 88 according to one embodiment.
Figure 90:
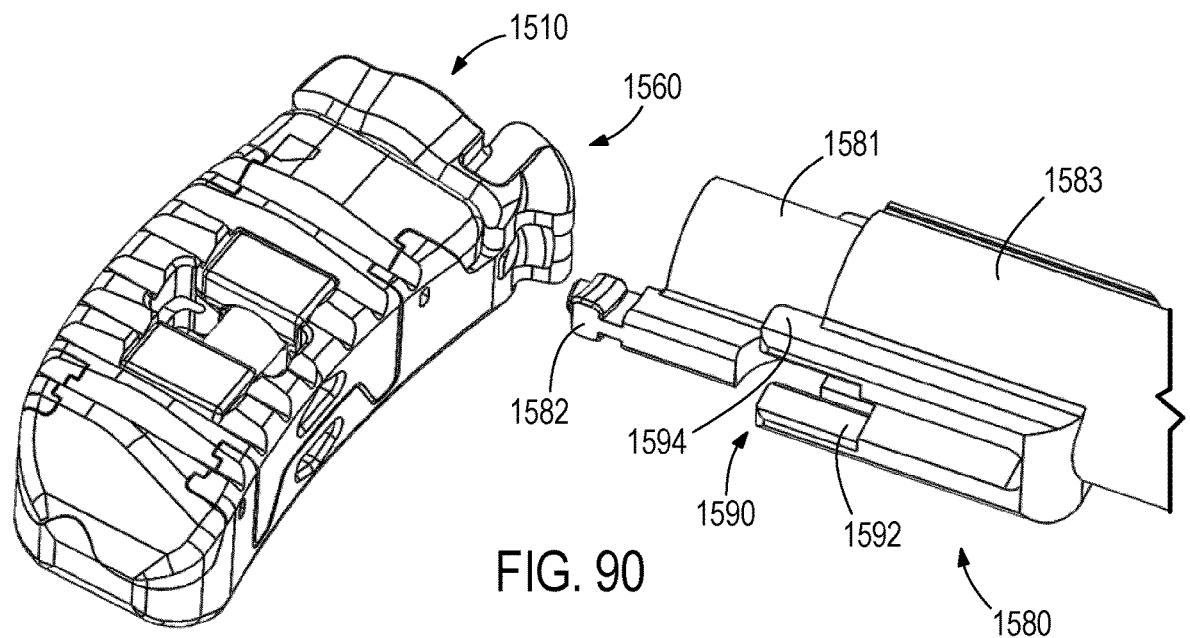
FIG. 90 is a rear perspective view of the expandable implant of FIG. 88 and a manipulation device according to one embodiment.

Referring now to FIGS. 86-87, an expandable implant 1410 is shown according to an exemplary embodiment. The implant 1410 is usable, for example, between and/or within vertebral bodies of the spine, and may include any or all of the features of the other inter/intra-body implants discussed elsewhere herein. All such combinations of features are to be understood to be within the scope of the present disclosure. It should be understood that the implant 1410 may in some embodiments be usable in other portions of the body in addition to the spine, and all such applications are to be understood to be within the scope of the present disclosure. The implant 1410 is in many ways similar to implant 1310, and may include any of the features of implant 1310 or the other implants disclosed herein.

According to an exemplary embodiment, the implant 1410 includes a base member 1412 and an adjustable member 1414 adjustably coupled to the base member 1412. A control shaft 1416 is received by the base member 1412. A first control member 1420 and a second control member 1422 are received on the control shaft 1416 and are movable along the control shaft 1416 to adjust a position of the adjustable member 1414 between a collapsed position, as shown in FIG. 86, and an expanded position, as shown in FIG. 87. The implant 1410 includes a front or first end 1460, and a back or second end 1462. According to an exemplary embodiment, the implant 1410 is substantially curved such that the sides 1427 and 1429 are curved between a first end 1460 and a second end 1462. In some embodiments, a curvature of the implant 1410 is "banana" shaped.

According to an exemplary embodiment, the implant 1410 includes a front or first side 1427, and a rear or second side 1429. The first side 1427 of the base member 1412 has a first height 1431 and the second side 1429 of the base member 1412 has a second height 1433. In some embodiments, the first height 1431 and the second height 1433 are different. For example, the second height 1433 may be greater than the first height 1431 such that the implant 1410 is substantially wedge shaped. Additionally or alternatively, the first side 1427 of the adjustable member 1414 has a first height 1441 and the second side 1429 of the adjustable member 1414 has a second height 1443.

Providing an implant with forms such as those provided by implant 1410 may facilitate accommodating a desired spinal curvature or other anatomical features where non-parallel supporting surfaces are suitable for a particular application. It should be noted that the sides (e.g., first and second side 1427 and 1429) of base member 1412 and/or adjustable member 1414 described herein may take any desired height to provide desired supporting slope for a particular implant. Furthermore, providing an implant with a curvature such as that of the implant 1410 may facilitate accommodating different shapes of bone members or other anatomical features that are substantially non-straight in form.

Referring now to FIGS. 88-99, an expandable implant 1510 is shown according to an exemplary embodiment. The implant 1510 is usable, for example, between and/or within vertebral bodies of the spine, and may include any or all of the features of the other inter/intra-body implants discussed elsewhere herein. All such combinations of features are to be understood to be within the scope of the present disclosure. It should be understood that the implant 1510 may in some embodiments be usable in other portions of the body in addition to the spine, and all such applications are to be understood to be within the scope of the present disclosure. The implant 1510 is in many ways similar to implant 1410, and may include any of the features of implant 1410 or the other implants disclosed herein. For example, implant 1510 may be substantially identical to implant 1410 with the exception of the manipulation features disclosed below.

According to an exemplary embodiment, the implant 1510 includes a base member 1512 and an adjustable member 1514 adjustably coupled to the base member 1512. A control shaft 1516 is received by the base member 1512. The base member 1512 includes an attachment member 1560 configured to allow a manipulative accessory 1580 to couple to the implant 1510 and thereby manipulate the implant 1510. The attachment member 1560 includes a bottom or first segment 1562 and a top or second segment 1564. The segments 1562, 1564 include control channels 1563 and 1565, respectively. The control channel 1563 may be located on an upper horizontal surface of the segment 1562 and the control channel 1565 may be located on a lower horizontal surface of the segment 1564. Additionally or alternatively, the base member 1512 includes control channel 1561. The control channel 1561 may be located on a vertical surface of the base member 1512. The control channels 1561, 1563, and 1565 are configured to receive and couple to coupling member 1582 of manipulative accessory 1580. Each control channel 1561, 1563, and 1565 has a shape such that the control channels 1561, 1563, and 1565 surround the coupling member 1582 and at least partially corresponds in shape to the coupling member 1582. In some embodiments, the attachment member 1560 is curved such that an orientation of the implant 1510 changes as the coupling member 1582 is inserted into the attachment member 1560.

Figure 91:
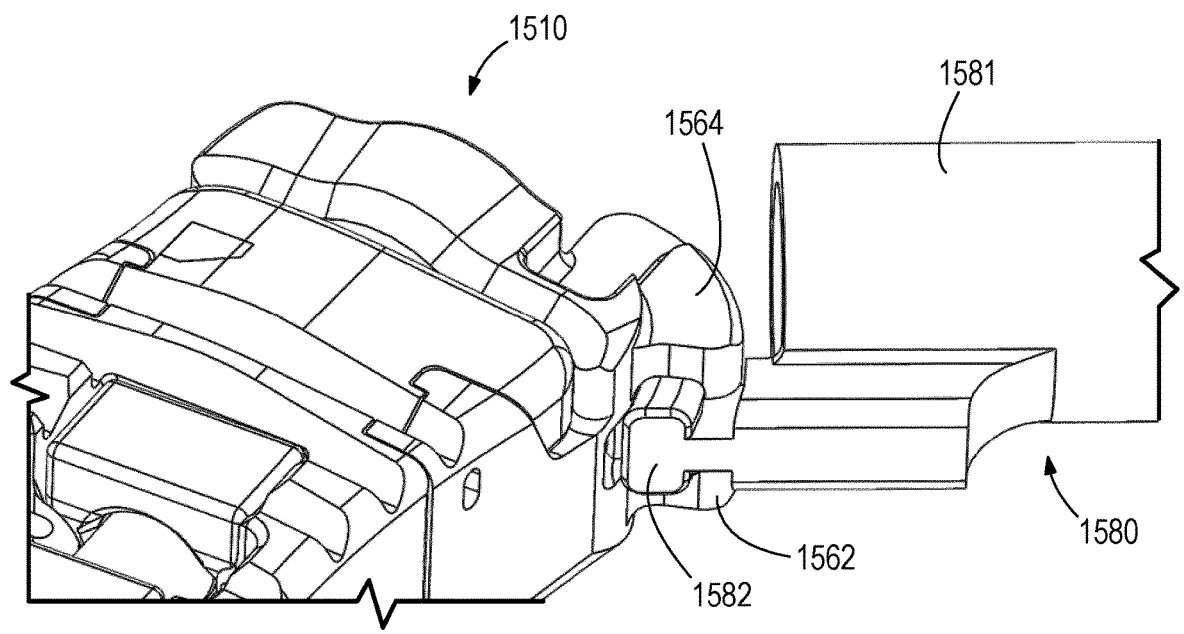
FIG. 91 is a detailed view of the expandable implant of FIG. 88 coupled to the manipulation device in a first position according to one embodiment.

In one embodiment, the attachment member 1560 includes a dovetail recess and the coupling member 1582 includes a dovetail projection. The attachment member 1560 may have a slotted opening to receive the coupling member 1582, as shown in FIG. 91. The attachment member 1560 may be configured to receive the manipulative accessory 1580 at an angle (e.g., such that a longitudinal axis of the implant is axially offset from the manipulative accessory). For example, the attachment member 1560 may receive the manipulative accessory 1580 at an 80° angle, as defined between an axis of the implant 1510 and an axis of the manipulative accessory 1580. In other embodiments, the angle is different (e.g., 70°, 90°, etc.). Additionally or alternatively, the base member 1512 includes one or more control channels, for example guide 1570. The guide 1570 is configured to receive a manipulative accessory and facilitate coupling thereto. For example, the guide 1570 may receive coupling member 1590 of the manipulative accessory 1580. The coupling member 1590 includes a bottom or first portion 1592 and a top or second portion 1594.

According to an exemplary embodiment, the coupling member 1590 is fixed to a first portion 1583 of the manipulative accessory 1580. The manipulative accessory 1580 further includes a second portion 1581 configured to couple axially within the first portion 1583. In some embodiments, the second portion 1581 is configured to translate (e.g., extend, retract, etc.) axially in/out from the first portion 1583. In some embodiments, the second portion 1581 is hollow to allow for a different tool to pass through the second portion 1581 and engage one more portions of the implant 1510. For example, an adjustment mechanism may pass through the second portion 1581 to engage an expansion mechanism of the implant 1510 to expand the implant 1510 as disclosed elsewhere herein. Additionally or alternatively, the manipulative accessory 1580 can include one or more additional elements to engage an expansion mechanism of the implant 1510 as described above. For example, the manipulative accessory 1580 may include an adjustment mechanism (e.g., a screw drive) coupled within the second portion 1581 of the manipulative accessory 1580 to engage an expansion mechanism (e.g., a screw) to expand the implant 1510.

Figure 92:
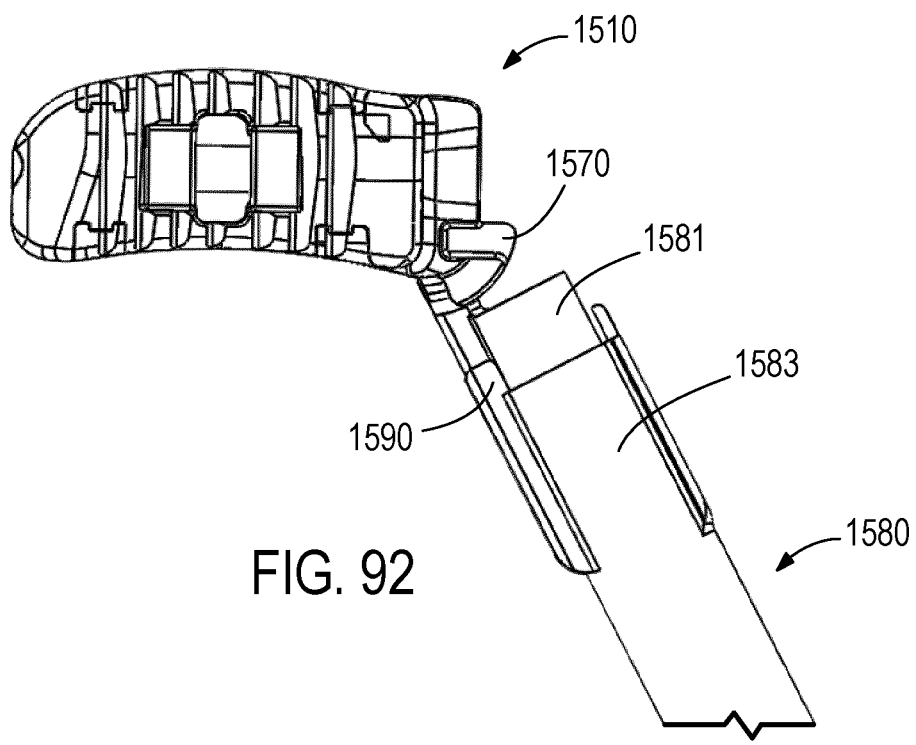
FIG. 92 is a top view of the expandable implant of FIG. 88 coupled to the manipulation device in a first position according to one embodiment.
Figure 93:
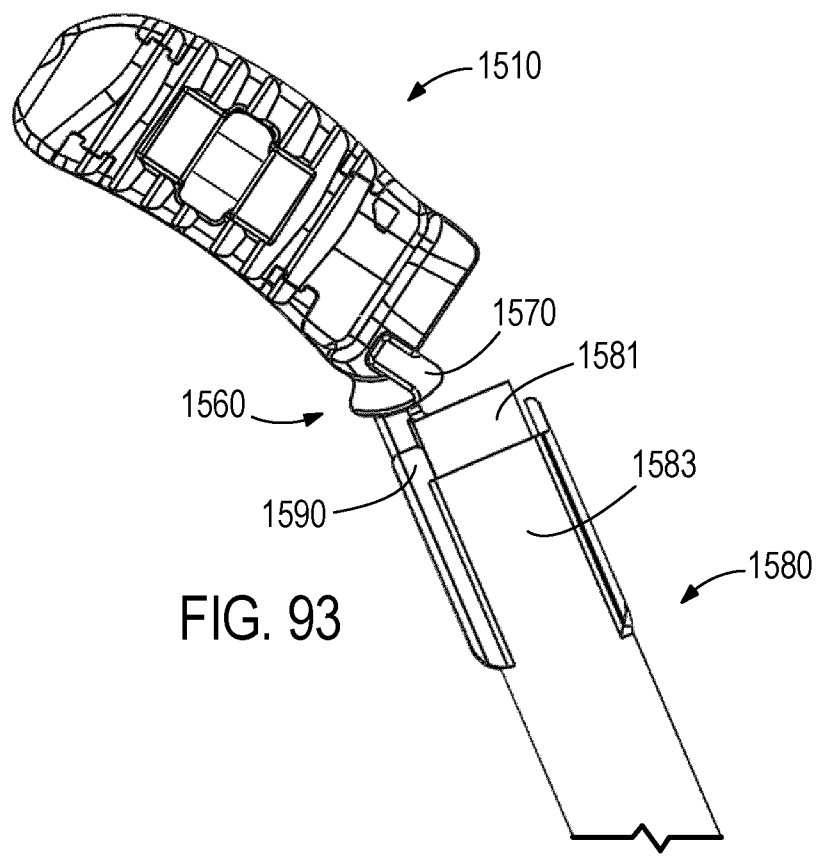
FIG. 93 is a top view of the expandable implant of FIG. 88 coupled to the manipulation device in an intermediate position according to one embodiment.
Figure 94:
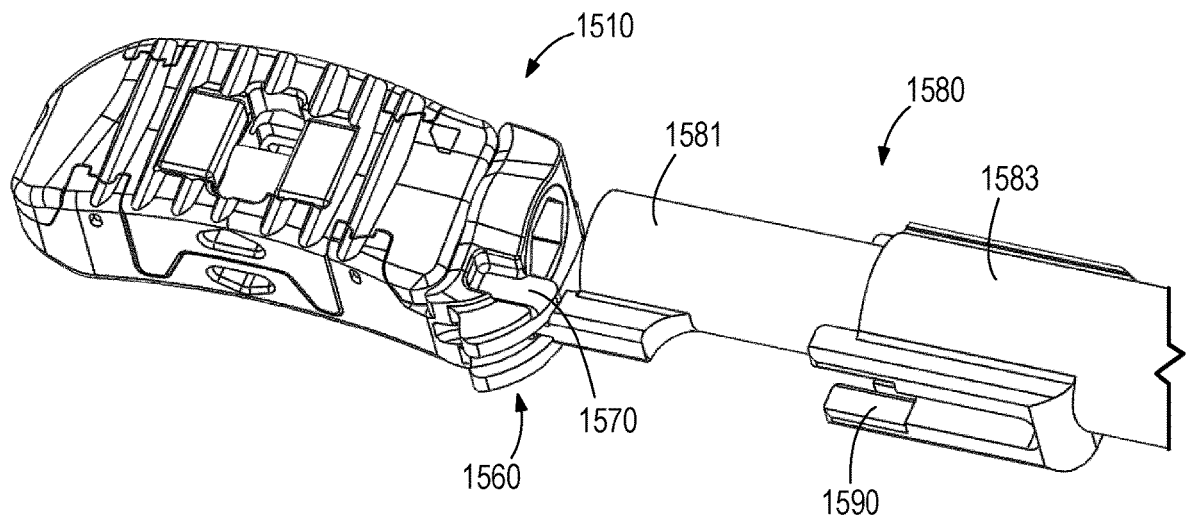
FIG. 94 is a top view of the expandable implant of FIG. 88 coupled to the manipulation device in a second position according to one embodiment.
Figure 95:
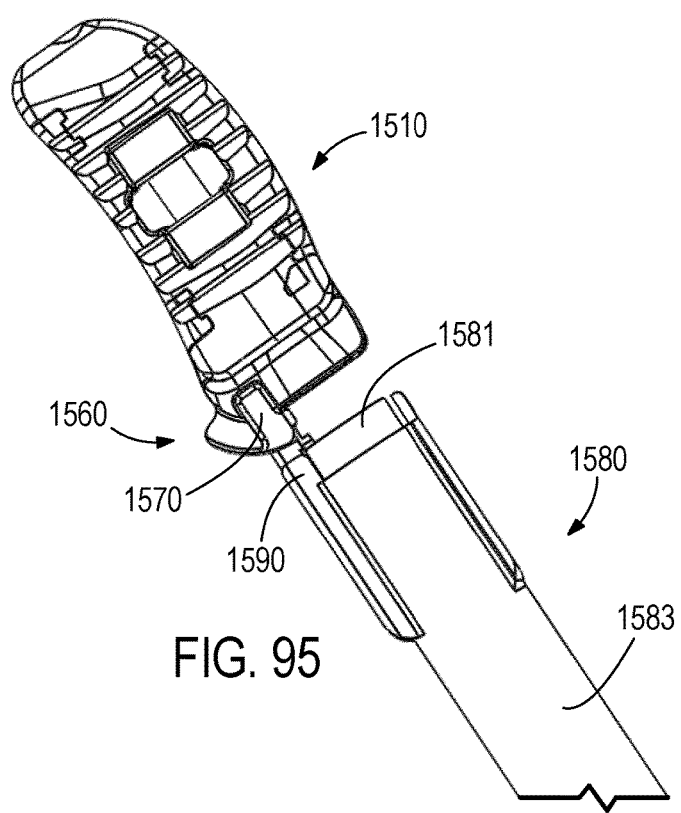
FIG. 95 is a side perspective view of the expandable implant of FIG. 88 coupled to the manipulation device in a second position according to one embodiment.
Figure 96:
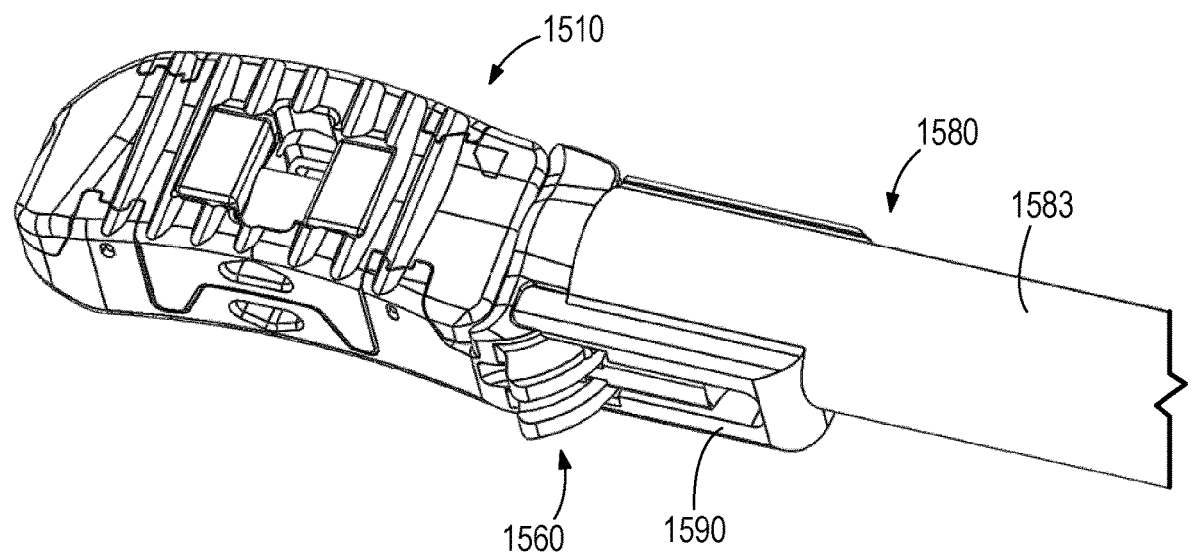
FIG. 96 is a side perspective view of the expandable implant of FIG. 88 coupled and locked to the manipulation device in a second position according to one embodiment.
Figure 97:
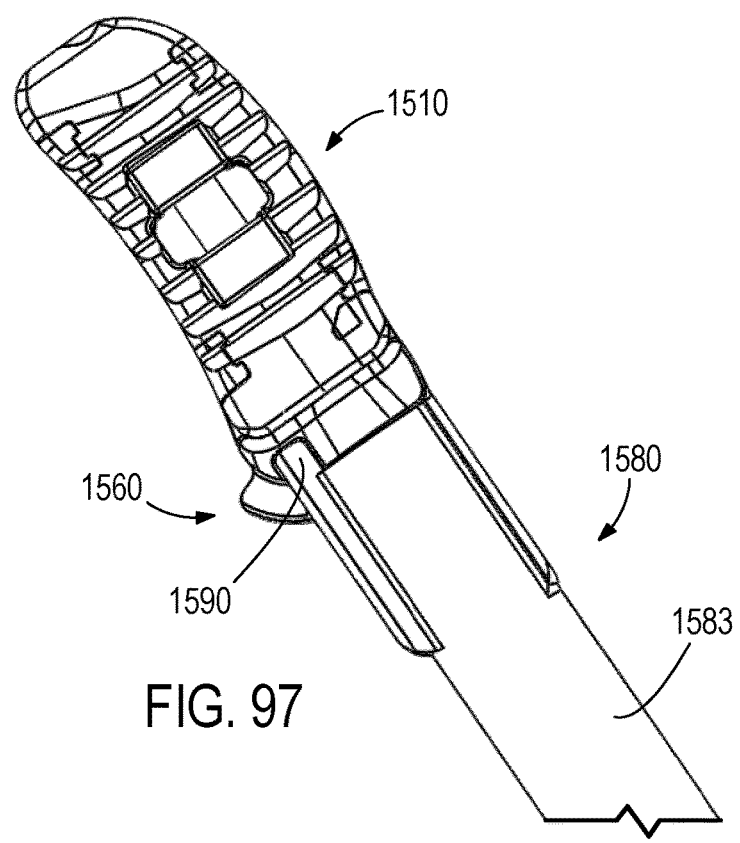
FIG. 97 is a top view of the expandable implant of FIG. 88 coupled and locked to the manipulation device in a second position according to one embodiment.

As shown in FIGS. 91-97, the manipulative accessory 1580 couples to the implant 1510. A user adjusts a position of the manipulative accessory 1580 between a first position, as shown in FIGS. 91-92 (e.g., an offset position), and a second position, as shown in FIGS. 94-97 (e.g., an aligned position). Once the manipulative accessory 1580 is in the second position, a user adjusts the second portion 1581 of the manipulative accessory 1580 between a first position, as shown in FIGS. 94-95 (e.g., a retracted position), and a second position, as shown in FIGS. 96-97 (e.g., an extended position). In the second position, the coupling member 1590 of the manipulative accessory 1580 couples to or engages the guide 1570 and thereby secures the implant 1510 to the manipulative accessory 1580 to enable a user to manipulate the implant 1510 via the manipulative accessory 1580.

Figure 98:
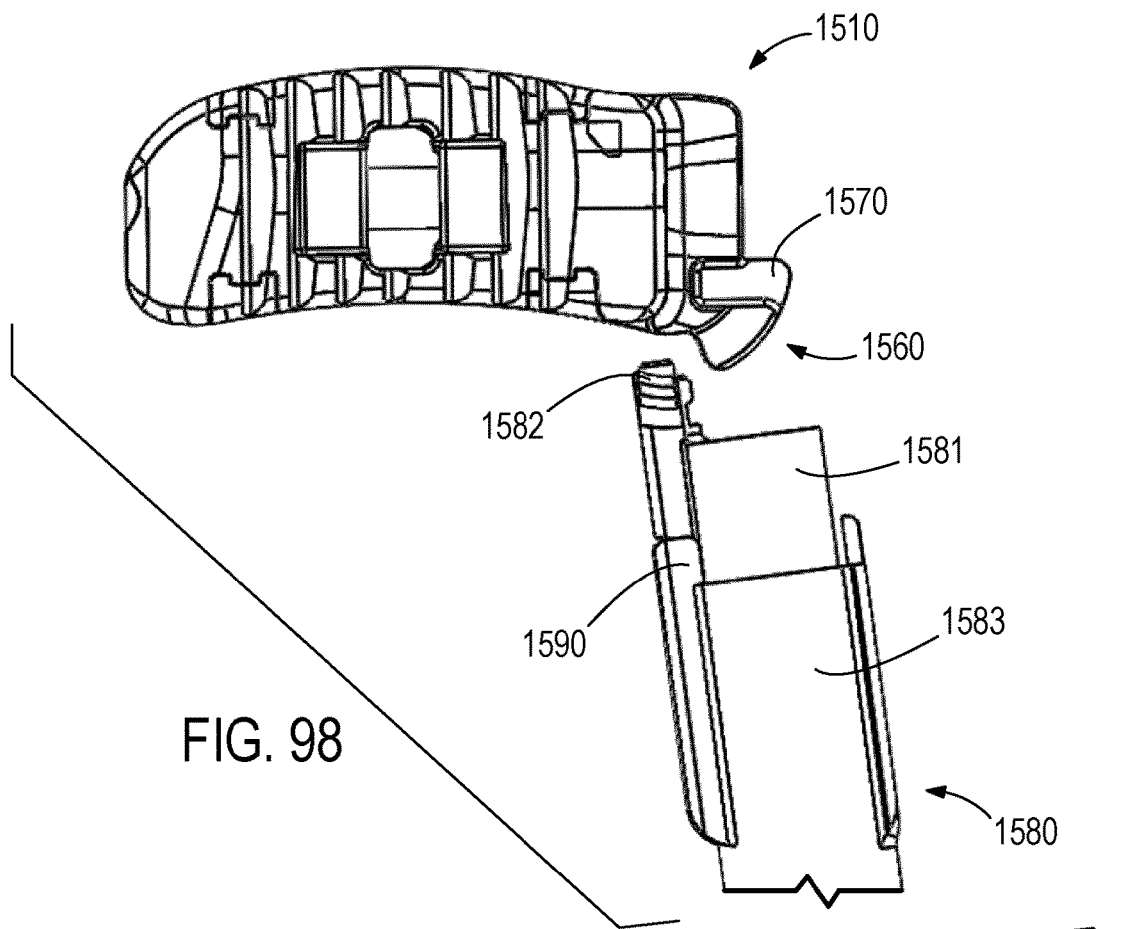
FIG. 98 is a top view of the expandable implant of FIG. 88 uncoupled from the manipulation device according to one embodiment.
Figure 99:
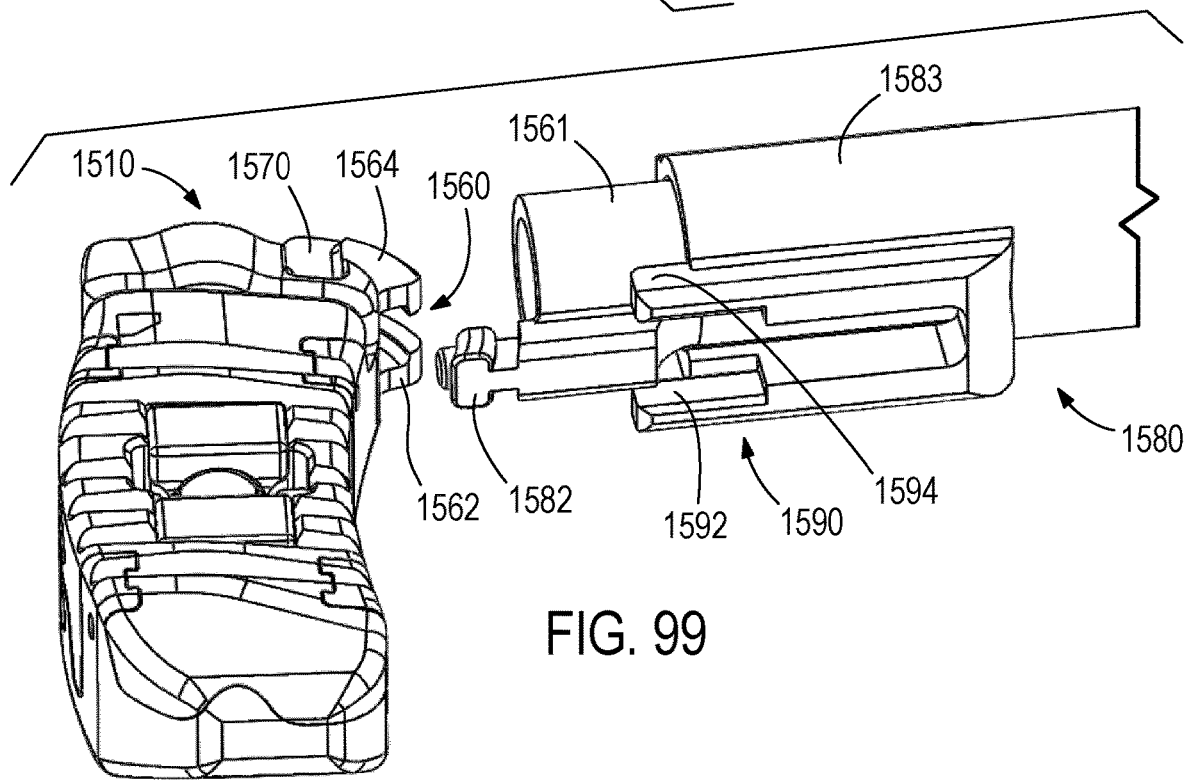
FIG. 99 is a rear perspective view of the expandable implant of FIG. 88 uncoupled from the manipulation device according to one embodiment.

An example operation of the manipulative accessory 1580 is as follows. A user (e.g., technician, surgeon, etc.) inserts the coupling member 1582 into an opening in the attachment member 1560, as shown in FIG. 91. The user then rotates the coupling member 1582 through the slot created by the control channels 1561, 1563, and 1565 of attachment member 1560 until the implant 1510 is substantially aligned with the manipulative accessory 1580, as shown in FIGS. 92-94. The user then slides the second portion 1581 of the manipulative accessory 1580 from an extended position to a retracted position, thereby engaging the coupling member 1590 and securing the implant 1510 to the manipulative accessory 1580, as shown in FIGS. 95-96. Using the manipulative accessory 1580, the user then inserts the implant 1510 into a patient and positions the implant into a final position. The user then inserts a co-axial screw drive through the manipulative accessory 1580 to engage an expansion mechanism of the implant 1510 to expand the implant 1510 thereby engaging and stabilizing adjacent portions of bone and providing therapeutic benefit. The user then disengages and withdraws the co-axial screw drive and further disengages the coupling member 1590 from the implant 1510 by sliding the second portion 1581 of the manipulative accessory 1580 from an extended position to a retracted position. The user then rotates the coupling member 1582 through the slot created by the control channels 1561, 1563, and 1565 of the attachment member 1560 in a reverse fashion as described above to disengage the manipulative accessory 1580 from the implant 1510, as shown in FIGS. 98-99. In some embodiments, the implant 1510 shown in FIGS. 98-99 is in an expanded position.

Providing an implant with attachment members and manipulative accessories such as those provided by implant 1510 may facilitate minimally invasive surgical techniques where traditional manipulative accessories are not suitable for a particular application. It should be noted that the manipulative accessory 1580 described herein may couple to any implant or any amalgam derived from the implants described herein.

Referring now to the Figures generally, the various embodiments disclosed herein provide expandable implants including a base member, an adjustable member adjustably coupled to the base member and movable between a first, collapsed position, and a second, expanded position, and a control shaft rotatably received by the base member, where rotation of the control shaft cause relative movement of the adjustable member relative to the base member. At least one control member is received on the control shaft and by the control channel, and rotation of the control shaft causes the control member to translate along the control shaft and along the control channel.

In some embodiments, the adjustable member moves in a linear fashion relative to the base member. In other embodiments, the adjustable member moves in a non-linear fashion relative to the base member. In further embodiments, the adjustable member pivots about a pivot axis relative to the base member. The pivot axis may be provided by a pivot pin extending through one or both of the adjustable member and the base member.

In some embodiments, a single control member and control channel are utilized. In other embodiments, multiple (e.g., 2) control members and control channels are utilized. In some embodiments, the multiple control channels are parallel and straight. In other embodiments, the control channels are non-parallel and straight (e.g., angled toward each other). In further embodiments, the control channels are non-parallel and non-straight such that the adjustable member moves in a non-linear fashion relative to the base member.

In some embodiments, the control shaft includes a control thread corresponding to each control member. As such, while in some embodiments the control shaft includes a single control thread, in other embodiments the control shaft includes multiple (e.g., first and second) control threads. In some embodiments, the control threads are like-threaded. In other embodiments, the control threads have different threads. For example, in some embodiments, a first control thread is opposite-handed from a second control thread. In further embodiments, a first control thread has a different pitch from a second control thread. In yet further embodiments, a first control thread is different handed and has a different pitch from a second control thread.

In some embodiments, one or both of the adjustable member and the base member include projections/grooves to provide a gripping surface intended to facilitate gripping adjacent portions of bone. In further embodiments, one or both of the adjustable member and the base member include one or more apertures and/or cavities configured to promote bone growth in and around the adjustable member and the base member. In some embodiments, the apertures extend from a top, bottom, and/or side surface of the adjustment member or the base member and to a central cavity of the implant.

According to any of the embodiments disclosed herein, one or more bone screws may be included and positioned to extend through one or both of the adjustable member and the base member and into adjacent portions of bone. In some embodiments, multiple bone screws are used. A first bone screw may extend through the adjustable member and into a first portion of bone, and a second bone screw may extend through the base member and into a second portion of bone.

In further embodiments, multiple bone screws are accessible and manipulatable by way of a front face of the implant defined by one or both of the adjustable member and the base member. A head and tool port of the control shaft may further be accessible by way of the front face of the implant.

In various embodiments, any suitable configuration of the control shaft/control member(s)/control channel(s) may be utilized. In some embodiments, an at least partially spherical control member threadingly engages a threaded control shaft and translates both along the control shaft and within the control channel. In other embodiments, the control member is non-spherical and is received at least partially on or in a control rail or control channel provided by the adjustable member, such that the control member translates along both the control shaft and the control channel or control rail.

An embodiment of the present disclosure is a method of positioning an expandable implant including receiving, by an adjustment member of the expandable implant, a manipulation tool at a first angle, wherein the adjustment member includes a channel that receives a portion of the manipulation tool. The method including securing the expandable implant to the manipulation tool by rotating the portion of the manipulation tool through the channel, the rotation orienting the expandable implant to a second angle. The method including receiving, by the adjustment member, a locking member of the manipulation tool, the locking member locking the expandable implant at the second angle. The method including positioning, by a user using the manipulation tool, the expandable implant, and receiving, by an expansion mechanism of the expandable implant, via the manipulation tool, an expansion force, the expansion force causing the expandable implant to expand.

In some embodiments, the channel is a dovetail recess and the portion of the manipulation tool is a dovetail projection. In some embodiments, the expansion force is a torque. In some embodiments, the locking member is a pin configured to fit within a slot of the adjustment member. In some embodiments, the adjustment member is coupled to a base member of the expandable implant, the base member including a bottom surface to contact an adjacent portion of bone. In some embodiments, the expandable implant including an adjustable member coupled to the base member, the adjustable member including a top surface to contact an adjacent portion of bone, the adjustable member configured to expand relative to the base member in response to the expansion force. In some embodiments, the expandable implant is perpendicular to the manipulation tool while at the first angle and is parallel to the manipulation tool while at the second angle.

Another embodiment of the present disclosure is an expandable implant including a base member including a bottom surface to contact an adjacent portion of bone, an adjustable member coupled to the base member and including a top surface to contact an adjacent portion of bone. The expandable implant further including an adjustment member including a channel and coupled to the adjustable member and configured to receive a portion of a manipulation tool at a first angle. The adjustment member further configured to secure the manipulation tool to the expandable implant by rotating the portion of the manipulation tool through the channel, wherein the rotation orients the expandable implant to a second angle, and receive a locking member of the manipulation tool, the locking member locking the expandable implant at the second angle. The expandable implant is positioned by a user using the manipulation tool and wherein the expandable implant is expanded via the manipulation tool.

In some embodiments, the channel is a dovetail recess and the portion of the manipulation tool is a dovetail projection. In some embodiments, the base member receives a screw drive to expand the expandable implant. In some embodiments, the screw drive is coupled co-axially within the manipulation tool. In some embodiments, the locking member is a pin configured to fit within a slot of the adjustment member. In some embodiments, the expandable implant is perpendicular to the manipulation tool while at the first angle and is parallel to the manipulation tool while at the second angle.

Another embodiment of the present disclosure is a manipulation tool for an expandable implant including a first portion including a first end and a second end, wherein the first end is configured to be a handle, the second end including a locking member. The manipulation tool including a second portion co-axially coupled within the second end of the first portion, the second portion configured to translate between a first position and a second position, the second portion including a coupling member configured to couple to an attachment member of the expandable implant at a first angle, wherein the coupling member secures the expandable implant to the manipulation tool by rotating through a channel of the attachment member to a second angle. Translating the second portion from the first position to the second position engages the locking member of the first portion and locks the expandable implant to the manipulation tool, locking the expandable implant at the second angle. The manipulation tool positions the expandable implant.

In some embodiments, the manipulation tool further including an adjustment mechanism co-axially coupled within the first and second portions and configured to engage the expandable implant to cause expansion. In some embodiments, the adjustment mechanism is a screw drive. In some embodiments, the channel is a dovetail recess and the coupling member is a dovetail projection. In some embodiments, the locking member is a pin configured to fit within a slot of the expandable implant. In some embodiments, the manipulation tool is perpendicular to the expandable implant at the first angle and is parallel to the expandable implant at the second angle. In some embodiments, the first and second portions are hollow.

It is important to note that the construction and arrangement of the elements of the various implants and implant components as shown in the exemplary embodiments are illustrative only. Although a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, materials, colors, orientations, etc.) without materially departing from the novel teachings and advantages of the subject matter recited in the various embodiments. Accordingly, all such modifications are intended to be included within the scope of the present disclosure as defined in the appended claims. The order or sequence of any process or method steps may be varied or re-sequenced according to alternative embodiments. Other substitutions, modifications, changes, and/or omissions may be made in the design, operating conditions, and arrangement of the exemplary embodiments without departing from the spirit of the present disclosure.

What is claimed is:

1. An expandable implant, comprising:
   a base member including a top surface, a first end, and a second end, and defining a central cavity positioned between the first end and the second end;
   an adjustable member including a top surface and at least one control channel, wherein the adjustable member is adjustably coupled to the base member and movable between a first, collapsed position, and a second, expanded position;
   a control shaft received by the base member, wherein manipulation of the control shaft causes relative movement of the adjustable member relative to the base member; and
   at least one control member coupled to the control shaft and received by the at least one control channel, wherein manipulation of the control shaft causes the at least one control member to translate along the at least one control channel;
   wherein the at least one control channel includes a first control channel and a second control channel, and wherein the at least one control member includes a first control member received in the first control channel and a second control member received in the second control channel;
   wherein the first control member and the second control member are at least partially rectangular and include a flat portion configured to engage a corresponding flat portion on the adjustable member to prevent rotation of the first control member within the first control channel and the second control member within the second control channel.

2. The expandable implant of claim 1, wherein the first control channel and the second control channel extend in non-parallel directions.

3. The expandable implant of claim 1, wherein manipulation of the control shaft comprises rotation, and wherein rotation of the control shaft causes the first and second control members to translate in opposite directions along the control shaft.

4. The expandable implant of claim 1, wherein the top surface of the adjustable member and a bottom surface of the base member define an implant height of the expandable implant and are configured to engage adjacent portions of bone.

5. The expandable implant of claim 4, wherein manipulation of the control member changes a height of the expandable implant.

6. An expandable implant, comprising:
   a base member including a central cavity positioned between a first end and a second end of the base member;
   an adjustable member coupled to the base member and movable between a collapsed position and an expanded position, the adjustable member including at least one control channel;
   a control shaft received in the central cavity of the base member, wherein manipulation of the control shaft causes the adjustable member to move between the collapsed position and the expanded position; and
   a control member received on the control shaft and in the at least one control channel and configured to provide a first wedging force to the adjustable member to move the adjustable member toward the expanded position and provide a second wedging force to the adjustable member to move the adjustable member toward the collapsed position.

7. The expandable implant of claim 6, wherein the base member has a first side and a second side, and wherein the first side and the second side are curved between the first end and the second end.

8. The expandable implant of claim 7, wherein the first side has a first height and the second side has a second height, and wherein the first height is different than the second height.

9. The expandable implant of claim 6, wherein the adjustable member has a first side and a second side, and wherein the first side and the second side are curved between the first end and the second end.

10. The expandable implant of claim 9, wherein the first side has a first height and the second side has a second height, and wherein the first height is different than the second height.

11. An expandable implant, comprising:
    a base member including a first side having a first height, a second side having a second height, a first end, and a second end, wherein the first side and the second side are curved between the first end and the second end;
    an adjustable member coupled to the base member and including a third side having a third height, a fourth side having a fourth height, a third end, and a fourth end, wherein the third side and the fourth side are curved between the third end and the fourth end, and wherein the adjustable member is movable between a collapsed position and an expanded position; and
    a control shaft rotatably received by the base member, wherein rotation of the control shaft causes the adjustable member to move between the collapsed position and the expanded position;
    wherein the first height and the second height are different; and
    wherein the third height and the fourth height are different.

12. The expandable implant of claim 11, wherein the adjustable member further comprises at least one control channel.

13. The expandable implant of claim 12, further comprising at least one control member received on the control shaft and by the control channel, wherein rotation of the control shaft causes the control member to translate along the control shaft.

14. The expandable implant of claim 13, wherein the at least one control channel includes a first control channel and a second control channel, and wherein the at least one control member includes a first control member received in the first control channel and a second control member received in the second control channel.

15. The expandable implant of claim 14, wherein the first control member and the second control member are at least partially rectangular and include a flat portion configured to engage a corresponding flat portion on the adjustable member to prevent rotation of the first control member within the first control channel and the second control member within the second control channel.

16. The expandable implant of claim 15, wherein rotation of the control shaft causes the first and second control members to translate in opposite directions along the control shaft.

17. The expandable implant of claim 11, wherein a curvature of the first side is the same as a curvature of the third side and a curvature of the second side is the same as a curvature of the fourth side.

18. The expandable implant of claim 11, wherein the first side is aligned with the third side and the second side is aligned with the fourth side when the adjustable member is in the collapsed position.

19. The expandable implant of claim 11, wherein the control shaft is configured to enable a fluid to move between an exterior of the expandable implant and an interior of the expandable implant.

20. The expandable implant of claim 6, wherein the base member and the adjustable member collectively form a tapered nose configured to facilitate positioning of the expandable implant into an implant space, wherein the tapered nose defines a forward-most portion of the expandable implant, and wherein the adjustable member forms part of the forward-most portion of the expandable implant.

21. The expandable implant of claim 6, wherein the control shaft comprises an access port providing fluid communication between an exterior of the expandable implant and the central cavity.

\* \* \* \* \*